US010538589B2

(12) United States Patent
Pardridge et al.

(10) Patent No.: US 10,538,589 B2
(45) Date of Patent: Jan. 21, 2020

(54) METHODS AND COMPOSITIONS FOR INCREASING N-ACETYLGLUCOSAMINIDASE (NAGLU) ACTIVITY IN THE CNS USING A FUSION ANTIBODY COMPRISING AN ANTI-HUMAN INSULIN RECEPTOR ANTIBODY AND NAGLU

(71) Applicant: ARMAGEN, INC., Calabasas, CA (US)

(72) Inventors: William M. Pardridge, Pacific Palisades, CA (US); Ruben J. Boado, Agoura Hills, CA (US)

(73) Assignee: ARMAGEN INC., Calabasas, CA (US)

( * ) Notice: Subject to any disclaimer, the term of this patent is extended or adjusted under 35 U.S.C. 154(b) by 0 days.

(21) Appl. No.: 14/994,067

(22) Filed: Jan. 12, 2016

(65) Prior Publication Data

US 2016/0208006 A1    Jul. 21, 2016

Related U.S. Application Data

(60) Provisional application No. 62/103,506, filed on Jan. 14, 2015.

(51) Int. Cl.
| | | |
|---|---|---|
| A61K 38/00 | (2006.01) | |
| C07K 14/00 | (2006.01) | |
| C07K 14/475 | (2006.01) | |
| C07K 14/48 | (2006.01) | |
| A61K 38/18 | (2006.01) | |
| A61K 38/19 | (2006.01) | |
| A61K 38/20 | (2006.01) | |
| A61K 38/21 | (2006.01) | |
| A61K 38/17 | (2006.01) | |
| A61K 49/00 | (2006.01) | |
| A61B 5/00 | (2006.01) | |
| A61K 39/395 | (2006.01) | |
| A61K 39/00 | (2006.01) | |
| C07K 16/28 | (2006.01) | |
| C12N 9/24 | (2006.01) | |
| C07K 16/18 | (2006.01) | |
| C07K 16/26 | (2006.01) | |
| C07K 19/00 | (2006.01) | |
| A61K 47/64 | (2017.01) | |
| A61K 45/00 | (2006.01) | |
| A61K 47/68 | (2017.01) | |

(Continued)

(52) U.S. Cl.
CPC ........ *C07K 16/2869* (2013.01); *C12N 9/2402* (2013.01); *A61K 38/00* (2013.01); *A61K 38/47* (2013.01); *A61K 39/395* (2013.01); *A61K 45/00* (2013.01); *A61K 47/64* (2017.08); *A61K 47/642* (2017.08); *A61K 47/65* (2017.08); *A61K 47/6849* (2017.08); *A61K 2039/505* (2013.01); *A61K 2039/545* (2013.01); *C07K 1/22* (2013.01); *C07K 16/18* (2013.01); *C07K 16/26* (2013.01); *C07K 16/28* (2013.01); *C07K 16/2803* (2013.01); *C07K 16/46* (2013.01); *C07K 19/00* (2013.01); *C07K 2317/14* (2013.01); *C07K 2317/24* (2013.01); *C07K 2317/55* (2013.01); *C07K 2317/565* (2013.01); *C07K 2317/567* (2013.01); *C07K 2317/92* (2013.01); *C07K 2317/94* (2013.01); *C07K 2319/00* (2013.01); *C07K 2319/30* (2013.01); *C12N 9/2465* (2013.01); *C12N 9/48* (2013.01); *C12N 9/96* (2013.01); *C12N 15/09* (2013.01); *C12Y 301/06013* (2013.01); *C12Y 302/0105* (2013.01); *C12Y 302/01076* (2013.01)

(58) Field of Classification Search
CPC .............. A61K 38/47; A61K 47/48246; A61K 2039/505; A61K 38/00; A61K 47/48269; C07K 16/2869; C07K 2317/565; C07K 16/26; C07K 2317/24; C07K 2317/92; C07K 2317/94; C07K 2319/00; C07K 2319/30; C07K 2319/74; C12N 9/14; C12N 9/2402; C12Y 302/0105; C12Y 310/01001
See application file for complete search history.

(56) References Cited

U.S. PATENT DOCUMENTS

| | | |
|---|---|---|
| 4,801,575 A | 1/1989 | Pardridge |
| 4,902,505 A | 2/1990 | Pardridge et al. |

(Continued)

FOREIGN PATENT DOCUMENTS

| | | |
|---|---|---|
| EP | 0613007 A2 | 8/1994 |
| EP | 0613007 A3 | 10/1995 |

(Continued)

OTHER PUBLICATIONS

Geografe et al., Comparative Medicine, 2003; 53: 622-632.*

(Continued)

*Primary Examiner* — Chang-Yu Wang
(74) *Attorney, Agent, or Firm* — Wilson Sonsini Goodrich & Rosati

(57) ABSTRACT

Provided herein are methods and compositions for treating a subject suffering from an enzyme deficiency in the central nervous system (CNS). The bifunctional fusion antibody provided herein comprise an antibody to an endogenous blood brain barrier (BBB) receptor and an enzyme deficient in mucopolysaccharidosis IIIB (MPS-IIIB). The fusion antibodies provided herein comprise alpha-N-acetylgulcosaminidase (NAGLU). The methods of treating an enzyme deficiency in the CNS comprise systemic administration of a fusion antibody provided herein.

10 Claims, 20 Drawing Sheets

Specification includes a Sequence Listing.

(51) Int. Cl.
| | |
|---|---|
| C07K 16/46 | (2006.01) |
| A61K 47/65 | (2017.01) |
| A61K 38/47 | (2006.01) |
| C12N 9/96 | (2006.01) |
| C12N 9/48 | (2006.01) |
| C12N 15/09 | (2006.01) |
| C07K 1/22 | (2006.01) |
| C12N 9/40 | (2006.01) |

(56) References Cited

U.S. PATENT DOCUMENTS

| | | | |
|---|---|---|---|
| 4,946,778 A | 8/1990 | Ladner et al. | |
| 5,154,924 A | 10/1992 | Friden | |
| 5,180,820 A | 1/1993 | Barde et al. | |
| 5,182,107 A | 1/1993 | Friden | |
| 5,229,500 A | 7/1993 | Barde et al. | |
| 5,438,121 A | 8/1995 | Barde et al. | |
| 5,453,361 A | 9/1995 | Yancopoulos et al. | |
| 5,527,288 A | 6/1996 | Gross et al. | |
| 5,527,527 A | 6/1996 | Friden | |
| 5,562,903 A | 10/1996 | Co et al. | |
| 5,610,279 A | 3/1997 | Brockhaus et al. | |
| 5,618,920 A | 4/1997 | Robinson et al. | |
| 5,656,284 A | 8/1997 | Balkin | |
| 5,672,683 A | 9/1997 | Friden et al. | |
| 5,693,762 A | 12/1997 | Queen et al. | |
| 5,824,782 A | 10/1998 | Hoelzer et al. | |
| 5,837,231 A | 11/1998 | Low et al. | |
| 5,848,991 A | 12/1998 | Gross et al. | |
| 5,977,307 A | 11/1999 | Friden et al. | |
| 5,997,501 A | 12/1999 | Gross et al. | |
| 6,015,662 A | 1/2000 | Hackett, Jr. et al. | |
| 6,041,775 A | 3/2000 | Century | |
| 6,060,069 A | 5/2000 | Hill et al. | |
| 6,153,190 A | 11/2000 | Young et al. | |
| 6,165,476 A * | 12/2000 | Strom | C07K 14/505 424/195.11 |
| 6,165,783 A | 12/2000 | Weiss et al. | |
| 6,201,105 B1 | 3/2001 | Smith et al. | |
| 6,248,262 B1 | 6/2001 | Kubotera et al. | |
| 6,284,262 B1 | 9/2001 | Place | |
| 6,287,792 B1 | 9/2001 | Pardridge et al. | |
| 6,322,808 B1 | 11/2001 | Trautman et al. | |
| 6,329,508 B1 | 12/2001 | Friden | |
| 6,348,210 B1 | 2/2002 | Gale | |
| 6,361,760 B1 | 3/2002 | Murata et al. | |
| 6,372,250 B1 | 4/2002 | Pardridge | |
| 6,375,975 B1 | 4/2002 | Modi | |
| 6,531,309 B1 | 3/2003 | Hu et al. | |
| 6,541,610 B1 | 4/2003 | Smith | |
| 6,582,945 B1 | 6/2003 | Raso | |
| 6,583,272 B1 | 6/2003 | Bailon | |
| 6,709,833 B2 | 3/2004 | Fukui et al. | |
| 6,743,427 B1 | 6/2004 | Schenk | |
| 6,858,206 B2 | 2/2005 | Kakkis | |
| 7,053,202 B2 | 5/2006 | O'Keefe et al. | |
| 7,078,376 B1 | 7/2006 | Thompson | |
| 7,214,658 B2 | 5/2007 | Tobinick et al. | |
| 7,226,758 B1 | 6/2007 | Lin et al. | |
| 7,294,704 B2 | 11/2007 | Simon et al. | |
| 7,309,687 B1 | 12/2007 | Brines et al. | |
| 7,341,720 B2 * | 3/2008 | Stefano | A61K 47/48215 424/94.1 |
| 7,388,079 B2 | 6/2008 | Pardridge et al. | |
| 7,700,097 B2 * | 4/2010 | Braslawsky | C07K 16/00 424/133.1 |
| 7,741,446 B2 | 6/2010 | Pardridge et al. | |
| 7,744,879 B2 * | 6/2010 | Shusta | A61K 47/48561 424/134.1 |
| 7,807,409 B2 | 10/2010 | Kopetzki | |
| 7,981,417 B2 * | 7/2011 | Shusta | A61K 47/48238 424/134.1 |
| 8,053,569 B2 | 11/2011 | Pardridge et al. | |
| 8,084,026 B2 * | 12/2011 | Glaser | C07K 16/2875 424/133.1 |
| 8,124,073 B2 * | 2/2012 | Stefano | A61K 47/48215 424/179.1 |
| 8,124,095 B2 | 2/2012 | Pardridge et al. | |
| 8,142,781 B2 | 3/2012 | Pardridge et al. | |
| 8,227,212 B2 | 7/2012 | Figura et al. | |
| 8,486,399 B2 | 7/2013 | Pardridge et al. | |
| 8,497,246 B2 | 7/2013 | Pardridge et al. | |
| 8,603,473 B2 * | 12/2013 | Glaser | C07K 16/00 424/133.1 |
| 8,715,661 B2 | 5/2014 | Pardridge et al. | |
| 8,741,260 B2 | 6/2014 | Pardridge et al. | |
| 8,753,610 B2 | 6/2014 | Pardridge et al. | |
| 8,759,297 B2 | 6/2014 | Pardridge et al. | |
| 8,834,874 B2 | 9/2014 | Pardridge et al. | |
| 8,853,353 B2 * | 10/2014 | Beliveau | A61K 38/4886 530/300 |
| 8,906,379 B2 * | 12/2014 | Stefano | A61K 47/48215 424/179.1 |
| 8,920,801 B2 | 12/2014 | Pardridge et al. | |
| 8,974,791 B2 | 3/2015 | Pardridge et al. | |
| 2002/0052311 A1 | 5/2002 | Solomon et al. | |
| 2002/0137684 A1 | 9/2002 | Tchistiakova et al. | |
| 2002/0169109 A1 | 11/2002 | Plata-Salaman et al. | |
| 2003/0129186 A1 | 7/2003 | Beliveau et al. | |
| 2003/0165853 A1 | 9/2003 | Partridge et al. | |
| 2004/0043446 A1 | 3/2004 | Defrees et al. | |
| 2004/0072291 A1 | 4/2004 | Carr et al. | |
| 2004/0101904 A1 | 5/2004 | Pardridge et al. | |
| 2004/0102369 A1 | 5/2004 | Wu et al. | |
| 2004/0229250 A1 | 11/2004 | Figura et al. | |
| 2004/0248197 A1 | 12/2004 | Holtzman et al. | |
| 2005/0026823 A1 | 2/2005 | Zankel | |
| 2005/0142141 A1 | 6/2005 | Pardridge | |
| 2005/0163782 A1 * | 7/2005 | Glaser | C07K 16/00 424/155.1 |
| 2005/0163783 A1 * | 7/2005 | Braslawsky | C07K 16/00 424/155.1 |
| 2006/0228348 A1 * | 10/2006 | Stefano | A61K 47/48215 424/94.61 |
| 2007/0031402 A1 | 2/2007 | Zhang et al. | |
| 2007/0081992 A1 | 4/2007 | Pardridge et al. | |
| 2007/0082380 A1 | 4/2007 | Pardridge et al. | |
| 2007/0275882 A1 | 11/2007 | Meijer et al. | |
| 2007/0280940 A1 | 12/2007 | Winkles et al. | |
| 2008/0003211 A1 | 1/2008 | Fogh et al. | |
| 2008/0019984 A1 * | 1/2008 | Shusta | A61K 47/48561 424/178.1 |
| 2008/0051564 A1 | 2/2008 | Pardridge et al. | |
| 2008/0152645 A1 | 6/2008 | Pardridge et al. | |
| 2008/0170994 A1 | 7/2008 | Pardridge et al. | |
| 2008/0171055 A1 | 7/2008 | Pardridge et al. | |
| 2008/0226658 A1 * | 9/2008 | Stefano | A61K 47/48215 424/179.1 |
| 2008/0292639 A1 | 11/2008 | Shen et al. | |
| 2008/0292704 A1 * | 11/2008 | Amason | A61K 39/0005 424/484 |
| 2009/0041758 A1 * | 2/2009 | Glaser | C07K 16/00 424/130.1 |
| 2009/0047338 A1 * | 2/2009 | Swamy | C12N 15/1131 424/450 |
| 2009/0068206 A1 | 3/2009 | Pardridge et al. | |
| 2009/0156498 A1 | 6/2009 | Pardridge et al. | |
| 2009/0162380 A1 * | 6/2009 | Glaser | C07K 16/2875 424/172.1 |
| 2009/0238789 A1 | 9/2009 | Guyon et al. | |
| 2009/0304696 A1 * | 12/2009 | Lawson | C07K 16/00 424/135.1 |
| 2010/0077498 A1 | 3/2010 | Pardridge et al. | |
| 2010/0098693 A1 | 4/2010 | Pardridge et al. | |
| 2010/0172919 A1 | 7/2010 | Grimm et al. | |
| 2010/0183577 A1 * | 7/2010 | Stern | A61K 47/48269 424/94.3 |
| 2010/0209425 A1 * | 8/2010 | Shusta | A61K 47/48238 424/135.1 |
| 2010/0261647 A1 | 10/2010 | Pardridge et al. | |
| 2010/0290985 A1 | 11/2010 | Pardridge et al. | |

(56) References Cited

U.S. PATENT DOCUMENTS

| | | |
|---|---|---|
| 2011/0110935 A1 | 5/2011 | Pardridge et al. |
| 2011/0262460 A1* | 10/2011 | Shusta ............ A61K 47/48238 424/172.1 |
| 2011/0318327 A1* | 12/2011 | Concino ............ A61K 9/0085 424/94.61 |
| 2012/0014936 A1 | 1/2012 | Natoli et al. |
| 2012/0094934 A1 | 4/2012 | Collard et al. |
| 2012/0141507 A1* | 6/2012 | Stefano ............ A61K 47/48215 424/179.1 |
| 2012/0232021 A1* | 9/2012 | Martini ................ A61K 38/30 514/21.2 |
| 2012/0269807 A1 | 10/2012 | Pardridge et al. |
| 2013/0039888 A1* | 2/2013 | McCarty ................ C12N 9/14 424/93.2 |
| 2013/0095092 A1* | 4/2013 | Quinn .................... A61K 38/47 424/94.61 |
| 2013/0142794 A1* | 6/2013 | Pardridge .......... C07K 16/2869 424/134.1 |
| 2013/0287773 A1 | 10/2013 | Pardridge et al. |
| 2013/0295077 A1* | 11/2013 | Concino ............ A61K 9/0085 424/94.61 |
| 2014/0037621 A1* | 2/2014 | Tsurushita ......... C07K 16/2878 424/133.1 |
| 2014/0187502 A1* | 7/2014 | Martini ................ A61K 38/30 514/21.2 |
| 2014/0193409 A1 | 7/2014 | Pardridge et al. |
| 2014/0288273 A1 | 9/2014 | Pardridge et al. |
| 2014/0294822 A1 | 10/2014 | Pardridge et al. |
| 2015/0004160 A1 | 1/2015 | Pardridge et al. |
| 2015/0023956 A1* | 1/2015 | Pardridge .......... C07K 16/2869 424/134.1 |
| 2015/0064184 A1 | 3/2015 | Pardridge et al. |
| 2015/0203586 A1 | 7/2015 | Pardridge et al. |
| 2015/0299328 A1 | 10/2015 | Pardridge et al. |
| 2015/0320844 A1* | 11/2015 | Stefano ............ A61K 47/48215 424/94.3 |
| 2016/0152719 A1 | 6/2016 | Pardridge |
| 2017/0066832 A1 | 3/2017 | Pardridge |
| 2017/0114152 A1 | 4/2017 | Pardridge |

FOREIGN PATENT DOCUMENTS

| | | |
|---|---|---|
| EP | 2051734 A2 | 4/2009 |
| EP | 2182980 A2 | 5/2010 |
| EP | 2408474 A2 | 1/2012 |
| EP | 2485761 A1 | 8/2012 |
| EP | 2785378 A1 | 10/2014 |
| JP | H06228199 A | 8/1994 |
| WO | WO-9802421 A1 | 1/1998 |
| WO | WO-9900150 A2 | 1/1999 |
| WO | WO-9900951 A1 | 1/1999 |
| WO | WO-9900150 A3 | 4/1999 |
| WO | WO-9966951 A2 | 12/1999 |
| WO | WO-0015759 A1 | 3/2000 |
| WO | WO-0037502 A2 | 6/2000 |
| WO | WO-0051621 A1 | 9/2000 |
| WO | WO-0145730 A2 | 6/2001 |
| WO | WO-03074081 A1 | 9/2003 |
| WO | WO-2004003019 A2 | 1/2004 |
| WO | WO-2004050016 A2 | 6/2004 |
| WO | WO-2004108071 A2 | 12/2004 |
| WO | WO-2006081171 A1 | 8/2006 |
| WO | WO-2007022416 A2 | 2/2007 |
| WO | WO-2007044323 A2 | 4/2007 |
| WO | WO-2007022416 A3 | 5/2007 |
| WO | WO-2008022349 A2 | 2/2008 |
| WO | WO-2009018122 A2 | 2/2009 |
| WO | WO-2007044323 A3 | 5/2009 |
| WO | WO-2009070597 A2 | 6/2009 |
| WO | WO-2010003101 A2 | 1/2010 |
| WO | WO-2010108048 A2 | 9/2010 |
| WO | WO-2011044542 A1 | 4/2011 |
| WO | WO-2013081706 A1 | 6/2013 |
| WO | WO-2015009961 A1 | 1/2015 |
| WO | WO-2015012944 A1 | 1/2015 |

OTHER PUBLICATIONS

Advisory action dated Jun. 13, 2014 for U.S. Appl. No. 13/141,682.

Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.

Ai, et al., 2003. Intraputamenal Infusion of GDNF in Aged Rhesus Monkeys: Distribution and Dopaminergic Effects. The Journal of Comparative Neurology 461: 250-261.

Airavaara, et al. Effects of repeated morphine on locomotion, place preference and dopamine in heterozygous glial cell line-derived neurotrophic factor knockout mice. Genes Brain Behav. Apr. 2007;6(3):287-98.

Akiyama, et al. Enzyme augmentation therapy enhances the therapeutic efficacy of bone marrow transplantation in mucopolysaccharidosis type II mice. Mol Genet Metab. Feb. 2014;111(2):139-46. doi: 10.1016/j.ymgme.2013.09.013. Epub Sep. 21, 2013.

Al Sawaf, et al. Neurological findings in Hunter disease: pathology and possible therapeutic effects reviewed. J Inherit Metab Dis. Aug. 2008;31(4):473-80.

Albayrak, et al. Effect of transient focal ischemia on blood-brain barrier permeability in the rat: Correlation to Cell Injury. Acta Neuropathol 1997;94:158-63.

Albeck, et al. A non-invasive transport system for GDNF across the blood-brain barrier. NeuroReport. Jul. 7, 1997; 8(9-10):2293-2298.

Alberts, et al. Molecular Biology of the Cell. 3rd Edition. Garland Publishing Inc. New York. 1994; pp. 1206-1207.

Almagro, J. Identification of differences in the specificity-determining residues of antibodies that recognize antigens of different size: implications for the rational design of antibody repertoires. J Mol Recognit. Mar.-Apr. 2004;17(2):132-43.

Altschul, et al. Optimal sequence alignment using affine gap costs. Bulletin of Mathematical Biology. 1986; 48(5-6):603-16.

Altschul et al., Basic local alignment search tool. J Mol Biol. Oct. 5, 1990;215(3):403-10.

Altschul, et al. Gapped BLAST and PSI-BLAST: a new generation of protein database search programs. Nucleic Acids Res. 1977;25:3389-402.

AMGEN www.amgen.com Accessed Dec. 16, 2005.

Arndt, et al. Generation of a highly stable, internalizing anti-CD22 single-chain Fv fragment for targeting non-Hodgkin's lymphoma. Int J Cancer. Dec. 10, 2003;107(5):822-829.

Aronovich et al., "Molecular Genetic Defect Underlying α-L-Iduronidase pseudodeficiency," Am. Journ. Hum. Genet. 58: 75-85 (1996).

Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme. 2009.10.002. Epub Oct. 13, 2009.

Ausubel, et al. Current Protocols in Molecular Biology. John Wiley & Sons, New York, 1995 supplement.

Bachis, et al. 2003. Brain-Derived Neurotropic Factor Inhibits Human Immunodeficiency Virus-1/gp 120—Mediated Cerebellar Granule Cell Death by Preventing gp 120 Internalization. The Journal of Neuroscience 23 (13): 5712-22.

Baloh, et al. Functional mapping of receptor specificity domains of glial cell line-derived neurotrophic factor (GDNF) family ligands and production of GFRalpha1 RET-specific agonists. J Biol Chem. Feb. 4, 2000;275(5):3412-20.

Barth et al. Boron neutron capture therapy of brain tumors: an emerging therapeutic modality. Neurosurgery. Mar. 1999;44(3):433-50; discussion 450-1.

Batzer, et al. Enhanced evolutionary PCR using oligonucleotides with inosine at the 3'-terminus. Nucleic Acid Res.1991;19:5081.

(56) References Cited

OTHER PUBLICATIONS

Beck, et al. 1994. Brain-Derived Neurotropic Factor Protects Against Ischemic Cell Damage in Rat Hippocampus. Journal of Cerebral Blood Flow and Metabolism 14: 689-92.
Begley et al., "Lysosomal storage diseases and the blood-brain barrier," Current Pharmaceutical Design, vol. 14, No. 16, pp. 1566-1580 (2008).
Benito, et al. Beta-galactosidase enzymatic activity as a molecular probe to detect specific antibodies. J Biol Chem. Aug. 30, 1996;271(35):21251-6.
Bickel; et al., "In vivo demonstration of subcellular localization of anti-transferrin receptor monoclonal antibody-colloidal gold conjugate in brain capillary endothelium", Nov. 1994, 42(11), 1493-7.
Bifare, et al. 2005. Brain-Derived Neurotropic Factor Protects against Multiple Forms of Brain Injury in Bacterial Meningitis. The Journal of Infectious Diseases 191: 40-45.
Biogen IDEC www.idecpharma.com/site/home.html Accessed Dec. 16, 2005.
Boado, et al. AGT-181: expression in CHO cells and pharmacokinetics, safety, and plasma iduronidase enzyme activity in Rhesus monkeys. Oct. 2009; 144(2):135-41.
Boado, et al. Blood-brain barrier molecular trojan horse enables imaging of brain uptake of radioiodinated recombinant protein in the rhesus monkey. Bioconjug Chem. Oct. 16, 2013;24(10):1741-9. doi: 10.1021/bc400319d. Epub Oct. 3, 2013.
Boado, et al. CHO cell expression, long-term stability, and primate pharmacokinetics and brain uptake of an IgG-paroxonase-1 fusion protein. Biotechnol Bioeng. Jan. 2011;108(1):186-96.
Boado, et al. Drug delivery of antisense molecules to the brain for treatment of Alzheimer's disease and cerebral AIDS. J Pharm Sci. Nov. 1998;87(11):1308-15.
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010; 961-969.
Boado, et al. Engineering and expression of a chimeric transferrin receptor monoclonal antibody for blood-brain barrier delivery in the mouse. Biotechnol Bioeng. Mar. 1, 2009;102(4):1251-8.
Boado, et al. Fusion Antibody for Alzheimer's Disease with Bi-Directional Transport Across the Blood-Brain Barrier and Abeta Fibril Disaggregation. Bioconjug Chem. 2007;18(2):447-55.
Boado, et al. GDNF fusion protein for targeted-drug delivery across the human blood-brain barrier. Biotechnol Bioeng. Jun. 1, 2008;100(2):387-96.
Boado, et al. Genetic engineering, expression, and activity of a fusion protein of a human neurotrophin and a molecular Trojan horse for delivery across the human blood-brain barrier. Biotechnology and Bioengineering. 2007;97:1376-1386.
Boado et al., "Genetic engineering of a lysosomal enzyme fusion protein for targeted delivery across the human blood-brain barrier," Biotechnology and Bioengineering, vol. 99, No. 2, pp. 475-484 (2008).
Boado et al., "Genetic Engineering of IgG-glucuronidase fusion proteins," J. Drug Targeting 18(3):205-11 (2010).
Boado, et al. Glycemic control and chronic dosing of rhesus monkeys with a fusion protein of iduronidase and a monoclonal antibody against the human insulin receptor. Drug Metab Dispos. Oct. 2012;40(10):2021-5. doi: 10.1124/dmd.112.046375. Epub Jul. 20, 2012.
Boado et al. Humanization of anti-human insulin receptor antibody for drug targeting across the human blood-brain barrier. Biotechnology and Bioengineering. 2007;96:381-391.
Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).
Boado et al., "Pharmacokinetics and brain uptake of a genetically engineered bifunctional fusion antibody targeting the mouse transferrin receptor," Molecular Pharmaceutics, vol. 7, No. 1, pp. 237-244 (2010).
Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Boado, et al. Selective targeting of a TNFR decoy receptor pharmaceutical to the primate brain as a receptor-specific IgG fusion protein. J Biotechnol. Mar. 2010;146(1-2):84-91.
Boado, Ruben J. et al. Glycemic Control and Chronic Dosing of Rhesus Monkeys with a Fusion Protein of Iduroniadase and a Monoclonal Antibody Against the Human Insulin Receptor Drug Metabolism andDisposition vol. 40, No pp. 2021-2025 (2012).
Board of Patent Appeals and Interferences (BPAI) Decision dated Jul. 22, 2010 from U.S. Appl. No. 11/061,956.
Bosslet, et al. Molecular and functional characterisation of a fusion protein suited for tumour specific prodrug activation. Br J Cancer. Feb. 1992;65(2):234-8.
Bosslet, et al. Tumor-selective prodrug activation by fusion protein-mediated catalysis. Cancer Res. Apr. 15, 1994;54(8):2151-9.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Brines, et al. Erythropoietin crosses the blood-brain barrier to protect against experimental brain injury, Proc Natl Acad Sci USA. 2000; 97:10526-10531.
Brummell, et al. Probing the combining site of an anti-carbohydrate antibody by saturation-mutagenesis: role of the heavy-chain CDR3 residues. Biochemistry. 1993; 32(4):1180-7.
Buchli, et al. Inhibition of Nogo: a key strategy to increase regeneration, plasticity and functional recovery of the lesioned central nervous system. Ann Med. 2005;37(8):556-67.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Byrn, et al. Biological properties of a CD4 immunoadhesin. Nature. Apr. 12, 1990;344(6267):667-70.
Carnicella, et al. GDNF is a fast-acting potent inhibitor of alcohol consumption and relapse. Proc Natl Acad Sci U S A. Jun. 10, 2008;105(23):8114-9.
Casset, et al. A peptide mimetic of an anti-CD4 monoclonal antibody by rational design. Biochem Biophys Res Commun. Jul. 18, 2003;307(1):198-205.
Cassol, et al. Stability of dried blood spot specimens for detection of human immunodeficiency virus DNA by polymerase chain reaction. J Clin Microbiol. Dec. 1992;30(12):3039-42.
Chamow, et al. Immunoadhesins: principles and applications. Trends Biotechnol. Feb. 1996;14(2):52-60.
Chen, et al. Cotranslational folding and calnexin binding during glycoprotein synthesis. Proc Natl Acad Sci U S A. Jul. 3, 1995;92(14):6229-33.
Chen, et al. In vitro scanning saturation mutagenesis of all the specificity determining residues in an antibody binding site. Protein Engineering. 1999; vol. 12, No. 4, 349-56.
Cheng, et al. 1997. Marked Age-dependent Neuroprotection by Brain-derived Neurotropic Factor Against Neonatal Hypoxic-Ischemic Brain Injury. Annals of Neurology 41 (4): 521-29.
Cheng, et al. 2004. Neuroprotection for Ischemic Stroke: Two Decades of Success and Failure. The Journal of the American Society for Experimental Neuro Therapeutics 1: 36-45.
Chothia, et al. Canonical structures for the hypervariable regions of immunoglobulins. J Mol Biol. Aug. 20, 1987;196(4):901-17.
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008. 10.020. Epub Oct. 29, 2008.
Chung et al. Antibodies against West Nile Virus nonstructural protein NS1 prevent lethal infection through Fc gamma receptor-dependent and -independent mechanisms. J Virol. Feb. 2006;80(3):1340-51.
Clements, et al. Human alpha-L-iduronidase. 1. Purification, monoclonal antibody production, native and subunit molecular mass. Eur J Biochem. Oct. 1, 1985;152(1):21-8.

(56) References Cited

OTHER PUBLICATIONS

Clements, et al. Immunopurification and characterization of human alpha-L-iduronidase with the use of monoclonal antibodies. Biochem J. Apr. 1, 1989;259(1):199-208.
Colman, P.M. Effects of amino acid sequence changes on antibody-antigen interactions. Res Immunol. Jan. 1994:145(1):33-6.
Coloma, et al. 1997. Design and production of novel tetravalent bispecific antibodies. Nat Biotechnol Feb;15(2):159-63.
Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.
Coloma, et al. The hinge as a spacer contributes to covalent assembly and is required for function of IgG. J Immunol. Jan. 15, 1997;158(2):733-40.
Corchero, et al. The position of the heterologous domain can influence the solubility and proteolysis of beta-galactosidase fusion proteins in *E. coli*. J Biotechnol. Jul. 31, 1996;48(3):191-200.
Cosma, et al. The multiple sulfatase deficiency gene encodes an essential and limiting factor for the activity of sulfatases. Cell. May 16, 2003;113(4):445-56.
Cowen, et al. 2004. Neuropeptides: implications for alcoholism. Journal of Neurochemistry 89: 273-85.
Crow, et al. Biochemical and histopathological studies on patients with mucopolysaccharidoses, two of whom had been treated by fibroblast transplantation. J Clin Pathol. 1983;36(4):415-30.
Dawson, et al. A comparative assessment of the efficacy and side-effect liability of the neuroprotective compounds in experimental stroke. 2001. Brain Research 892: 344-50.
De Graaf, M. et al., "Expression of scFvs and scFv Fusion Proteins in Eukaryotic Cells." Mol. Biol. 2002; 178:379-387.
De Pascalis, et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Deane, et al. IgG-assisted age-dependent clearance of Alzheimer's amyloid beta peptide by the blood-brain barrier neonatal Fc receptor. J Neurosci. 2005; 25(50):11495-503.
Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.
Dierks, et al. Conversion of cysteine to formylglycine in eukaryotic sulfatases occurs by a common mechanism in the endoplasmic reticulum. FEBS Lett. Feb. 13, 1998;423(1):61-5.
Dierks, et al. Sequence determinants directing conversion of cysteine to formylglycine in eukaryotic sulfatases. EMBO J. Apr. 15, 1999;18(8):2084-91.
Dreier, et al. Recombinant immunocytokines targeting the mouse transferrin receptor: construction and biological activities. Bioconjug Chem. Jul.-Aug. 1998;9(4):482-9.
Duchnowska, et al. Central nervous system metastases in breast cancer patients administered trastuzumab. Cancer Treat Rev. Jun. 2005;31(4):312-8.
Duffy, et al. 1987. Blood-brain barrier transcytosis of insulin in developing rabbits. Brain Research 420: 32-38.
Duffy, et al. 1988. Human blood-brain barrier insulin-like growth factor receptor. Metabolism. Feb;37(2):136-40.
Durrington, et al. Paraoxonase and atherosclerosis. Arterioscler Thromb Vasc Biol. Apr. 2001;21(4):473-80.
Ehrenreich, et al. Erythropoietin therapy for acute stroke is both safe and beneficial. Mol Med. Aug. 2002;8(8):495-505.
Eketjall, et al. Distinct structural elements in GDNF mediate binding to GFRalpha1 and activation of the GFRalpha1-c-Ret receptor complex. EMBO J. Nov. 1, 1999;18(21):5901-10.

Elliott, et al. Control of rHuEPO biological activity: the role of carbohydrate. Exp Hematol. Dec. 2004;32(12):1146-55.
EP06825389.7 Search Report dated Feb. 23, 2010.
EP07841110.5 Search Report and opinion dated Dec. 2, 2010.
EP08796594.3 Search Report and opinion dated Mar. 16, 2012.
Eslamboli, et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005:25:769-77.
European Application No. 11733492.0 Office Action dated Feb. 9, 2016.
European Office Action dated Oct. 16, 2014 for EP Application No. 06825389.7.
European office action dated Aug. 19, 2013 for EP Application No. 08796594.3.
European search report and search opinion dated Sep. 21, 2015 for EP Application No. 12854380.8.
European search report and search opinion dated Dec. 20, 2012 for EP Application No. 10754139.
European search report dated Mar. 1, 2013 for EP Application No. 10822810.7.
European search report dated Jul. 15, 2013 for EP Application No. 11733492.
Ferber, D. Bridging the blood-brain barrier: new methods improve the odds of getting drugs to the brain cells that need them. PLoS Biol. Jun. 2007;5(6):e169: 1191-1194.
Fillebeen, et al. Receptor-mediated transcytosis of lactoferrin through the blood-brain barrier. J Biol Chem. Mar. 12, 1999;274(11):7011-17.
Flomen, et al. Determination of the organisation of coding sequences within the iduronate sulphate sulphatase (IDS)gene. Hum. Mol. Genet. 1993;2(1):5-10.
Forough, et al. Differential transforming abilities of non-secreted and secreted forms of human fibroblast growth factor-1. J Biol Chem. Feb. 5, 1993;268(4):2960-8.
Fraldi, et al. Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Franco, et al. A cluster of sulfatase genes on Xp22.3: mutations in chondrodysplasia punctata (CDPX) and implications for warfarin embryopathy. Cell. Apr. 7, 1995;81(1):15-25.
Frenkel, et al. Modulation of Alzheimer's beta-amyloid neurotoxicity by site-directed single-chain antibody. J Neuroimmunol. Jul. 1, 2000;106(1-2):23-31.
Friden, et al. Blood-brain barrier penetration and in vivo activity of an NGF conjugate. Science. Jan. 15, 1993;259(5093):373-77.
Fu, et al. Neuroprotection in stroke in the mouse with intravenous erythropoietin—Trojan horse fusion protein. Brain Res. Jan. 19, 2011;1369:203-7. Epub Oct. 31, 2010.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Gehrmann, et al. Biochemical properties of recombinant human beta-glucuronidase synthesized in baby hamster kidney cells. Biochem J. Aug. 1, 1994;301 ( Pt 3):821-8.
Gennaro, 2000. Remington: The Science and Practice of Pharmacy. 20 ed. (WAS: Remington's Pharmaceutical Sciences, Gennaro, AR, ed., 20th edition, 2000: Williams and Wilkins PA, USA).
Gillies, et al. Bi-functional cytokine fusion proteins for gene therapy and antibody-targeted tratment of cancer. 2002, Cancer Immunology and Immunotherapy, vol. 51, pp. 449-460.
Golden, et al. Human blood-brain barrier leptin receptor. Binding and endocytosis in isolated human brain microvessels. J Clin Invest. Jan. 1, 1997;99(1):14-8.
Gonzales, et al. Minimizing immunogenicity of the SDR-grafted humanized antibody CC49 by genetic manipulation of the framework residues. Mol Immunol. Oct. 2003;40(6):337-49.

(56) References Cited

OTHER PUBLICATIONS

Gonzales, et al. SDR grafting of a murine antibody using multiple human germline templates to minimize its immunogenicity. Mol Immunol. Jul. 2004;41(9):863-72.
Grasso, et al. Neuroprotection by erythropoietin administration after experimental traumatic brain injury. Brain Res. Nov. 28, 2007:1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003:18(7):2093-8.
Habgood, et al. Changes in blood-brain barrier permeability to large and small molecules following traumatic brain injury in mice. Eur J Neurosci. Jan. 2007;25(1):231-8.
Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.
Hansson et al. Prediction of Alzheimer's disease using the CSF Abeta42/Abeta40 ratio in patients with mild cognitive impairment. Dement Geriatr Cogn Disord. 2007;23(5):316-20.
He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.
He, et al. Glial cell line-derived neurotrophic factor mediates the desirable actions of the anti-addiction drug ibogaine against alcohol consumption. J Neurosci. Jan. 19, 2005;25(3):619-28.
He, et al. Identification and characterization of the molecular lesion causing mucopolysaccharidosis type I in cats. Mol Genet Metab. 1999; 67(2):106-12.
Henikoff, et al. Amino acid substitution matrices from protein blocks. Proc Natl Acad Sci U S A. 1992; 89(22):10915-9.
Henikoff, et al. Predicting the effects of amino Acid substitutions on protein function. Annu Rev Genomics Hum Genet. 2006;7:61-80.
Hetman, et al. Neuroprotection by Brain-derived Neurotropic Factor Is Mediated by Extracellular Signal-regulated Kinase and Phoshatidylinositol 3-Kinase. The J of Bio Chem. 1999. 274 (32): 22569-80.
Holliger, et al. Engineered antibody fragments and the rise of single domains. Nat Biotechnol. Sep. 2005;23(9):1126-36.
Hoshaw, et al. Central administration of IGF-I and BDNF leads to long-lasting antidepressant-like effects. Brain Res. 2005. 1037: 204-8.
Hui et al., "Tumor Necrosis Factor Receptor-IgG Fusion Protein for Targeted Drug Delivery across the Human Blood-Brain Barrier," Mol. Pharm. vol. 6, No. 5, pp. 1536-1543 (2009).
Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.
Ibanez, et al. An extended surface of binding to Trk tyrosine kinase receptors in NGF and BDNF allows the engineering of a multi-functional pan-neurotrophin. EMBO J. Jun. 1993;12(6):2281-93.
Ibanez, Structure-function relationships in the neurotrophin family. J Neurobiol. Nov. 1994;25(11):1349-61.
International Preliminary Report on Patentability and Written Opinioin dated Jan. 26, 2016 in PCT/US2014/038660.
International Preliminary Report on Patentability and Written Opinion for International Application No. PCT/US2014/047082 dated Jan. 19, 2016.
International Preliminary Report on Patentability dated Jun. 1, 2010 for PCT/US2008/084718.
International search report and written opinion dated Feb. 22, 2011 for PCT/US2010/052113.
International search report and written opinion dated Feb. 22, 2013 for PCT/US2012/054520.
International search report and written opinion dated Feb. 27, 2009 for PCT/US2008/071121.
International search report and written opinion dated Apr. 8, 2011 for PCT/US2011/21418.
International search report and written opinion dated Jul. 1, 2008 for PCT/US2006/038587.
International search report and written opinion dated Sep. 7, 2010 for PCT/US2010/027882.
International search report and written opinion dated Sep. 16, 2008 for PCT/US2007/076316.
International search report and written opinion dated Oct. 29, 2014 for PCT/US2014/038660.
International search report and written opinion dated Dec. 15, 2014 for PCT Application No. PCT/US2014/047082.
Iwasaki, et al. Protective effect of interleukin-3 and erythropoietin on motor neuron death after neonatal axotomy. Neurol Res. Oct. 2002;24(7):643-6.
Japanese Patent Application No. 2014-116085 Office Action dated Jan. 19, 2016.
Jefferies, et al. Analysis of lymphopoietic stem cells with a monoclonal antibody to the rat transferrin receptor. Immunology. Feb. 1985;54(2):333-41.
Jeffrey, et al. 26-10 Fab-digoxin complex: Affinity and specificity due to surface complementarity. Proc Natl. Acad. Sci USA. 1993; 90(21):10310-10314.
Jethwa, et al. 2004. Neuromedin U has a physiological role in the regulation of food intake and partially mediates the effects of leptin. American Journal of Physiology—Endocrinology and Metabolism 289: E301-E305.
Jiang, et al. BDNF Variation and Mood Disorders: A Novel Functional Promoter Polymorphism and Val66Met are Associated with Anxiety but Have Opposing Effects. 2005. Neuropsychopharmacology 30:1353-61.
Jiang, et al. A genetic fusion construct between the tetanus toxin C fragment and the lysosomal acid hydrolase beta-glucuronidase expresses a bifunctional protein with enhanced secretion and neuronal uptake. J Neurochem. Jun. 2005;93(5):1334-44.
Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.
Josse, et al. Identification of residues essential for human paraoxonase (PON1) arylesterase/organophosphatase activities. Biochemistry. Mar. 2, 1999;38(9):2816-25.
Josse, et al. Oligomeric states of the detergent-solubilized human serum paraoxonase (PON1). J Biol Chem. Sep. 6, 2002;277(36):33386-97.
Josse, et al. The active site of human paraoxonase (PON1). J Appl Toxicol. Dec. 2001;21 Suppl 1:S7-11.
Juul, et al. Erythropoietin concentrations in cerebrospinal fluid of nonhuman primates and fetal sheep following high-dose recombinant erythropoietin, Biol. Neonate. 2004;85:138-144.
Kabat, et al., Sequences of Proteins of Immunological Interest. 5th Ed. Public Health Service, National Institutes of Health, Bethesda, Md. 1991;pp. 647-649.
Kakkis, et al. Intrathecal enzyme replacement therapy reduces lysosomal storage in the brain and meninges of the canine model of MPS I. Mol Genet Metab. Sep.-Oct. 2004;83(1-2):163-74.
Kakkis, et al. Overexpression of the human lysosomal enzyme alpha-L-iduronidase in Chinese hamster ovary cells. Protein Expr Purif. 1994; 5(3):225-32.
Karlin, et al. Applications and statistics for multiple high-scoring segments in molecular sequences. Proc. Natl. Acad. Sci. USA. 1993;90:5873-87.
Kashmiri, et al. SDR grafting—a new approach to antibody humanization. Methods. May 2005;36(1):25-34.
Kastin, et al. Glial cell line-derived neurotrophic factor does not enter normal mouse brain. Neuroscience Letters. 2003;340:239-41.
Kido, et al. 2000. Neuroprotective effects of brain-derived neurotropic factor in eyes with NMDA-induced neuronal death. Brain Research 884:59-67.
Kim, et al., Continuous Brain-derived Neurotropic Factor (BDNF) Infusion After Methylprednisolone Treatment in Severe Spinal Cord Injury. Journal of Korean Medical Science 2004;19: 113-22.

(56) References Cited

OTHER PUBLICATIONS

Kim, et al. Decreased paraoxonase-1 activity is a risk factor for ischemic stroke in Koreans. Biochem Biophys Res Commun. Dec. 7, 2007;364(1):157-62.

Kim, et al. N-terminal domains of native multidomain proteins have the potential to assist de novo folding of their downstream domains in vivo by acting as solubility enhancers. Protein Sci. Apr. 2007;16(4):635-43.

Kitagawa, et al. Reduction of Ischemic Brain Injury by Topical Application of Glial Cell Line-Derived Neurotrophic Factor After Permanent Middle Cerebral Artery Occlusion in Rats. Stroke. 1998;29:1417-22.

Knaust, "Residues Critical for Formylglycine Formation and/or Catalytic Activity of Arylsulfatase A," Biochemistry, 37:13941-13946 (1998).

Kobayashi, et al. Intracerebral Infusion of Glial Cell Line-Derived Neurotrophic Factor Promotes Striatal Neurogenesis After Stroke in Adult Rats Stroke. 2006;37:2361-67.

Koehne, et al. Vascular endothelial growth factor and erythropoietin concentrations in cerebrospinal fluid of children with hydrocephalus. Childs Nerv Syst. Apr. 2002;18(3-4):137-41.

Krewson, et al. Distribution of nerve growth factor following direct delivery to brain interstitium. Brain Research 680: 196-206 (1995).

Kurihara, et al. Imaging Brain Tumors by Targeting Peptide Radiopharmaceuticals through the Blood-Brain Barrier. Cancer Research 59: 6159-63 (1999).

Lai, et al. Structural determinants of Trk receptor specificities using BDNF-based neurotrophin chimeras. J Neurosci Res. Dec. 1, 1996;46(5):618-29.

Lang, et al. Randomized controlled trial of intraputamenal glial cell line-derived neurotrophic factor infusion in Parkinson disease. Annals of Neurology. 2006;59:459-66.

Lapchak, et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.

Lappi, et al. Expression and activities of a recombinant basic fibroblast growth factor-saporin fusion protein. J Biol Chem. Apr. 29, 1994;269(17):12552-8.

Lazar, et al. Transforming growth factor alpha: mutation of aspartic acid 47 and leucine 48 results in different biological activities. Mol Cell Biol. Mar. 1988;8(3):1247-52.

Lee, et al. Drug targeting to the brain using avidin-biotin technology in the mouse; (blood-brain barrier, monoclonal antibody, transferrin receptor, Alzheimer's disease). J Drug Target. 2000;8(6):413-24.

Lee, et al., Imaging Brain Amyloid of Alzheimer Disease In Vivo in Transgenic Mice with an Aβ Peptide Radiopharmaceutical. Journal of Cerebral Blood Flow and Metabolism 2002;22: 223-31.

Lenz, et al. Stoichiometric and catalytic scavengers as protection against nerve agent toxicity: a mini review. Toxicology. Apr. 20, 2007;233(1-3):31-9.

Lewin, B. Genes IV. Oxford University Press. 1990. p. 810.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Lin, et al. GDNF: a glial cell line-derived neurotrophic factor for midbrain dopaminergic neurons. Science. 1993;260:1130-32.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Liu, et al. Anti beta-amyloid (Abeta) SCFV inhibits Abeta aggregation and neurotoxicity (P4-354). Neurobiology of Aging, Tarrytown, NY. 2004;25:S575-S576.

Liu, et al. Single chain variable fragments against beta-amyloid (Abeta) can inhibit Abeta aggregation and prevent abeta-induced neurotoxicity. Biochemistry. Jun. 8, 2004;43(22):6959-67.

Lu, et al. Cationic Liposome-Mediated GDNF Gene Transfer after Spinal Cord Injury. Journal of Neurotrauma. 2002;19:1081-1090.

Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).

Lu et al., "Genetic Engineering of a Bifunctional IgG fusion protein with iduronate-2-sulfatase," Bioconjugate Chemistry, 21(1) pp. 151-156 (2010).

Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

MacCallum, et al. Antibody-antigen interactions: contact analysis and binding site topography. J Mol Biol. Oct. 11, 1996;262(5):732-45.

Manoutcharian, et al. Amyloid-beta peptide-specific single chain Fv antibodies isolated from an immune phage display library. J Neuroimmunol. 2003; 145(1-2):12-7.

Martell, et al. Efficacy of transferrin receptor-targeted immunotoxins in brain tumor cell lines and pediatric brain tumors. Cancer Res. Mar. 15, 1993;53(6):1348-53.

Martin et al. Crystal structure at 2.8 A of an FcRn/heterodimeric Fc complex: mechanism of pH-dependent binding. Mol Cell. Apr. 2001;7(4):867-77.

Marvin, et al. Recombinant approaches to IgG-like bispecific antibodies. Acta Pharmacol Sin. Jun. 2005;26(6):649-58.

Matis, et al. Erythropoietin in spinal cord injury. Eur Spine J. Mar. 2009;18(3):314-23.

McGrath, et al. Bifunctional fusion between nerve growth factor and a transferrin receptor antibody. J Neurosci Res. Jan. 15, 1997;47(2):123-33.

McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.

Menzies, et al. Contributions of ions and albumin to the formations and resolution of ischemic brain edema. Journal of Neurosurgery 78: 257-266. (1993).

Messer, et al. Role for GDNF in biochemical and behavioral adaptations to drugs of abuse. Neuron. Apr. 2000;26(1):247-57.

Moos, et al. Restricted transport of anti-transferrin receptor antibody (OX26) through the blood-brain barrier in the rat. J Neurochem. Oct. 2001;79(1):119-29.

Mori, et al. Differential expression patterns of TrkB ligands in the macaque monkey brain. Developmental Neuroscience 15: 2507-11 (2004).

Morita, et al. Association of tumor necrosis factor receptor type II polymorphism 196R with Systemic lupus erythematosus in the Japanese: molecular and functional analysis. Arthritis Rheum. Dec. 2001;44(12):2819-27.

Muenzer, et al. A phase II/III clinical study of enzyme replacement therapy with idursulfase in mucopolysaccharidosis II (Hunter syndrome). Genet Med Aug. 2006;8(8):465-73.

Muenzer, et al. Advances in the treatment of mucopolysaccharidosis type I. N Engl J Med. May 6, 2004;350(19):1932-4.

Nawashiro et al., "Neuroprotective effects of TNF binding protein in focal cerebral ischemia," Brain Research, vol. 778, No. 2, pp. 265-271 (1997).

NCBI GenBank Accession No. NM-000487 (Oct. 23, 2011).

NCBI Reference Sequence: NM-000202.5 *Homo sapiens* iduronate 2-sulfatase (IDS), transcript variant 1, mRNA. 1992. http://www.ncbi.nlm.nih.gov/nuccore/NM000202.5.

Needleman, et al. A general method applicable to the search for similarities in the amino acid sequence of two proteins. J. Mol. Biol. 1970;48:443-53.

Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.

(56) References Cited

OTHER PUBLICATIONS

Ng, et al. Predicting the effects of amino acid substitutions on protein function. Annual Review of Genomics and Human Genetics. 2006;7:61-80.
Notice of allowance dated Jan. 22, 2014 for U.S. Appl. No. 12/323,232.
Notice of allowance dated Jan. 28, 2010 for U.S. Appl. No. 11/841,623.
Notice of Allowance dated Mar. 20, 2013 for U.S. Appl. No. 13/609,099.
Notice of allowance dated Apr. 1, 2011 for U.S. Appl. No. 11/245,546.
Notice of Allowance dated Apr. 2, 2013 for U.S. Appl. No. 11/841,594.
Notice of allowance dated May 20, 2014 for U.S. Appl. No. 12/901,481.
Notice of allowance dated Aug. 9, 2011 for U.S. Appl. No. 11/245,710.
Notice of allowance dated Aug. 12, 2014 for U.S. Appl. No. 14/194,463.
Notice of allowance dated Sep. 23, 2013 for U.S. Appl. No. 12/756,093.
Notice of allowance dated Sep. 25, 2013 for U.S. Appl. No. 13/862,250.
Notice of allowance dated Oct. 7, 2013 for U.S. Appl. No. 12/323,232.
Notice of allowance dated Oct. 28, 2011 for U.S. Appl. No. 12/688,842.
Notice of allowance dated Oct. 31, 2011 for U.S. Appl. No. 11/245,546.
Notice of allowance dated Dec. 13, 2013 for U.S. Appl. No. 13/862,250.
Notice of allowance dated Dec. 16, 2013 for U.S. Appl. No. 12/756,093.
Notice of allowance dated Dec. 19, 2014 for U.S. Appl. No. 12/179,806.
Notice of allowance dated Dec. 23, 2013 for U.S. Appl. No. 11/841,541.
Nutt, et al., Randomized, double-blind trial of glial cell line-derived neurotropic factor (GDNF) in PD. Neurology 2003;60: 69-73.
Ober, et al. Differences in promiscuity for antibody-FcRn interactions across species: implications for therapeutic antibodies. Int Immunol. Dec. 2001;13(12):1551-9.
Office action dated Jan. 9, 2013 for U.S. Appl. No. 12/901,481.
Office action dated Jan. 15, 2008 for U.S. Appl. No. 11/245,710.
Office action dated Jan. 15, 2009 for U.S. Appl. No. 11/841,623.
Office action dated Jan. 23, 2009 for U.S. Appl. No. 11/245,546.
Office action dated Feb. 2, 2010 for U.S. Appl. No. 11/245,710.
Office action dated Feb. 10, 2006 for U.S. Appl. No. 10/307,165.
Office action dated Feb. 16, 2011 for U.S. Appl. No. 11/893,281.
Office action dated Feb. 16, 2011 for U.S. Appl. No. 12/150,983.
Office action dated Feb. 22, 2006 for U.S. Appl. No. 10/307,276.
Office action dated Mar. 1, 2007 for U.S. Appl. No. 10/307,165.
Office action dated Mar. 7, 2011 for U.S. Appl. No. 12/558,348.
Office action dated Mar. 10, 2010 for U.S. Appl. No. 12/179,806.
Office action dated Mar. 18, 2011 for U.S. Appl. No. 12/574,571.
Office action dated Mar. 26, 2010 for U.S. Appl. No. 11/841,594.
Office action dated Mar. 26, 2010 for U.S. Appl. No. 12/323,232.
Office action dated Apr. 6, 2011 for U.S. Appl. No. 11/245,710.
Office action dated Apr. 8, 2014 for U.S. Appl. No. 13/141,682.
Office action dated Apr. 9, 2007 for U.S. Appl. No. 10/307,276.
Office action dated Apr. 13, 2007 for U.S. Appl. No. 11/245,710.
Office action dated Apr. 24, 2013 for U.S. Appl. No. 12/179,806.
Office action dated May 6, 2014 for U.S. Appl. No. 14/144,460.
Office action dated May 6, 2015 for U.S. Appl. No. 14/281,803.
Office action dated May 9, 2008 for U.S. Appl. No. 11/061,956.
Office action dated May 12, 2010 for U.S. Appl. No. 11/893,281.
Office action dated May 13, 2011 for U.S. Appl. No. 12/688,842.
"Office action dated May 19, 2015 for U.S. Appl. No. 13/141,682.".
Office action dated May 23, 2006 for U.S. Appl. No. 11/061,956.
Office action dated Jun. 3, 2008 for U.S. Appl. No. 11/245,710.
Office action dated Jun. 17, 2009 for U.S. Appl. No. 11/841,541.
Office action dated Jun. 27, 2011 for U.S. Appl. No. 11/245,546.
Office action dated Jun. 30, 2014 for U.S. Appl. No. 12/179,806.
Office action dated Jul. 1, 2010 for U.S. Appl. No. 11/245,546.
Office action dated Jul. 2, 2008 for U.S. Appl. No. 11/245,546.
Office action dated Jul. 2, 2009 for U.S. Appl. No. 11/245,710.
"Office action dated Jul. 17, 2015 for U.S. Appl. No. 14/192,792.".
Office action dated Jul. 19, 2006 for U.S. Appl. No. 10/307,276.
Office action dated Jul. 20, 2012 for U.S. Appl. No. 12/756,093.
Office action dated Jul. 31, 2009 for U.S. Appl. No. 12/179,806.
Office action dated Aug. 15, 2013 for U.S. Appl. No. 13/141,682.
Office action dated Aug. 17, 2007 for U.S. Appl. No. 10/307,165.
Office action dated Aug. 18, 2006 for U.S. Appl. No. 10/307,165.
Office action dated Aug. 20, 2009 for U.S. Appl. No. 12/323,232.
Office action dated Aug. 26, 2015 for U.S. Appl. No. 14/594,047.
Office action dated Sep. 15, 2010 for U.S. Appl. No. 12/150,983.
Office action dated Sep. 20, 2007 for U.S. Appl. No. 11/245,710.
Office action dated Sep. 24, 2009 for U.S. Appl. No. 11/841,623.
Office action dated Oct. 12, 2010 for U.S. Appl. No. 11/245,710.
Office action dated Oct. 13, 2009 for U.S. Appl. No. 11/893,281.
Office action dated Oct. 15, 2007 for U.S. Appl. No. 11/245,710.
Office action dated Oct. 18, 2011 for U.S. Appl. No. 11/245,546.
Office action dated Oct. 20, 2009 for U.S. Appl. No. 11/245,546.
Office action dated Oct. 20, 2014 for U.S. Appl. No. 13/141,682.
Office action dated Oct. 22, 2013 for U.S. Appl. No. 12/901,481.
Office action dated Oct. 29, 2007 for U.S. Appl. No. 10/307,276.
Office action dated Oct. 30, 2009 for U.S. Appl. No. 11/841,594.
Office action dated Nov. 1, 2012 for U.S. Appl. No. 11/841,594.
Office action dated Nov. 4, 2013 for U.S. Appl. No. 12/179,806.
Office action dated Nov. 8, 2007 for U.S. Appl. No. 11/245,546.
Office action dated Nov. 10, 2008 for U.S. Appl. No. 11/245,710.
Office action dated Nov. 13, 2006 for U.S. Appl. No. 11/245,710.
Office action dated Nov. 13, 2007 for U.S. Appl. No. 11/061,956.
Office action dated Nov. 26, 2012 for U.S. Appl. No. 13/609,099.
Office action dated Nov. 26, 2014 for U.S. Appl. No. 14/144,460.
Office action dated Dec. 14, 2011 for U.S. Appl. No. 12/574,571.
Office action dated Dec. 16, 2009 for U.S. Appl. No. 11/841,541.
Office action dated Dec. 21, 2006 for U.S. Appl. No. 11/061,956.
Office action dated Mar. 26, 2013 for U.S. Appl. No. 11/841,541.
Ohtsuka, et al. An alternative approach to deoxyoligonucleotides as hybridization probes by insertion of Deoxyinosine at Ambiguous Codon Positions. J. Biol. Chem. 1985;260:2605-08.
Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Osbourn, et al. Directed selection of MIP-1 alpha neutralizing CCR5 antibodies from a phage display human antibody library. Nat Biotechnol. Aug. 1998;16(8):778-81.
Padlan, et al. Identification of specificity-determining residues in antibodies. FASEB J. 1995; 9(1):133-9.
Padlan, et al. Structure of an antibody-antigen complex: crystal structure of the HyHEL-10 Fab-lysozyme complex. Proc Natl Acad Sci U S A. Aug. 1989;86(15):5938-42.
Paragh, et al. Ciprofibrate increases paraoxonase activity in patients with metabolic syndrome. Br J Clin Pharmacol. Jun. 2006;61(6):694-701.
Pardridge, Biopharmaceutical drug targeting to the brain. Journal of Drug Targeting, 18(3): 157-167 (2010).
Pardridge, The Blood-Brain Barrier: Bottleneck in Brain Drug Development. NeuroRx: The Journal of the American Society for Experimental NeuroTherapeutics 2: 3-14 (2005).
Pardridge. "Blood-brain barrier delivery of protein and non-viral gene therapeutics with molecular Trojan horses," Journal of Controlled Release, vol. 122, No. 3, pp. 345-348 (2007).
Pardridge, Blood-Brain Barrier Drug Targeting: The Future of Brain Drug Development. Molecular Interventions 3: 90-105 (2003).
Pardridge, Brain drug targeting: The future of brain drug development. Cambridge University Press (2001).
Pardridge, Drug Targeting to the Brain. Pharm Res 24:1733-44 (2007).
Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).

(56) References Cited

OTHER PUBLICATIONS

Pardridge et al., "Biologic TNF[alpha]-inhibitors that cross the human blood-brain barrier," Bioengineered Bugs. vol. 1, No. 4, pp. 231-234 (2010).
Pardridge, et al. Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582 (1998).
Pardridge, et al. Drug and gene targeting to the brain with molecular Trojan horses. Nat Rev Drug Discov., Feb;1(2):131-9 (2002).
Pardridge, et al. Human Blood-Brain Barrier Transferrin Receptor. Metabolism 36: 892-95 (1987).
Pardridge, et al. Transport of histone through the blood-brain barrier. J Pharmacol Exp Ther. Dec;251(3):821-6. (1989).
Pardridge, et al. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46 (1994).
Pardridge, Neuroprotection in stroke: is it time to consider large-molecule drugs? Drug Discovery Today 6: 751-53 (2001).
Pardridge, Neurotrophins, neuroprotection and the blood-brain barrier. Current Opinion in Investigational Drugs 3 (12): 1753-57 (2002).
Pardridge, "Re-engineering biopharmaceuticals for delivery to brain with molecular Trojan horses," Bioconjugate Chemistry, vol. 19, No. 7, pp. 1327-1338 (2008).
Pardridge, The Blood-Brain Barrier and Neurotherapeutics. NeuroRx: The Journal of the American Society for Experimental NeuroTherapeutics 2 (1): 1-2 (2005).
Pardridge, Tyrosine Hydroxylase Replacement in Experimental Parkinson's Disease with Transvascular Gene Therapy. NueuoRx: Journal of the American Society for Experimental NeuroTherapeutics. 2(1):129-138. (2005).
Park, et al. Production and characterization of fusion proteins containing transferrin and nerve growth factor. J Drug Target. 1998;6(1):53-64.
Patel, et al. Intraputamenal infusion of glial cell line-derived neurotrophic factor in PD: A two-year outcome study. Annals of Neurology. 2005;57:298-302.
Paul, W. Fundamental Immunology. 3rd Edition. 1993; 292-95.
Pearson, et al. Improved Tools for Biological Sequence Comparison. Proc. Nat'l Acad. Sci. USA. 1988;85:2444-48.
Pearson, Rapid and sensitive sequence comparison with FASTP and FASTA. Meth. Enzymol. 1990;183:63-98.
Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.
Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-26.
Peppel; et al., "A tumor necrosis factor (TNF) receptor-IgG heavy chain chimeric protein as a bivalent antagonist of TNF activity.", Dec. 1, 1991, 174(6), 1483-9.
Pluckthun, A. Antibodies from *Escherichia coli*. In the Pharmacology of Monoclonal Antibodies. vol. 113, Rosenburg and Moore eds. Springer-Verlag, New York. 1994;pp. 269-315.
Polito et al., "IDS Crossing of the Blood-Brain Barrier Corrects CNS Defects in MPSII Mice," Amer. Journ. Human Genetics, vol. 85, No. 2, pp. 296-301 (2009).
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Preston, et al. 1997. Evidence for pore-like opening of the blood-brain barrier following forebrain ischemia in rats. Brain Research 761: 4-10.
Prince, et al. Lipoprotein receptor binding, cellular uptake, and lysosomal delivery of fusions between the receptor-associated protein (RAP) and alpha-L-iduronidase or acid alpha-glucosidase. J Biol Chem. Aug. 13, 2004;279(33):35037-46. Epub May 31, 2004.
Qi, et al. Binding and cytotoxicity of conjugated and recombinant fusion proteins targeted to the gonadotropin-releasing hormone receptor. Cancer Res. Mar. 15, 2004;64(6):2090-5.
Raghavan, et al. Analysis of the pH dependence of the neonatal Fc receptor/immunoglobulin G interaction using antibody and receptor variants. Biochemistry. Nov. 14, 1995;34(45):14649-57.
Ratliff-Schaub, et al. 2005. Randomized controlled trial of transdermal secretion on behavior of children with autism. Autism 9 (3): 256-65.
Reiber, et al. Protein transfer at the blood cerebrospinal fluid barrier and the quantitation of the humoral immune response within the central nervous system. Clin Chim Acta. Mar. 30, 1987;163(3):319-28.
Rempel, et al. A homology model for human α-L-Iduronidase: Insights into human disease. Mol. Genetics and Met. 2005; 85:28-37.
Robinson, et al. The structures of the neurotrophin 4 homodimer and the brain-derived neurotrophic factor / neurotrophin 4 heterodimer reveal a common Trk-binding site. Protein Science 1999 8: 2589-97.
Rochu, et al. Human paraoxonase: a promising approach for pretreatment and therapy of organophosphorus poisoning. Toxicology. Apr. 20, 2007;233(1-3):47-59.
Rohrback, et al. Therapeutic antibodies and antibody fusion proteins. Biotechnol Genet Eng Rev. 2003;20:137-63.
Rossolini, et al. Use of deoxyinosine-containing primers vs degenerate primers for polymerase chain reaction based on ambiguous sequence information. Mol. Cell. Probes. 1994;8(2):91-98.
Rudikoff, et al. Single amino acid substitution altering antigen-binding specificity. Proc Natl Acad Sci U S A. Mar. 1982;79(6):1979-83.
Ruiz-Leon, et al. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120;2003:1019-26.
Ruth, et al. alpha-L-iduronidase forms semi-crystalline spherulites with amyloid-like properties. Acta Crystallogr D Biol Crystallogr. Apr. 2000;56(Pt 4):524-8.
Rybak, et al. Humanization of immunotoxins. Proc Natl Acad Sci U S A. Apr. 15, 1992;89(8):3165-9.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.
Sampson et al. Unarmed, tumor-specific monoclonal antibody effectively treats brain tumors. Proc Natl Acad Sci U S A. Jun. 20, 2000;97(13):7503-8.
Sardiello, et al. Sulfatases and sulfatase modifying factors: an exclusive and promiscuous relationship. Hum Mol Genet. Nov. 1, 2005;14(21):3203-17. Epub Sep. 20, 2005.
Sariola, et al. Novel functions and signalling pathways for GDNF. J Cell Sci. Oct. 1, 2003;116(Pt 19):3855-62.
Scallon, et al. Functional comparisons of different tumour necrosis factor receptor/IgG fusion proteins. Cytokine. Nov. 1995;7(8):759-70.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Expression of the neonatal Fc receptor (FcRn) at the blood-brain barrier. J Neurochem. Apr. 2002;81(1):203-6.
Schlachetzki, et al. Gene therapy of the brain: the trans-vascular approach. Neurology. Apr. 27, 2004;62(8):1275-81.
Schoonjans, R. et al., "Fab Chains as an Efficient Heterodimerization Scaffold for the Production of Recombinant Bispecific and Trispecific Antibody Derivatives." The Journal of Immunology, 2000, 165 (12): 7050-7057.
Schuchman, et al. Human alpha-L-iduronidase: Purification and properties of the high uptake (higher molecular weight) and the low uptake (processed) forms. J. Bioi. Chem. 1984; 259(5):3132-3140.

(56) References Cited

OTHER PUBLICATIONS

Schwartz, et al. A superactive insulin: [B10-aspartic acid]insulin(human). Proc Natl Acad Sci U S A. Sep. 1987;84(18):6408-11.
Scott, et al. Human alpha-L-iduronidase: cDNA isolation and expression. Proc Natl Acad Sci U S A. Nov. 1, 1991;88(21):9695-9.
Sellers, On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Shanafelt, et al. Identification of critical amino acid residues in human and mouse granulocyte-macrophage colony-stimulating factor and their involvement in species specificity. J Biol Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.
Shipley, et al. The role of glycosylation and phosphorylation in the expression of active human beta-glucuronidase. J Biol Chem. Jun. 5, 1993;268(16):12193-8.
Sifuentes, et al. A follow-up study of MPS I patients treated with laronidase enzyme replacement therapy for 6 years. Mol Genet Metab. Feb. 2007;90(2):171-80. Epub Sep. 29, 2006.
Siren, et al., Erythropoetin prevents neuronal apoptosis after cerebral ischemia and metabolic stress. Proc Natl Acad Sci U S A. Mar. 27, 2001;98(7):4044-9.
Sivakumur et al., Bone marrow transplantation in mucopolysaccharidosis type IIIA: A comparison of an early treated patient with his untreated sibling. J. Inher. Metab. Dis., 22(849):849-850 (1999).
Skolnick, et al. From genes to protein structure and function: novel applications of computational approaches in the genomic era. Trends Biotechnol. Jan. 2000;18(1):34-9. Review.
Smith, et al. Comparison of Biosequences. Adv. Appl. Math. 1981 1;482-89.
Soukharev, et al. A fluorogenic substrate for detection of organophosphatase activity. Anal Biochem. Apr. 1, 2004;327(1):140-8.
Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry1992;59 (1): 99-106.
Strauss, et al., Brain-derived neurotrophic factor variants are associated with childhood-onset mood disorder: confirmation in a Hungarian sample. Molecular Psychiartry 2005;10: 861-67.
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
Sumbria; et al., "Brain protection from stroke with intravenous TNFα decoy receptor—Trojan horse fusion protein", Oct. 2012, 32(10), 1933-8.
Takahashi, et al., Inhibition of cell growth and tumorigenesis of human glioblastoma cells by a neutralizing antibody against human basic fibroblast growth factor. Federation of European Biochemical Societies 1991;288 (1,2): 65-71.
The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.
Thompson, et al. Improved binding of a bivalent single-chain immunotoxin results in increased efficacy for in vivo T-cell depletion. Protein Eng. Dec. 2001;14(12):1035-41.
Tobinick et al., "Perispinal etanercept for neuroinflammatory disorders," Drug Discovery Today, vol. 14, No. 3-4, pp. 168-177 (2009).
Tomatsu, et al. Murine model (Galns(tm(C76S)slu)) of MPS IVA with missense mutation at the active site cystein conserved among sulfatase proteins. Mol Genet Metab. Jul. 2007;91(3):261-8.

Tougou, et al. Paraoxonase has a major role in the hydrolysis of prulifloxacin (NM441), a prodrug of a new antibacterial agent. Drug Metab Dispos. Apr. 1998;26(4):355-9.
Traunecker; et al., "Highly efficient neutralization of HIV with recombinant CD4-immunoglobulin molecules.", May 4, 1989,339(6219), 68-70.
Triguero et al. Capillary depletion method for quantification of blood-brain barrier transport of circulating peptides and plasma proteins. J Neurochem. 1990; 54(6):1882-8.
Tsukahara, et al. The Role of Brain-derived Neurotrophic Factor in Transient Forebrain Ischemia in the Rat Brain. Neurosurgery 34 (2);1994:323-31.
Tuma, et al. Transcytosis: crossing cellular barriers. Physiol Rev. Jul. 2003;83(3):871-932.
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Unger, et al. Recombinant α-iduronidase: characterization of the purified enzyme and correction of mucopolysaccharidosis type I fibroblasts. Biochem J. 1994; 384:43-49.
U.S. Appl. No. 13/141,682 Final Office Action dated Nov. 10, 2015.
U.S. Appl. No. 14/144,460, filed Dec. 30, 2013.
U.S. Appl. No. 14/144,460 Office Action dated Aug. 17, 2015.
U.S. Appl. No. 14/192,792, filed Feb. 27, 2014.
U.S. Appl. No. 14/192,792 Final Offic Action dated Oct. 30, 2015.
U.S. Appl. No. 14/194,463, filed Feb. 28, 2014.
U.S. Appl. No. 14/281,803, filed May 19, 2014.
U.S. Appl. No. 14/305,402, filed Jun. 16, 2014.
U.S. Appl. No. 14/538,721, filed Nov. 11, 2014.
U.S. Appl. No. 14/538,721 Office Action dated Dec. 3, 2015.
Voznyi, et al. A fluorimeteric enzyme assay for the diagnosis of MPS II (Hunter disease). J Inherit Metab Dis. 2001;24:675-80.
Wang, et al. Identification of the key amino acids of glial cell line-derived neurotrophic factor family receptor alpha1 involved in its biological function. J Biol Chem. Jan. 2, 2004;279(1):109-16.
Ward, E.S. Binding activities of a repertoire of single immunoglobulin variable domains secreted from Escherichia coli. Nature. Oct. 12, 1989;341(6242):484-5.
Warrington, et al. Human monoclonal antibodies reactive to oligodendrocytes promote remyelination in a model of multiple sclerosis. Proc Natl Acad Sci U S A. Jun. 6, 2000;97(12):6820-5.
Weich, et al. Interleukin-3/erythropoietin fusion proteins: in vitro effects on hematopoietic cells. Exp Hematol. May 1993;21(5):647-55.
Whetstone, et al. Blood-spinal cord barrier after spinal cord injury: relation to revascularization and wound healing. J Neurosci Res. Oct. 15, 2003;74(2):227-39.
Whittaker, et al. Characterization of the functional insulin binding epitopes of the full-length insulin receptor. J Biol Chem. 2005;280(22):20932-6.
Wiesenhofer, et al. Glial cell line-derived neurotrophic factor (GDNF) and its receptor (GFR-α1) are strongly expressed in human gliomas. Acta Neuropathol. (Berl). 2000;99:131-37.
Wraith, et al. Enzyme replacement therapy for mucopolysaccharidosis I: a randomized, double-blinded, placebo-controlled, multinational study of recombinant human alpha-L-iduronidase (laronidase). J Pediatr. May 2004;144(5):581-8.
Wraith, et al. Mucopolysaccaridosis type II (Hunter syndrome): a clinical review and recommendations for treatment in the era of enzyme replacement therapy. Eur J Pediatr. Mar. 2008;167(3):267-77.
Wraith, J. Enzyme replacement therapy in mucopolysaccharidosis type I: progress and emerging difficulties. J Inherit Metab Dis. Apr. 2001;24(2):245-50.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection in Experimental Stroke with Targeted Neurotrophins. NeuroRX: The Journal of the American Society for Experimental NeuroTherapeutics. 2005;2(1):120-128.

(56) References Cited

OTHER PUBLICATIONS

Wu, et al. Neuroprotection with noninvasive neurotrophin delivery to the brain. Proc Natl Acad Sci U S A. Jan. 5, 1999;96(1):254-9.
Wu, et al. Simultaneous targeting of multiple disease mediators by a dual-variable-domain immunoglobulin. Nat Biotechnol. Nov. 2007;25(11):1290-7. Epub Oct. 14, 2007.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12(4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.
Yan, et al. 2007 Enduring vulnerability to reinstatement of methamphetamine-seeking behavior in glial-cell-line-derived neurotrophic factor mutant mice. FASEB J. Jul;21(9):1994-2004.
Yip, et al. Three-dimensional structural interactions of insulin and its receptor. J Biol Chem. Jul. 25, 2003;278(30):27329-32.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2001. Rapid transferrin efflux from brain to blood across the blood-brain barrier. J Neurochem. Mar;76(5):1597-600.
Zhang, et al. 2003. Global Non-Viral Gene Transfer to the Primate Brain Following Intravenous Administration. Molecular Therapy 7 (1): 11-18.
Zhang, et al. Mediated efflux of IgG molecules from brain to blood across the blood-brain barrier. J Neuroimmunol. Mar. 1, 2001;114(1-2):168-72.
Zhao, et al. Carbohydrate structures of recombinant human alpha-L-iduronidase secreted by Chinese hamster ovary cells. J Biol Chem. Sep. 5, 1997;272(36):22758-65.
Zhou, et al. Brain penetrating IgG-erythropoietin fusion protein is neuroprotective following intravenous treatment in Parkinson's disease in the mouse. Brain Res. Mar. 25, 2011;1382:315-20. Epub Jan. 26, 2011.
Zhou; et al., "Neuroprotection with a brain-penetrating biologic tumor necrosis factor inhibitor.", Nov. 2011, 339(2), 618-23.
Zhou, et all. Brain-penetrating IgG-iduronate 2-sulfatase fusion protein for the mouse. Drug Metab Dispos. Feb. 2012;40(2):329-35. doi: 10.1124/dmd.111.042903. Epub Nov. 7, 2011.
Zito, et al. Sulphatase activities are regulated by the interaction of sulphatase-modifying factor 1 with SUMF2, EMBO Rep 2005;6(7):655-660.
Australian Patent Application No. 2012346448 dated Sep. 8, 2016.
Canadian Patent Application No. 2,748,889 Office Action dated Oct. 19, 2016.
Cheng, SH et al. Gene therapy progress and prospects: gene therapy of lysosomal storage disorders, Gene Therapy 10:1275-1281 (2003).
European Application No. 16171496 Extended European Search Report dated Oct. 31, 2016.
European Application No. 16171496.9 Extended European Search Report dated Feb. 10, 2017.
Gardner, CJ et al. Growth, final height and endocrine sequelae in a UK population of patients with Hurler syndrome (MPS1H). J. Inherit Metab Dis. 34(2):489-97 (Apr. 2011).
Japanese Patent Application No. 2014116085 Office Action dated Aug. 3, 2016.
Kim et al. Protective effects of glial cell line-derived neurotrophic factor on hippocampal neurons after traumatic brain injury in rats. Journal of Neurosurgery 95:674-679 (2001).

Padridge, William M. Blood-brain drug targeting enables neuroprotection in brain ischemia following delayed intravenous administration of neurothrophins, Advances in Experimental Medicine and Biology, 543:397-430 (Jan. 1, 2002).
Sidhu, Navdeep S. Structure of sulfamidase provides insight into the molecular pathology of mucopolysaccharidosis IIIA. Acta Cryst. (2014). D70, 1321-1335.
Sun et al. Comparison of the capability of GDNF, BDNF, or both, to protect nigrostriatal neurons in a rat model of Parkinson's disease. Brain Research 1052(2);119-29 (Aug. 9, 2005).
U.S. Appl. No. 14/144,460 Final Office Action dated Nov. 9, 2016.
U.S. Appl. No. 14/192,792 Office Action dated Apr. 14, 2017.
U.S. Appl. No. 14/281,803 Final Office Action dated Apr. 28, 2017.
U.S. Appl. No. 14/305,402 Non-Final Office Action dated Jul. 6, 2017.
"U.S. Appl. No. 14/305,402 Office Action dated Jan. 3, 2017".
U.S. Appl. No. 14/538,721 Non-Final Office Action dated Apr. 13, 2017.
U.S. Appl. No. 14/594,047 Office Action dated Jan. 18, 2017.
U.S. Appl. No. 14/906,259 Non-final Office Action dated May 4, 2017.
U.S. Appl. No. 14/994,067 Non-Final Office Action dated Jan. 17, 2017.
U.S. Appl. No. 14/538,721 Office Action dated Sep. 8, 2016.
U.S. Appl. No. 14/594,047 Advisory Office Action dated Oct. 17, 2016.
U.S. Appl. No. 14/606,239 Notice of Allowability dated Oct. 21, 2016.
U.S. Appl. No. 14/606,239 Notice of Allowance dated Oct. 3, 2016.
Vahabzadeh, A. et al. Effects of changes in rat brain glucose on serotonergic and noradrenergic neurons. Eur. J. Neurosci. 7(2):175-9 (Feb. 1, 1995) Abstract Only.
Xenocostas, Anargyros et al., The pharmacokinetics of erythropoietin in the cerebrospinal fluid after intravenous administration of recombinant human erythropoietin. European Journal of Clinical Pharmacology, 61(3): 189-195 (Mar. 2005).
Hasselbalch, Steen G. et al. No Effect of Insulin on Glucose Blood-Brain Barrier Transport and Cerebral Metabolism in Humans, Diabetes, 48:1915-1921 (Oct. 1999).
Olson, et al. Role of growth factors in degeneration and regeneration in the central nervous system; clinical experiences with NGF in Parkinson's and Alzheimer's diseases. J. Neurol. 241:S12-S15 (1994).
Udupa, KB. Functional significance of erythropoietin receptor on tumor cells. World J. Gastroenterol. 12(46):7460-7462 (Dec. 14, 2006).
U.S. Appl. No. 14/144,460 Non-Final Office Action dated Apr. 4, 2018.
U.S. Appl. No. 14/192,792 Non-Final Office Action dated Feb. 20, 2018.
U.S. Appl. No. 14/281,803 Non-Final Office Action dated Nov. 16, 2017.
U.S. Appl. No. 14/305,402 Notice of Allowance dated Feb. 28, 2018.
U.S. Appl. No. 14/538,721 Notice of Allowance dated Jan. 23, 2018.
U.S. Appl. No. 14/594,047 Final Office Action dated Oct. 18, 2017.
U.S. Appl. No. 15/397,649 Non-Final Office Action dated Mar. 1, 2018.
Australian Application No. 2013206657 Examination Report dated Apr. 25, 2016.
Biffi, A. et al. Correction of metachromatic leukodystrophy in the mouse model by transplantation of genetically modified hematopoietic stem cells. J. Clin. Invest., 113(8); p. 1118-1129 (2004).
Canadian Application No. 2,694,762 Office Action dated Apr. 7, 2016.
Chudler, Eric H.Brain Facts and Figures, from Eric H. Chudler's Neuroscience for Kids: faculty.washington.edu/chudler/facts.html. Retrieved from Internet on Jun. 6, 2016, 14 pages.
Japanese Application No. 2011-23913 Office Action dated Feb. 23, 2016.
Japanese Application No. 2014-043117 Office Action dated Apr. 7, 2016.

(56) References Cited

OTHER PUBLICATIONS

Japanese Application No. 2014544731 Office Action dated Jun. 14, 2016.
Kurbacher, et al. Continuous Low-Dose GM-CSF as Salvage Therapy in Refractory Recurrent Breast or Female Genital Tract Carcinoma. Oncology, 19(4) Supp 2: Apr. 23-26, 2005.
Pardridge, et al. Drug Transport across the blood-brain barrier. Journal of Cerebral Blood Flow & Metabolism. 32; 1959-1972(2012).
Sevin, C. et al. Intracerebral adeno-associated virus-mediated gene transfer in rapidly progressive forms of metachromatic leukodystrophy. Human Molecular Genetics 15(1); 53-64 (2006).
Stroobants, S. et al. Intracerebroventricular enzyme infusion corrects central nervous system pathology and dysfunction in a mouse model of metachromatic leukodystrophy. Human Molecular Genetics 20(4); 2760-2769 (2011).
U.S. Appl. No. 13/141,682 Non-Final Office Action dated Mar. 30, 2016.
U.S. Appl. No. 14/144,460 Non-Final Office Action dated Apr. 21, 2016.
U.S. Appl. No. 14/281,803 Office Action dated Jun. 30, 2016.
U.S. Appl. No. 14/594,047 Final Office Action dated Jun. 2, 2016.
U.S. Appl. No. 14/606,239 Office Action dated Jun. 10, 2016.
U.S. Appl. No. 13/141,682 Notice of Allowance dated Aug. 22, 2016.
U.S. Appl. No. 14/192,792 Office Action dated Aug. 23, 2016.
Walker, F. et al., Specific binding of radioiodinated granulocyte-macrophage colony-stimulating factor to hemopoietic cells. The EMBO Journal 4(4); pp. 933-939 (1985).

* cited by examiner

Figure 5

HIR Ab HC (SEQ ID NO:7)

<u>MDWTWRVFCLLAVAPGAHS</u>QVQLQQSGPELVKPGALVKISCKAS<u>GYTFTNY
DIHWVKQRPGQGLEWIG</u><u>WIYPGDGSTKYNEKFKG</u>KATLTADKSSSTAYMHL
SSLTSEKSAVYFCAR<u>EWAY</u>WGQGTLVTVSAASTKGPSVFPLAPSSKSTSGG
TAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLS
PG

Figure 6

HIR Ab LC (SEQ ID NO:8)

METPAQLLFLLLLWLPDTTGDIQMTQSPSSLSASLGERVSLTCRASQDIGGNLYWLQQGPDGTIK
RLIYATSSLDSGVPKRFSGSRSGSDYSLTISSLESEDFVDYYCLQYSSSPWTFGGGTKLEIKRTV
AAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Figure 7

| HIR Ab HC CDRs | | |
|---|---|---|
| CDR1 | GYTFTNYDIH | SEQ ID NO:1 |
| CDR2 | WIYPGDGSTKYNEKFKG | SEQ ID NO:2 |
| CDR3 | EWAY | SEQ ID NO:3 |
| HIR Ab LC CDRs | | |
| CDR1 | RASQDIGGNLY | SEQ ID NO:4 |
| CDR2 | ATSSLDS | SEQ ID NO:5 |
| CDR3 | LQYSSSPWT | SEQ ID NO:6 |

Figure 8

Amino Acid Sequence of NAGLU (minus signal peptide)
(SEQ ID NO:9)

```
DEAREAAAVRALVARLLGPGPAADFSVSVERALAAKPGLDTYSLGGGGAARVRVRGSTGVAAAAGLHRYL
RDFCGCHVAWSGSQLRLPRPLPAVPGELTEATPNRYRYYQNVCTQSYSFVWWDWARWEREIDWMALNGIN
LALAWSGQEAIWQRVYLALGLTQAEINEFFTGPAFLAWGRMGNLHTWDGPLPPSWHIKQLYLQHRVLDQM
RSFGMTPVLPAFAGHVPEAVTRVFPQVNVTKMGSWGHFNCSYSCSFLLAPEDPIFPIIGSLFLRELIKEF
GTDHIYGADTFNEMQPPSSEPSYLAAATTAVYEAMTAVDTEAVWLLQGWLFQHQPQFWGPAQIRAVLGAV
PRGRLLVLDLFAESQPVYTRTASFQGQPFIWCMLHNFGGNHGLFGALEAVNGGPEAARLFPNSTMVGTGM
APEGISQNEVVYSLMAELGWRKDPVPDLAAWVTSFAARRYGVSHPDAGAAWRLLLRSVYNCSGEACRGHN
RSPLVRRPSLQMNTSIWYNRSDVFEAWRLLLTSAPSLATSPAFRYDLLDLTRQAVQELVSLYYEEARSAY
LSKELASLLRAGGVLAYELLPALDEVLASDSRFLLGSWLEQARAAAVSEAEADFYEQNSRYQLTLWGPEG
NILDYANKQLAGLVANYYTPRWRLFLEALVDSVAQGIPFQQHQFDKNVFQLEQAFVLSKQRYPSQPRGDT
VDLAKKIFLKYYPRWVAGSW
```

Figure 9

Amino Acid Sequence of HIRMAb-HC-NAGLU (SEQ ID NO:10)

MDWTWRVFCLLAVAPGAHSQVQLQQSGPELVKPGALVKISCKASGYTFTNYDIHWVKQRPGQGLE
WIGWIYPGDGSTKYNEKFKGKATLTADKSSSTAYMHLSSLTSEKSAVYFCAREWAYWGQGTLVTV
SAASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGSSSELKTPLGDTTHTSPRSPSSSDEAREAAAVRALVARLLGPGPAADFSVSVERALAAK
PGLDTYSLGGGGAARVRVRGSTGVAAAAGLHRYLRDFCGCHVAWSGSQLRLPRPLPAVPGELTEA
TPNRYRYYQNVCTQSYSFVWWDWARWEREIDWMALNGINLALAWSGQEAIWQRVYLALGLTQAEI
NEFFTGPAFLAWGRMGNLHTWDGPLPPSWHIKQLYLQHRVLDQMRSFGMTPVLPAFAGHVPEAVT
RVFPQVNVTKMGSWGHFNCSYSCSFLLAPEDPIFPIIGSLFLRELIKEFGTDHIYGADTFNEMQP
PSSEPSYLAAATTAVYEAMTAVDTEAVWLLQGWLFQHQPQFWGPAQIRAVLGAVPRGRLLVLDLF
AESQPVYTRTASFQGQPFIWCMLHNFGGNHGLFGALEAVNGGPEAARLFPNSTMVGTGMAPEGIS
QNEVVYSLMAELGWRKDPVPDLAAWVTSFAARRYGVSHPDAGAAWRLLLRSVYNCSGEACRGHNR
SPLVRRPSLQMNTSIWYNRSDVFEAWRLLLTSAPSLATSPAFRYDLLDLTRQAVQELVSLYYEEA
RSAYLSKELASLLRAGGVLAYELLPALDEVLASDSRFLLGSWLEQARAAAVSEAEADFYEQNSRY
QLTLWGPEGNILDYANKQLAGLVANYYTPRWRLFLEALVDSVAQGIPFQQHQFDKNVFQLEQAFV
LSKQRYPSQPRGDTVDLAKKIFLKYYPRWVAGSW

METHODS AND COMPOSITIONS FOR INCREASING N-ACETYLGLUCOSAMINIDASE (NAGLU) ACTIVITY IN THE CNS USING A FUSION ANTIBODY COMPRISING AN ANTI-HUMAN INSULIN RECEPTOR ANTIBODY AND NAGLU

CROSS-REFERENCE TO RELATED APPLICATIONS

This application claims priority to U.S. Provisional Patent Application No. 62/103,506, filed Jan. 14, 2015, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 12, 2017, is named 28570-713_202_SL.txt and is 89,235 bytes in size.

BACKGROUND OF THE INVENTION

Mucopolysaccharidosis (MPS) III, also called MPS-III or Sanfilippo syndrome, is an inherited metabolic disease that mainly affects the central nervous system (CNS). MPS III is caused by defects in enzymes needed to break down long chains of sugar molecules called glycosaminoglycans. There are four main types of MPS-III. Type A (MPS-IIIA) is caused by a defect in the lysosomal enzyme N-sulfoglucosamine sulfohydrolase (SGSH), also called sulfamidase or N-heparan sulfatase, which functions to degrade heparan sulfate glycosaminoglycans (GAGs). SGSH causes the hydrolysis of N-linked sulfate groups from the non-reducing terminal glucosaminide residues of heparan sulfate. Type B (MPS-IIIB) is caused by a defect in alpha-N-acetylglucosaminidase (NAGLU). Type C (MPS-IIIC) is caused by a defect in heparin-alpha-glucosaminide N-acetyltransferase (HGSNAT). Type D (MPS-IIID) is caused by a defect in N-acetylglucosamine-6-sulfatase (GNS). An insufficient level of these enzymes causes a pathological buildup of glycosaminoglycans in, e.g., peripheral tissues, and the CNS. However, the clinical features of MPS-III are almost exclusively neurological. Symptoms begin in early life including behavioral disturbances progressing to dementia and developmental regression, followed by death in the second or third decade. Typically, treatment of a lysosomal storage disorder such as MPS-III would include intravenous enzyme replacement therapy with recombinant enzymes that are deficient. However, systemically administered recombinant enzymes do not cross the blood brain barrier (BBB), and therefore would have little impact on the effects of the disease in the CNS.

SUMMARY OF THE INVENTION

Described herein are methods and compositions for treating a subject suffering from a deficiency of alpha-N-acetylglucosaminidase ("NAGLU"). In certain embodiments, the methods provided herein comprise delivery of NAGLU to the CNS by systemically administering a therapeutically effective amount of a bifunctional fusion antibody or protein. In certain embodiments, the bifunctional fusion antibody comprises the amino acid sequences of an antibody to an endogenous blood brain barrier (BBB) receptor and NAGLU. In some embodiments, the bifunctional fusion antibody is a human insulin antibody (HIR Ab) genetically fused to NAGLU ("HIR Ab-NAGLU fusion antibody"). In certain embodiments, the HIR Ab-NAGLU fusion antibody binds to the extracellular domain of the insulin receptor and is transported across the blood brain barrier ("BBB") into the CNS, while retaining NAGLU enzyme activity. In certain embodiments, the HIR Ab binds to the endogenous insulin receptor on the BBB, and acts as a molecular Trojan horse to ferry the NAGLU into the brain. In certain embodiments, therapeutically effective systemic dose of a HIR Ab-NAGLU fusion antibody for systemic administration is based, in part, on the specific CNS uptake characteristics of the fusion antibody from peripheral blood as described herein.

In one aspect provided herein is a method for treating an NAGLU deficiency in the central nervous system of a subject in need thereof, comprising systemically administering to the subject a therapeutically effective dose of a fusion antibody having NAGLU activity. In some embodiments, the fusion antibody comprises the amino acid sequence of an immunoglobulin heavy chain, the amino acid sequence of an NAGLU, and the amino acid sequence of an immunoglobulin light chain. In some embodiments, the fusion antibody binds to an extracellular domain of an endogenous BBB receptor (e.g., the human insulin receptor) and catalyzes hydrolysis of the N-linked sulfate group from the non-reducing terminal glucosaminide residues of heparan sulfate. In some embodiments, the amino acid sequence of the NAGLU is covalently linked to the carboxy terminus of the amino acid sequence of the immunoglobulin heavy chain. In some embodiments, the NAGLU comprises the amino acid sequence of SEQ ID NO:9.

In some embodiments, the NAGLU retains at least 20% of its activity compared to its activity as a separate entity. In some embodiments, the NAGLU and the immunoglobulin each retains at least 20% of its activity compared to its activity as a separate entity.

In some embodiments, at least about 10 ug of NAGLU enzyme are delivered to the brain. In some embodiments at least about 20 ug of NAGLU enzyme are delivered to the brain. In some embodiments at least about 30 ug of NAGLU enzyme are delivered to the brain. In some embodiments at least about 40 ug of NAGLU enzyme are delivered to the brain. In some embodiments at least about 50 ug of NAGLU enzyme are delivered to the brain. In some embodiments at least about 100 ug of NAGLU enzyme are delivered to the brain. In some embodiments at least about 200 ug of NAGLU enzyme are delivered to the brain. In some embodiments at least about 300 ug of NAGLU enzyme are delivered to the brain. In some embodiments at least about 400 ug of NAGLU enzyme are delivered to the brain. In some embodiments at least about 500 ug of NAGLU enzyme are delivered to the brain. In some embodiments at least about 1000 ug of NAGLU enzyme are delivered to the brain. In some embodiments at least about 5 ug of NAGLU enzyme are delivered to the brain. In some embodiments at least about 1 ug of NAGLU enzyme are delivered to the brain. In some embodiments at least about 0.5 ug of NAGLU enzyme are delivered to the brain. In some embodiments at least about 0.1 ug of NAGLU enzyme are delivered to the brain.

In some embodiments, at least about 200 ug of NAGLU enzyme are delivered to the brain, normalized per 50 kg body weight. In some embodiments, at least about 250 ug of NAGLU enzyme are delivered to the brain, normalized per 50 kg body weight. In some embodiments, at least about 300 ug of NAGLU enzyme are delivered to the brain, normalized per 50 kg body weight. In some embodiments, at least about 400 ug of NAGLU enzyme are delivered to the brain, normalized per 50 kg body weight. In some embodiments, at least about 500 ug of NAGLU enzyme are delivered to the brain, normalized per 50 kg body weight. In some embodiments, at least about 1000 ug of NAGLU enzyme are delivered to the brain, normalized per 50 kg body weight. In some embodiments, at least about 2000 ug of NAGLU enzyme are delivered to the brain, normalized per 50 kg body weight. In some embodiments, at least about 150 ug of NAGLU enzyme are delivered to the brain, normalized per 50 kg body weight. In some embodiments, at least about 100 ug of NAGLU enzyme are delivered to the brain, normalized per 50 kg body weight. In some embodiments, at least about 50 ug of NAGLU enzyme are delivered to the brain, normalized per 50 kg body weight. In some embodiments, at least about 10 ug of NAGLU enzyme are delivered to the brain, normalized per 50 kg body weight.

In some embodiments, the therapeutically effective dose of the fusion antibody comprises at least about 0.5 mg/Kg of body weight. In some embodiments, the therapeutically effective dose of the fusion antibody comprises at least about 0.6 mg/Kg of body weight. In some embodiments, the therapeutically effective dose of the fusion antibody comprises at least about 0.7 mg/Kg of body weight. In some embodiments, the therapeutically effective dose of the fusion antibody comprises at least about 0.8 mg/Kg of body weight. In some embodiments, the therapeutically effective dose of the fusion antibody comprises at least about 0.9 mg/Kg of body weight. In some embodiments, the therapeutically effective dose of the fusion antibody comprises at least about 1 mg/Kg of body weight. In some embodiments, the therapeutically effective dose of the fusion antibody comprises at least about 2 mg/Kg of body weight. In some embodiments, the therapeutically effective dose of the fusion antibody comprises at least about 5 mg/Kg of body weight. In some embodiments, the therapeutically effective dose of the fusion antibody comprises at least about 0.4 mg/Kg of body weight. In some embodiments, the therapeutically effective dose of the fusion antibody comprises at least about 0.3 mg/Kg of body weight. In some embodiments, the therapeutically effective dose of the fusion antibody comprises at least about 0.2 mg/Kg of body weight. In some embodiments, the therapeutically effective dose of the fusion antibody comprises at least about 0.1 mg/Kg of body weight.

In some embodiments, the therapeutically effective dose of the fusion antibody comprises at least about 1000 units/Kg of body weight. In some embodiments, the therapeutically effective dose of the fusion antibody comprises at least about 1500 units/Kg of body weight. In some embodiments, the therapeutically effective dose of the fusion antibody comprises at least about 2000 units/Kg of body weight. In some embodiments, the therapeutically effective dose of the fusion antibody comprises at least about 3000 units/Kg of body weight. In some embodiments, the therapeutically effective dose of the fusion antibody comprises at least about 4000 units/Kg of body weight. In some embodiments, the therapeutically effective dose of the fusion antibody comprises at least about 5000 units/Kg of body weight. In some embodiments, the therapeutically effective dose of the fusion antibody comprises at least about 10,000 units/Kg of body weight. In some embodiments, the therapeutically effective dose of the fusion antibody comprises at least about 15,000 units/Kg of body weight. In some embodiments, the therapeutically effective dose of the fusion antibody comprises at least about 20,000 units/Kg of body weight. In some embodiments, the therapeutically effective dose of the fusion antibody comprises at least about 25,000 units/Kg of body weight. In some embodiments, the therapeutically effective dose of the fusion antibody comprises at least about 900 units/Kg of body weight. In some embodiments, the therapeutically effective dose of the fusion antibody comprises at least about 800 units/Kg of body weight. In some embodiments, the therapeutically effective dose of the fusion antibody comprises at least about 700 units/Kg of body weight. In some embodiments, the therapeutically effective dose of the fusion antibody comprises at least about 600 units/Kg of body weight. In some embodiments, the therapeutically effective dose of the fusion antibody comprises at least about 500 units/Kg of body weight. In some embodiments, the therapeutically effective dose of the fusion antibody comprises at least about 400 units/Kg of body weight. In some embodiments, the therapeutically effective dose of the fusion antibody comprises at least about 300 units/Kg of body weight. In some embodiments, the therapeutically effective dose of the fusion antibody comprises at least about 200 units/Kg of body weight. In some embodiments, the therapeutically effective dose of the fusion antibody comprises at least about 100 units/Kg of body weight.

In some embodiments, the NAGLU specific activity of the fusion antibody is at least 10000 units/mg protein. In some embodiments, the NAGLU specific activity of the fusion antibody is at least 15000 units/mg. In some embodiments, the NAGLU specific activity of the fusion antibody is at least 20000 units/mg. In some embodiments, the NAGLU specific activity of the fusion antibody is at least 30000 units/mg. In some embodiments, the NAGLU specific activity of the fusion antibody is at least 40000 units/mg. In some embodiments, the NAGLU specific activity of the fusion antibody is at least 50000 units/mg. In some embodiments, the NAGLU specific activity of the fusion antibody is at least 100,000 units/mg. In some embodiments, the NAGLU specific activity of the fusion antibody is at least 120,000 units/mg. In some embodiments, the NAGLU specific activity of the fusion antibody is at least 150,000 units/mg.

In some embodiments, systemic administration is parenteral, intravenous, subcutaneous, intramuscular, trans-nasal, intra-arterial, transdermal, or respiratory.

In some embodiments, the fusion antibody is a chimeric antibody. In some embodiments, the fusion antibody is a humanized antibody.

In some embodiments, the immunoglobulin heavy chain is an immunoglobulin heavy chain of IgG. In some embodiments, the immunoglobulin heavy chain is an immunoglobulin heavy chain of IgG1 class.

In some embodiments, the immunoglobulin heavy chain of the fusion antibody comprises a CDR1 corresponding to the amino acid sequence of SEQ ID NO:1 with up to 4 single amino acid mutations, a CDR2 corresponding to the amino acid sequence of SEQ ID NO:2 with up to 6 single amino acid mutations, or a CDR3 corresponding to the amino acid sequence of SEQ ID NO:3 with up to 3 single amino acid mutations, wherein the single amino acid mutations are substitutions, deletions, or insertions.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with up to 3 single amino acid mutations.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with a single amino acid mutation.

In other embodiments, the immunoglobulin heavy chain of the fusion antibody comprises a CDR1 corresponding to the amino acid sequence of SEQ ID NO:1 with a single amino acid mutations, a CDR2 corresponding to the amino acid sequence of SEQ ID NO:2 with a single amino acid mutations, and a CDR3 corresponding to the amino acid sequence of SEQ ID NO:3 with a single amino acid mutation.

In other embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In further embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3.

In some embodiments, the immunoglobulin light chain is an immunoglobulin light chain of kappa or lambda class.

In some embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, or a CDR3 corresponding to the amino acid sequence of SEQ ID NO:6 with up to 5 single amino acid mutations, wherein the single amino acid mutations are substitutions, deletions, or insertions.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, and a CDR3 corresponding to the amino acid sequence of SEQ ID NO:6 with up to 5 single amino acid mutations.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 3 single amino acid mutations, and a CDR3 corresponding to the amino acid sequence of SEQ ID NO:6 with up to 3 single amino acid mutations.

In other embodiments, the immunoglobulin light chain of the fusion antibody comprises a CDR1 corresponding to the amino acid sequence of SEQ ID NO:4 with a single amino acid mutations, a CDR2 corresponding to the amino acid sequence of SEQ ID NO:5 with a single amino acid mutations, and a CDR3 corresponding to the amino acid sequence of SEQ ID NO:6 with a single amino acid mutations.

In other embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In further embodiments, the immunoglobulin light chain of the fusion antibody comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3; and the immunoglobulin light chain comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody is at least 90% identical to SEQ ID NO:7 and the amino acid sequence of the light chain immunoglobulin is at least 90% identical to SEQ ID NO:8.

In some embodiments, the immunoglobulin heavy chain of the fusion antibody is at least 95% identical to SEQ ID NO:7 and the amino acid sequence of the light chain immunoglobulin is at least 95% identical to SEQ ID NO:8.

In some embodiments, the immunoglobulin heavy chain of the fusion antibody comprises SEQ ID NO:7 and the amino acid sequence of the light chain immunoglobulin comprises SEQ ID NO:8.

In some embodiments, the NAGLU comprises an amino acid sequence at least 90% identical to SEQ ID NO:9. In some embodiments, the NAGLU comprises an amino acid sequence at least 95% identical to SEQ ID NO:9. In some embodiments, the NAGLU comprises an amino acid sequence of SEQ ID NO:9.

In other embodiments, the amino acid sequence of the immunoglobulin heavy chain of the fusion antibody at least 90% identical to SEQ ID NO:7; the amino acid sequence of the light chain immunoglobulin is at least 90% identical to SEQ ID NO:8; and the amino acid sequence of the NAGLU is at least 95% identical to SEQ ID NO:9 or comprises SEQ ID NO:9.

In other embodiments, the amino acid sequence of the immunoglobulin heavy chain of the fusion antibody comprises SEQ ID NO:8, the amino acid sequence of the immunoglobulin light chain comprises SEQ ID NO:8, and the amino acid sequence of the NAGLU comprises SEQ ID NO:9

In some embodiments, the fusion antibody provided herein crosses the BBB by binding an endogenous BBB receptor-mediated transport system. In some embodiments, the fusion antibody crosses the BBB via an endogenous BBB receptor selected from the group consisting of the insulin receptor, transferrin receptor, leptin receptor, lipoprotein receptor, and the insulin-like growth factor (IGF) receptor. In some embodiments, the fusion antibody crosses the BBB by binding an insulin receptor.

In some embodiments, the systemic administration is parenteral, intravenous, subcutaneous, intramuscular, transnasal, intra-arterial, transdermal, or respiratory.

In some embodiments, the NAGLU deficiency in the central nervous system is mucopolysaccharidosis Type IIIB (MPS-IIIB) or Sanfilippo syndrome type B.

In some aspects, provided herein is a method for treating an NAGLU deficiency in the central nervous system of a subject in need thereof, comprising systemically administering to the subject a therapeutically effective dose of a fusion antibody having NAGLU activity, wherein the fusion antibody comprises: (a) a fusion protein comprising the amino acid sequences of an immunoglobulin light chain and a NAGLU, and (b) an immunoglobulin heavy chain; wherein the fusion antibody crosses the blood brain barrier (BBB). In some embodiments, the amino acid sequence of the NAGLU is covalently linked to the carboxy terminus of the amino acid sequence of the immunoglobulin light chain.

In some aspects, provided herein is a method for treating an NAGLU deficiency in the central nervous system of a subject in need thereof, comprising systemically administering to the subject a therapeutically effective dose of a fusion antibody having NAGLU activity, wherein the fusion antibody comprises: (a) a fusion protein comprising an amino acid sequence that is at least 90% identical to SEQ ID NO:10, and (b) an immunoglobulin light chain. In some embodiments, the fusion antibody binds to an extracellular domain of an endogenous BBB receptor. In some embodiments, the endogenous BBB receptor is the human insulin receptor. In some embodiments, the fusion antibody catalyzes hydrolysis of N-linked sulfate from heparan sulfate. In some embodiments, the fusion protein comprises an amino acid sequence that is at least 95% identical to SEQ ID NO: 10. In some embodiments, the fusion protein comprises the amino acid sequence of SEQ ID NO: 10.

In some aspects, provided herein is a fusion antibody having NAGLU activity, the fusion antibody comprising (a) a fusion protein comprising an amino acid sequence that is at least 90% identical to SEQ ID NO:10, and (b) an immunoglobulin light chain. In some embodiments, the fusion antibody binds to an extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor receptor. In some embodiments, the fusion antibody catalyzes hydrolysis of N-linked sulfate from heparan sulfate. In some embodiments, the fusion protein comprises an amino acid sequence that is at least 95% identical to SEQ ID NO: 10. In some embodiments, the fusion protein comprises the amino acid sequence of SEQ ID NO: 10.

In some aspects, provided herein is a fusion antibody having NAGLU activity, the fusion antibody comprising (a) a fusion protein comprising the amino acid sequence of an immunoglobulin heavy chain and an NAGLU, and (b) an immunoglobulin light chain. In some embodiments, the amino acid sequence of the NAGLU is covalently linked to the carboxy terminus of the amino acid sequence of the immunoglobulin heavy chain. In some embodiments, provided herein is a fusion antibody having NAGLU activity, the fusion antibody comprising (a) a fusion protein comprising the amino acid sequence of an immunoglobulin light chain and an NAGLU, and (b) an immunoglobulin heavy chain. In some embodiments, the amino acid sequence of the NAGLU is covalently linked to the carboxy terminus of the amino acid sequence of the immunoglobulin light chain. In some embodiments, the fusion antibody binds to the extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor receptor. In some embodiments, the fusion antibody catalyzes hydrolysis of N-linked sulfate from heparan sulfate.

In some embodiments, the fusion protein provided herein further comprises a linker between the amino acid sequence of the NAGLU and the carboxy terminus of the amino acid sequence of the immunoglobulin heavy chain. In some embodiments, the linker is 80%, 85%, 90%, 95%, 96%, 97%, 98%, or 99% identical to amino acids 462-484 of SEQ ID NO:10. In some embodiments, the linker comprises amino acids 462-484 of SEQ ID NO:10.

In some embodiments, provided herein is a pharmaceutical composition comprising a therapeutically effective amount of a fusion antibody described herein and a pharmaceutically acceptable excipient.

In some embodiments, provided herein is an isolated polynucleotide encoding the fusion antibody described herein. In some embodiments, the isolated polynucleotide comprises the nucleic acid sequence of SEQ ID NO:14. In some embodiments, provided herein is a vector comprising an isolated polynucleotide provided herein. In some embodiments, provided herein is a vector comprising the nucleic acid sequence of SEQ ID NO:14. In some embodiments, provided herein is a host cell comprising a vector described herein. In some embodiments, the host cell is a Chinese Hamster Ovary (CHO) cell.

In some aspects, provided herein is a method for treating an NAGLU deficiency in the central nervous system of a subject in need thereof, comprising systemically administering to the subject a therapeutically effective dose of a fusion antibody having NAGLU activity, wherein the fusion antibody comprises (a) a fusion protein comprising the amino acid sequence of an immunoglobulin heavy chain and an NAGLU, and (b) an immunoglobulin light chain. In some embodiments, the amino acid sequence of the NAGLU is covalently linked to the carboxy terminus of the amino acid sequence of the immunoglobulin heavy chain. In some embodiments, provided herein is a method for treating an NAGLU deficiency in the central nervous system of a subject in need thereof, comprising systemically administering to the subject a therapeutically effective dose of a fusion antibody having NAGLU activity, wherein the fusion antibody comprises (a) a fusion protein comprising the amino acid sequence of an immunoglobulin light chain and an NAGLU, and (b) an immunoglobulin heavy chain. In some embodiments, the amino acid sequence NAGLU the NAGLU is covalently linked to the carboxy terminus of the amino acid sequence of the immunoglobulin light chain. In some embodiments, the fusion antibody binds to the extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor. In some embodiments, the fusion antibody catalyzes hydrolysis of N-linked sulfate from heparan sulfate.

In certain embodiments, provided herein are methods and compositions for treating a subject suffering from an enzyme deficiency in the CNS. In certain embodiments, the methods provided herein comprise delivery of an enzyme deficient in mucopolysaccharidosis III (MPS-III) to the CNS by systemically administering a therapeutically effective amount of a bifunctional fusion antibody or protein. In certain embodiments, the bifunctional fusion antibody comprises the amino acid sequences of an antibody to an endogenous blood brain barrier (BBB) receptor and an enzyme deficient in MPS-III. In some embodiments, the bifunctional fusion antibody is a human insulin antibody (HIR Ab) genetically fused to the enzyme. In certain embodiments, the fusion antibody binds to the extracellular domain of the insulin receptor and is transported across the BBB into the CNS, while retaining enzyme activity. In certain embodiments, the fusion antibody binds to the endogenous insulin receptor on the BBB, and acts as a molecular Trojan horse to ferry the enzyme into the brain. In certain embodiments, therapeutically effective systemic dose of a fusion antibody for systemic administration is based, in part, on the specific CNS uptake characteristics of the fusion antibody from peripheral blood as described herein.

In one aspect provided herein is a method for treating an enzyme deficiency in the central nervous system of a subject in need thereof, comprising systemically administering to the subject a therapeutically effective dose of a fusion antibody comprising the amino acid sequence of an immunoglobulin heavy chain, the amino acid sequence of an enzyme deficient in MPS-III, and the amino acid sequence of an immunoglobulin light chain. In some embodiments, the fusion antibody binds to an extracellular domain of an endogenous BBB receptor (e.g., the human insulin receptor). In some embodiments, the amino acid sequence of the enzyme is covalently linked to the carboxy terminus of the amino acid sequence of the immunoglobulin heavy chain.

In certain embodiments, the enzyme deficient in MPS-IIIB is a lysosomal enzyme.

In some embodiments, the enzyme deficient in MPS-IIIB is alpha-N-acetylglucosaminidase (NAGLU).

In some embodiments, the fusion antibody catalyzes hydrolysis of N-linked sulfate from heparan sulfate, catalyzes hydrolysis of N-acetyl-D-glucosamine residues in N-acetyl-alpha-D-glucosaminides, catalyzes acetylation of glucosamine residues of heparan sulphate.

In some embodiments, the enzyme retains at least 20% of its activity compared to its activity as a separate entity. In some embodiments, the enzyme and the immunoglobulin each retains at least 20% of its activity compared to its activity as a separate entity.

In some embodiments, at least about 10 ug of the enzyme are delivered to the brain. In some embodiments at least about 20 ug of the enzyme are delivered to the brain. In some embodiments at least about 30 ug of the enzyme are delivered to the brain. In some embodiments at least about 40 ug of the enzyme are delivered to the brain. In some embodiments at least about 50 ug of the enzyme are delivered to the brain. In some embodiments at least about 100 ug of the enzyme are delivered to the brain. In some embodiments at least about 200 ug of the enzyme are delivered to the brain. In some embodiments at least about 300 ug of the enzyme are delivered to the brain. In some embodiments at least about 400 ug of the enzyme are delivered to the brain. In some embodiments at least about 500 ug of the enzyme are delivered to the brain. In some embodiments at least about 1000 ug of the enzyme are delivered to the brain. In some embodiments at least about 5 ug of the enzyme are delivered to the brain. In some embodiments at least about 1 ug of the enzyme are delivered to the brain. In some embodiments at least about 0.5 ug of the enzyme are delivered to the brain. In some embodiments at least about 0.1 ug of the enzyme are delivered to the brain.

In some embodiments, at least about 200 ug of the enzyme are delivered to the brain, normalized per 50 kg body weight. In some embodiments, at least about 250 ug of the enzyme are delivered to the brain, normalized per 50 kg body weight. In some embodiments, at least about 300 ug of the enzyme are delivered to the brain, normalized per 50 kg body weight. In some embodiments, at least about 400 ug of the enzyme are delivered to the brain, normalized per 50 kg body weight. In some embodiments, at least about 500 ug of the enzyme are delivered to the brain, normalized per 50 kg body weight. In some embodiments, at least about 1000 ug of the enzyme are delivered to the brain, normalized per 50 kg body weight. In some embodiments, at least about 2000 ug of the enzyme are delivered to the brain, normalized per 50 kg body weight. In some embodiments, at least about 150 ug of the enzyme are delivered to the brain, normalized per 50 kg body weight. In some embodiments, at least about 100 ug of the enzyme are delivered to the brain, normalized per 50 kg body weight. In some embodiments, at least about 50 ug of the enzyme are delivered to the brain, normalized per 50 kg body weight. In some embodiments, at least about 10 ug of the enzyme are delivered to the brain, normalized per 50 kg body weight.

In some embodiments, the therapeutically effective dose of the fusion antibody comprises at least about 0.5 mg/Kg of body weight. In some embodiments, the therapeutically effective dose of the fusion antibody comprises at least about 0.6 mg/Kg of body weight. In some embodiments, the therapeutically effective dose of the fusion antibody comprises at least about 0.7 mg/Kg of body weight. In some embodiments, the therapeutically effective dose of the fusion antibody comprises at least about 0.8 mg/Kg of body weight. In some embodiments, the therapeutically effective dose of the fusion antibody comprises at least about 0.9 mg/Kg of body weight. In some embodiments, the therapeutically effective dose of the fusion antibody comprises at least about 1 mg/Kg of body weight. In some embodiments, the therapeutically effective dose of the fusion antibody comprises at least about 2 mg/Kg of body weight. In some embodiments, the therapeutically effective dose of the fusion antibody comprises at least about 5 mg/Kg of body weight. In some embodiments, the therapeutically effective dose of the fusion antibody comprises at least about 0.4 mg/Kg of body weight. In some embodiments, the therapeutically effective dose of the fusion antibody comprises at least about 0.3 mg/Kg of body weight. In some embodiments, the therapeutically effective dose of the fusion antibody comprises at least about 0.2 mg/Kg of body weight. In some embodiments, the therapeutically effective dose of the fusion antibody comprises at least about 0.1 mg/Kg of body weight.

In some embodiments, the therapeutically effective dose of the fusion antibody comprises at least about 1000 units/Kg of body weight. In some embodiments, the therapeutically effective dose of the fusion antibody comprises at least about 1500 units/Kg of body weight. In some embodiments, the therapeutically effective dose of the fusion antibody comprises at least about 2000 units/Kg of body weight. In some embodiments, the therapeutically effective dose of the fusion antibody comprises at least about 3000 units/Kg of body weight. In some embodiments, the therapeutically effective dose of the fusion antibody comprises at least about 4000 units/Kg of body weight. In some embodiments, the therapeutically effective dose of the fusion antibody comprises at least about 5000 units/Kg of body weight. In some embodiments, the therapeutically effective dose of the fusion antibody comprises at least about 10,000 units/Kg of body weight. In some embodiments, the therapeutically effective dose of the fusion antibody comprises at least about 15,000 units/Kg of body weight. In some embodiments, the therapeutically effective dose of the fusion antibody comprises at least about 20,000 units/Kg of body weight. In some embodiments, the therapeutically effective dose of the fusion antibody comprises at least about 25,000 units/Kg of body weight. In some embodiments, the therapeutically effective dose of the fusion antibody comprises at least about 900 units/Kg of body weight. In some embodiments, the therapeutically effective dose of the fusion antibody comprises at least about 800 units/Kg of body weight. In some embodiments, the therapeutically effective dose of the fusion antibody comprises at least about 700 units/Kg of body weight. In some embodiments, the therapeutically effective dose of the fusion antibody comprises at least about 600 units/Kg of body weight. In some embodiments, the therapeutically effective dose of the fusion antibody comprises at least about 500 units/Kg of body weight. In some embodiments, the therapeutically effective dose of the fusion antibody comprises at least about 400 units/Kg of body weight. In some embodiments, the therapeutically effective dose of the fusion antibody comprises at least about 300 units/Kg of body weight. In some embodiments, the therapeutically effective dose of the fusion antibody comprises at least about 200 units/Kg of body weight. In some embodiments, the therapeutically effective dose of the fusion antibody comprises at least about 100 units/Kg of body weight.

In some embodiments, the enzyme specific activity of the fusion antibody is at least 10000 units/mg protein. In some embodiments, the enzyme specific activity of the fusion antibody is at least 15000 units/mg. In some embodiments, the enzyme specific activity of the fusion antibody is at least 20000 units/mg. In some embodiments, the enzyme specific activity of the fusion antibody is at least 30000 units/mg. In some embodiments, the enzyme specific activity of the fusion antibody is at least 40000 units/mg. In some embodiments, the enzyme specific activity of the fusion antibody is at least 50000 units/mg. In some embodiments, the enzyme specific activity of the fusion antibody is at least 100,000 units/mg. In some embodiments, the enzyme specific activity of the fusion antibody is at least 120,000 units/mg. In some embodiments, the enzyme specific activity of the fusion antibody is at least 150,000 units/mg.

In some embodiments, systemic administration is parenteral, intravenous, subcutaneous, intramuscular, trans-nasal, intra-arterial, transdermal, or respiratory.

In some embodiments, the fusion antibody is a chimeric antibody. In some embodiments, the fusion antibody is a humanized antibody.

In some embodiments, the immunoglobulin heavy chain is an immunoglobulin heavy chain of IgG. In some embodiments, the immunoglobulin heavy chain is an immunoglobulin heavy chain of IgG1 class.

In some embodiments, the immunoglobulin heavy chain of the fusion antibody comprises a CDR1 corresponding to the amino acid sequence of SEQ ID NO:1 with up to 4 single amino acid mutations, a CDR2 corresponding to the amino acid sequence of SEQ ID NO:2 with up to 6 single amino acid mutations, or a CDR3 corresponding to the amino acid sequence of SEQ ID NO:3 with up to 3 single amino acid mutations, wherein the single amino acid mutations are substitutions, deletions, or insertions.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with up to 3 single amino acid mutations.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with a single amino acid mutation.

In other embodiments, the immunoglobulin heavy chain of the fusion antibody comprises a CDR1 corresponding to the amino acid sequence of SEQ ID NO:1 with a single amino acid mutations, a CDR2 corresponding to the amino acid sequence of SEQ ID NO:2 with a single amino acid mutations, and a CDR3 corresponding to the amino acid sequence of SEQ ID NO:3 with a single amino acid mutation.

In other embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In further embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3.

In some embodiments, the immunoglobulin light chain is an immunoglobulin light chain of kappa or lambda class.

In some embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, or a CDR3 corresponding to the amino acid sequence of SEQ ID NO:6 with up to 5 single amino acid mutations, wherein the single amino acid mutations are substitutions, deletions, or insertions.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, and a CDR3 corresponding to the amino acid sequence of SEQ ID NO:6 with up to 5 single amino acid mutations.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 3 single amino acid mutations, and a CDR3 corresponding to the amino acid sequence of SEQ ID NO:6 with up to 3 single amino acid mutations.

In other embodiments, the immunoglobulin light chain of the fusion antibody comprises a CDR1 corresponding to the amino acid sequence of SEQ ID NO:4 with a single amino acid mutations, a CDR2 corresponding to the amino acid sequence of SEQ ID NO:5 with a single amino acid mutations, and a CDR3 corresponding to the amino acid sequence of SEQ ID NO:6 with a single amino acid mutations.

In other embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In further embodiments, the immunoglobulin light chain of the fusion antibody comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3; and the immunoglobulin light chain comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody is at least 90% identical to SEQ ID NO:7 and the amino acid sequence of the light chain immunoglobulin is at least 90% identical to SEQ ID NO:8.

In some embodiments, the immunoglobulin heavy chain of the fusion antibody is at least 95% identical to SEQ ID NO:7 and the amino acid sequence of the light chain immunoglobulin is at least 95% identical to SEQ ID NO:8.

In some embodiments, the immunoglobulin heavy chain of the fusion antibody comprises SEQ ID NO:7 and the amino acid sequence of the light chain immunoglobulin comprises SEQ ID NO:8

In some embodiments, the enzyme comprises an amino acid sequence at least 90% identical to SEQ ID NO:9. In some embodiments, the enzyme comprises an amino acid sequence at least 95% identical to SEQ ID NO:9. In some embodiments, the enzyme comprises an amino acid sequence of SEQ ID NO:9.

In some embodiments, the fusion antibody provided herein crosses the BBB by binding an endogenous BBB receptor-mediated transport system. In some embodiments, the fusion antibody crosses the BBB via an endogenous BBB receptor selected from the group consisting of the insulin receptor, transferrin receptor, leptin receptor, lipoprotein receptor, and the insulin-like growth factor (IGF) receptor. In some embodiments, the fusion antibody crosses the BBB by binding an insulin receptor.

In some embodiments, the systemic administration is parenteral, intravenous, subcutaneous, intramuscular, transnasal, intra-arterial, transdermal, or respiratory.

In some embodiments, the enzyme deficiency in the central nervous system is mucopolysaccharidosis IIIB (MPS-IIIB).

In some aspects, provided herein is a method for treating an enzyme deficiency in the central nervous system of a subject in need thereof, comprising systemically administering to the subject a therapeutically effective dose of a fusion antibody comprising (a) a fusion protein comprising the amino acid sequences of an immunoglobulin light chain and an enzyme deficient in mucopolysaccharidosis III (MPS-III), and (b) an immunoglobulin heavy chain; wherein the fusion antibody crosses the blood brain barrier (BBB). In some embodiments, the amino acid sequence of the enzyme is covalently linked to the carboxy terminus of the amino acid sequence of the immunoglobulin light chain.

In some aspects, provided herein is a method for treating an enzyme deficiency in the central nervous system of a subject in need thereof, comprising systemically administering to the subject a therapeutically effective dose of a fusion antibody comprising (a) a fusion protein comprising an amino acid sequence that is at least 90% identical to SEQ ID NO:10; and (b) an immunoglobulin light chain. In some embodiments, the fusion antibody binds to an extracellular domain of an endogenous BBB receptor. In some embodiments, the endogenous BBB receptor is the human insulin receptor. In some embodiments, the fusion antibody catalyzes hydrolysis of N-acetyl-D-glucosamine residues in N-acetyl-alpha-D-glucosaminides. In some embodiments, the fusion protein comprises an amino acid sequence that is at least 95% identical to SEQ ID NO: 10. In some embodiments, the fusion protein comprises the amino acid sequence of SEQ ID NO: 10.

In some aspects, provided herein is a fusion antibody comprising (a) a fusion protein comprising an amino acid sequence that is at least 90% identical to SEQ ID NO: 10, and (b) an immunoglobulin light chain. In some embodiments, the fusion antibody binds to an extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor receptor. In some embodiments, the fusion antibody catalyzes hydrolysis of N-acetyl-D-glucosamine residues in N-acetyl-alpha-D-glucosaminides. In some embodiments, the fusion protein comprises an amino acid sequence that is at least 95% identical to SEQ ID NO: 10. In some embodiments, the fusion protein comprises the amino acid sequence of SEQ ID NO: 10. In some embodiments, described herein are isolated polypeptides comprising an amino acid sequence at least 80%, 85%, 90%, 95%, 96%, 97%, 98%, or 99% identical to SEQ ID NO:10. In some embodiments, described herein are isolated polypeptides comprising SEQ ID NO:10. In some embodiments, described herein are isolated polypeptides comprising amino acids 462-484 of SEQ ID NO:10.

In some aspects, provided herein is a fusion antibody comprising (a) a fusion protein comprising the amino acid sequence of an immunoglobulin heavy chain and an enzyme deficient in mucopolysaccharidosis III (MPS-III), and (b) an immunoglobulin light chain. In some embodiments, the amino acid sequence of the enzyme is covalently linked to the carboxy terminus of the amino acid sequence of the immunoglobulin heavy chain. In some embodiments, provided herein is a fusion antibody comprising (a) a fusion protein comprising the amino acid sequence of an immunoglobulin light chain and an enzyme deficient in mucopolysaccharidosis III (MPS-III), and (b) an immunoglobulin heavy chain. In some embodiments, the amino acid sequence of the enzyme is covalently linked to the carboxy terminus of the amino acid sequence of the immunoglobulin light chain. In some embodiments, the fusion antibody binds to the extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor receptor. In some embodiments, the fusion antibody catalyzes hydrolysis of N-acetyl-D-glucosamine residues in N-acetyl-alpha-D-glucosaminides.

In some embodiments, the fusion protein provided herein further comprises a linker between the amino acid sequence of the enzyme and the carboxy terminus of the amino acid sequence of the immunoglobulin heavy chain.

In some embodiments, provided herein is a pharmaceutical composition comprising a therapeutically effective amount of a fusion antibody described herein and a pharmaceutically acceptable excipient.

In some embodiments, provided herein is an isolated polynucleotide encoding the fusion antibody described herein. In some embodiments, the isolated polynucleotide comprises the nucleic acid sequence of SEQ ID NO:14. In some embodiments, provided herein is a vector comprising an isolated polynucleotide provided herein. In some embodiments, provided herein is a vector comprising the nucleic acid sequence of SEQ ID NO:14. In some embodiments, provided herein is a host cell comprising a vector described herein. In some embodiments, the host cell is a Chinese Hamster Ovary (CHO) cell.

In some aspects, provided herein is a method for treating an enzyme deficiency in the central nervous system of a subject in need thereof, comprising systemically administering to the subject a therapeutically effective dose of a fusion antibody comprising (a) a fusion protein comprising the amino acid sequence of an immunoglobulin heavy chain and an enzyme deficient in mucopolysaccharidosis III (MPS-III), and (b) an immunoglobulin light chain. In some embodiments, the amino acid sequence of the enzyme is covalently linked to the carboxy terminus of the amino acid sequence of the immunoglobulin heavy chain. In some embodiments, provided herein is a method for treating an enzyme deficiency in the central nervous system of a subject in need thereof, comprising systemically administering to the subject a therapeutically effective dose of a fusion antibody comprising (a) a fusion protein comprising the amino acid sequence of an immunoglobulin light chain and an enzyme deficient in mucopolysaccharidosis III (MPS-III), and (b) an immunoglobulin heavy chain. In some embodiments, the amino acid sequence of the enzyme is covalently linked to the carboxy terminus of the amino acid sequence of the immunoglobulin light chain. In some embodiments, the fusion antibody binds to the extracellular domain of an endogenous BBB receptor. In some embodiments, the endogenous BBB receptor is the human insulin receptor. In some embodiments, the fusion antibody is an antibody that binds to the endogenous BBB receptor. In some embodiments, the fusion antibody is an antibody that binds to the human insulin receptor receptor. In some embodiments, the fusion antibody catalyzes hydrolysis of N-acetyl-D-glucosamine residues in N-acetyl-alpha-D-glucosaminides.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present embodiments are set forth with particularity in the appended claims. A better understanding of the features and advantages of the present embodiments will be obtained by reference to the following detailed description that sets forth illustrative embodiments, in which the principles of the present embodiments are utilized, and the accompanying drawings, as follow:

FIG. 5. Amino acid sequence of an immunoglobulin heavy chain variable region from an exemplary human insulin receptor antibody directed against the extracellular domain of the human insulin receptor. The underlined sequences are a signal peptide, CDR1, CDR2, and CDR3, respectively. The heavy chain constant region, derived from human IgG1, is shown in italics.

FIG. 6. Amino acid sequence of an immunoglobulin light chain variable region from an exemplary human insulin receptor antibody directed against the extracellular domain of the human insulin receptor. The underlined sequences are a signal peptide, CDR1, CDR2, and CDR3, respectively. The constant region, derived from human kappa light chain, is shown in italics.

FIG. 7. A table showing the CDR1, CDR2, and CDR3 amino acid sequences from a heavy and light chain of an exemplary human insulin receptor antibody directed against the extracellular domain of the human insulin receptor.

FIG. 8. Amino acid sequence of NAGLU (NP_000254), not including the 23 amino acid enzyme signal peptide (depicted by dashed line) (mature NAGLU).

FIG. 9. Amino acid sequence of a fusion of an exemplary human insulin receptor antibody heavy chain to mature human NAGLU. The underlined sequences are, in order, an IgG signal peptide, CDR1, CDR2, CDR3, and a 23-amino acid sequence linking the carboxy terminus of the heavy chain to the amino terminus of the mature NAGLU. Sequence in italic corresponds to the heavy chain constant region, derived from human IgG1, and minus the carboxy terminal lysine residue. The sequence in bold corresponds to human NAGLU.

DETAILED DESCRIPTION OF THE INVENTION

Figure 1:
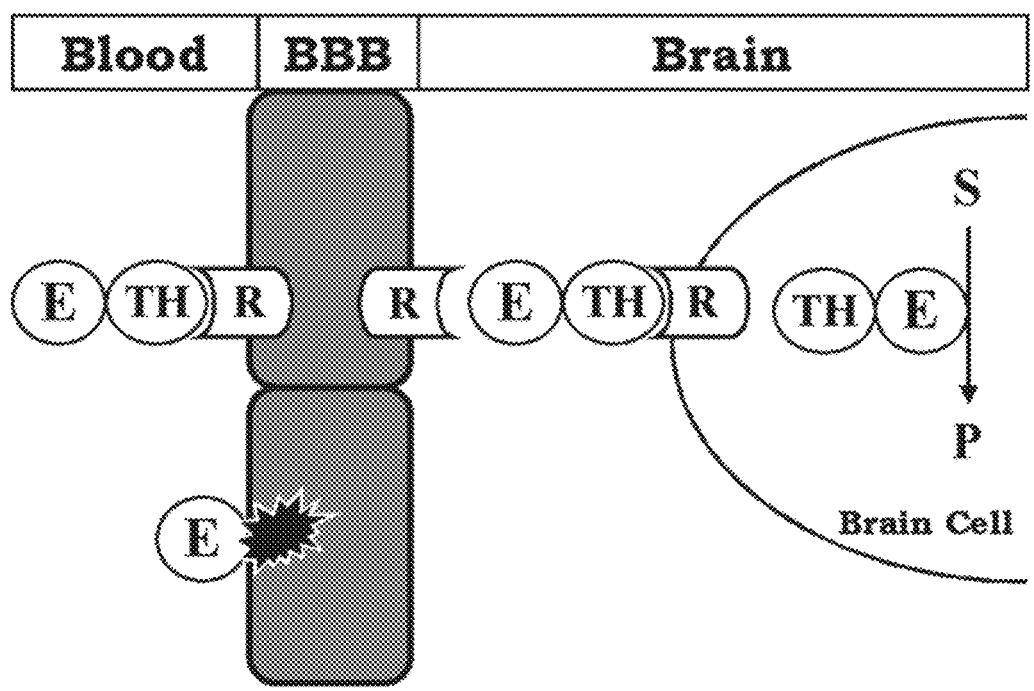
FIG. 1. Schematic depiction of a "molecular trojan horse" strategy in which the fusion antibody comprises an antibody to the extracellular domain of an endogenous BBB receptor (R), which acts as a molecular Trojan horse (TH), and NAGLU, a lysosomal enzyme (E). Once inside brain cells, behind the BBB, the NAGLU part of the fusion antibody then catalyzes hydrolysis of N-acetyl-D-glucosamine residues (S) in N-acetyl-alpha-D-glucosaminides (P).

The blood brain barrier (BBB) is a severe impediment to the delivery of systemically administered lysosomal enzyme (e.g., recombinant NAGLU) to the central nervous system. The methods and compositions described herein address the factors that are important in delivering a therapeutically significant level of an enzyme deficient in mucopolysaccharidosis III (MPS-III), such as SGSH, NAGLU, HGSNAT, GNS, across the BBB to the CNS: 1) Modification of an enzyme deficient in MPS-III to allow it to cross the BBB via transport on an endogenous BBB transporter; 2) the amount and rate of uptake of systemically administered modified enzyme into the CNS, via retention of enzyme activity following the modification required to produce BBB transport. Various aspects of the methods and compositions described herein address these factors, by (1) providing fusion antibodies comprising an enzyme (i.e., a protein having NAGLU activity) fused, with or without intervening sequence, to an immunoglobulin (heavy chain or light chain) directed against the extracellular domain of an endogenous BBB receptor; and (2) establishing therapeutically effective systemic doses of the fusion antibodies based on the uptake in the CNS and the specific activity. In some embodiments, the antibody to the endogenous BBB receptor is an antibody to the human insulin receptor (HIR Ab).

Accordingly, provided herein are compositions and methods for treating an enzyme (e.g., NAGLU) deficiency in the central nervous system by systemically administering to a subject in need thereof a therapeutically effective dose of a bifunctional BBB receptor Ab-enzyme fusion antibody having enzyme activity and selectively binding to the extracellular domain of an endogenous BBB receptor transporter such as the human insulin receptor.

Some Definitions

"Treatment" or "treating" as used herein includes achieving a therapeutic benefit and/or a prophylactic benefit. By therapeutic benefit is meant eradication or amelioration of the underlying disorder or condition being treated. For example, in an individual with MPS-IIIB, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a lysosomal storage disorder), or decreasing the likelihood of occurrence of a condition. As used herein, "treating" or "treatment" includes prophylaxis.

As used herein, the term "effective amount" can be an amount, which when administered systemically, is sufficient to effect beneficial or desired results in the CNS, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions include, but are not limited to, mental retardation, hearing loss, and neurodegeneration. An effective amount can be administered in one or more administrations. In terms of treatment, an "effective amount" of a composition provided herein is an amount that is sufficient to palliate, ameliorate, stabilize, reverse or slow the progression of a disorder, e.g., a neurological disorder. An "effective amount" may be of any of the compositions provided herein used alone or in conjunction with one or more agents used to treat a disease or disorder. An "effective amount" of a therapeutic agent within the meaning of the present embodiments will be determined by a patient's attending physician or veterinarian. Such amounts are readily ascertained by one of ordinary skill in the art and will a therapeutic effect when administered in accordance with the present embodiments. Factors which influence what a therapeutically effective amount will be include, the enzyme specific activity of the fusion antibody administered, its absorption profile (e.g., its rate of uptake into the brain), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from MPS-IIIB.

In some embodiments, a pharmacological composition comprising a fusion antibody is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intraarterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/ excipients can be found in Remington's Pharmaceutical Sciences, Gennaro, A R, ed., 20th edition, 2000: Williams and Wilkins P A, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions described herein may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and proteins are well known in the art.

The Blood Brain Barrier

In one aspect, provided herein are compositions and methods that utilize an enzyme deficient in MPS-IIIB (e.g., NAGLU) fused to an immunoglobulin capable of crossing the blood brain barrier (BBB) via receptor-mediated transport on an endogenous BBB receptor/transporter. An exemplary endogenous transporter for targeting is the insulin receptor on the BBB. The BBB insulin receptor mediates the transport of circulating insulin into the brain, as well as certain peptidomimetic monoclonal antibodies (MAb) such as the HIRMAb. Other endogenous transporters that might be targeted with either an endogenous ligand or a peptidomimetic MAb include the BBB transferrin receptor, the BBB insulin-like growth factor (IGF) receptor, the BBB leptin receptor, or the BBB low density lipoprotein (LDL) receptor. The compositions and methods are useful in transporting NAGLU from the peripheral blood and across the blood brain barrier into the CNS. As used herein, the "blood-brain barrier" refers to the barrier between the peripheral circulation and the brain and spinal cord which is formed by tight junctions within the brain capillary endothelial plasma membranes and creates an extremely tight barrier that restricts the transport of molecules into the brain; the BBB is so tight that it is capable of restricting even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB limits the development of new neurotherapeutics, diagnostics, and research tools for the brain and CNS. Most large molecule therapeutics such as recombinant proteins, antisense drugs, gene medicines, purified antibodies, or RNA interference (RNAi)-based drugs do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route, also called the intra-thecal (IT) route, delivers NAGLU only to the ependymal or meningeal surface of the brain, not into brain parenchyma, which is typical for drugs given by the ICV route. The IC administration of an enzyme such as NAGLU, only provides local delivery, owing to the very low efficiency of protein diffusion within the brain. Similarly, the CED route only provides local delivery in brain near the catheter tip, as drug penetration via diffusion is limited.

The methods described herein offer an alternative to these highly invasive and generally unsatisfactory methods for bypassing the BBB, allowing a functional NAGLU to cross the BBB from the peripheral blood into the CNS following systemic administration of an HIRMAb-NAGLU fusion antibody composition described herein. The methods described herein exploit the expression of insulin receptors (e.g., human insulin receptors) on the BBB to shuttle a desired bifunctional HIRMAb-NAGLU fusion antibody from peripheral blood into the CNS.

Endogenous Receptors

Certain endogenous small molecules in blood, such as glucose or amino acids, are water soluble, yet are able to penetrate the BBB, owing to carrier-mediated transport (CMT) on certain BBB carrier systems. For example, glucose penetrates the BBB via CMT on the GLUT1 glucose transporter. Amino acids, including therapeutic amino acids such as L-DOPA, penetrate the BBB via CMT on the LAT1 large neutral amino acid transporter. Similarly, certain endogenous large molecules in blood, such as insulin, transferrin, insulin-like growth factors, leptin, or low density lipoprotein are able to penetrate the BBB, owing to receptor-mediated transcytosis (RMT) on certain BBB receptor systems. For example, insulin penetrates the BBB via RMT on the insulin receptor. Transferrin penetrates the BBB via RMT on the transferrin receptor. Insulin-like growth factors may penetrate the BBB via RMT on the insulin-like growth factor receptor. Leptin may penetrate the BBB via RMT on the leptin receptor. Low density lipoprotein may penetrate the BBB via transport on the low density lipoprotein receptor.

The BBB has been shown to have specific receptors, including insulin receptors, that allow the transport from the blood to the brain of several macromolecules. In particular, insulin receptors are suitable as transporters for the HIR Ab-NAGLU fusion antibodies described herein. The HIR-NAGLU fusion antibodies described herein bind to the extracellular domain (ECD) of the human insulin receptor.

Insulin receptors and their extracellular, insulin binding domain (ECD) have been extensively characterized in the art both structurally and functionally. See, e.g., Yip et al (2003), *J Biol. Chem*, 278(30):27329-27332; and Whittaker et al. (2005), *J Biol Chem*, 280(22):20932-20936. The amino acid and nucleotide sequences of the human insulin receptor can be found under GenBank accession No. NM_000208.

Antibodies that Bind to an Insulin Receptor-Mediated Transport System

One noninvasive approach for the delivery of an enzyme deficient in MPS-IIIB (e.g., NAGLU) to the CNS is to fuse the NAGLU to an antibody that selectively binds to the ECD of the insulin receptor. Insulin receptors expressed on the BBB can thereby serve as a vector for transport of the NAGLU across the BBB. Certain ECD-specific antibodies may mimic the endogenous ligand and thereby traverse a plasma membrane barrier via transport on the specific receptor system. Such insulin receptor antibodies act as molecular "Trojan horses," or "TH" as depicted schematically in FIG. 1. By itself, NAGLU normally does not cross the blood-brain barrier (BBB). However, following fusion of the NAGLU to the TH, the enzyme is able to cross the BBB, and the brain cell membrane, by trafficking on the endogenous BBB receptor such as the IR, which is expressed at both the BBB and brain cell membranes in the brain (FIG. 1).

Thus, despite the fact that antibodies and other macromolecules are normally excluded from the brain, they can be an effective vehicle for the delivery of molecules into the brain parenchyma if they have specificity for the extracellular domain of a receptor expressed on the BBB, e.g., the insulin receptor. In certain embodiments, an HIR Ab-NAGLU fusion antibody binds an exofacial epitope on the human BBB HIR and this binding enables the fusion antibody to traverse the BBB via a transport reaction that is mediated by the human BBB insulin receptor.

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain Particular amino acid residues are believed to form an interface between the light- and heavy-chain variable domains.

The term "variable domain" refers to protein domains that differ extensively in sequence among family members (i.e., among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR". The variable domains of unmodified heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs", which directly bind, in a complementary manner, to an antigen and are known as CDR1, CDR2, and CDR3 respectively.

In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.* 196:901 917 (1987)).

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR comprises, consist essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. The VFR can form a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("$\kappa$") and lambda or ("$\lambda$"), based on the amino acid sequences of their constant domains.

In referring to an antibody or fusion antibody described herein, the terms "selectively bind," "selectively binding," "specifically binds," or "specifically binding" refer to binding to the antibody or fusion antibody to its target antigen for which the dissociation constant (Kd) is about $10^{-6}$ M or lower, i.e., $10^{-7}$, $10^{-8}$, $10^{-9}$, $10^{-10}$, $10^{-11}$, or $10^{-12}$ M.

The term antibody as used herein will also be understood to mean one or more fragments of an antibody that retain the ability to specifically bind to an antigen, (see generally, Holliger et al., Nature Biotech. 23 (9) 1126-1129 (2005)). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic or natural linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883; and Osbourn et al. (1998) Nat. Biotechnol. 16:778). Such single chain antibodies are also intended to be encompassed within the term antibody. Any VH and VL sequences of specific single chain antibodies can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CH$\gamma$1 ($\gamma$1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in The Pharmacology of Monoclonal Antibodies, Vol. 113, Rosenburg and Moore eds. Springer-Verlag, New York, pp. 269 315 (1994).

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody provided herein is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a HIR Ab is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse, or 100% human. A more highly humanized form of the HIR MAb can also be engineered, and the humanized HIR Ab has activity comparable to the murine HIR Ab and can be used in embodiments provided herein. See, e.g., U.S. Patent Application Publication Nos. 20040101904, filed Nov. 27, 2002 and 20050142141, filed Feb. 17, 2005. Humanized antibodies to the human BBB insulin receptor with sufficient human sequences for use in the present embodiments are described in, e.g., Boado et al. (2007), *Biotechnol Bioeng*, 96(2):381-391.

In exemplary embodiments, the HIR antibodies or fusion antibodies (e.g., HIR-NGLU) derived therefrom contain an immunoglobulin heavy chain comprising CDRs corresponding to the sequence of at least one of the HC CDRs listed in FIG. 7 (SEQ ID NOs 1-3) or a variant thereof. For example, a HC CDR1 corresponding to the amino acid sequence of SEQ ID NO:1 with up to 1, 2, 3, 4, 5, or 6 single amino acid mutations, a HC CDR2 corresponding to the amino acid sequence of SEQ ID NO:2 with up to 1, 2, 3, 4, 5, 6, 7, 8, 9, or 10 single amino acid mutations, or a HC CDR3 corresponding to the amino acid sequence of SEQ ID NO:3 with up to 1, or 2 single amino acid mutations, where the single amino acid mutations are substitutions, deletions, or insertions.

In other embodiments, the HIR Abs or fusion Abs (e.g., HIR Ab-NGLU) contain an immunoglobulin HC the amino acid sequence of which is at least 50% identical (i.e., at least, 55, 60, 65, 70, 75, 80, 85, 90, 95, or any other percent up to 100% identical) to SEQ ID NO:7 (shown in FIG. 5).

In some embodiments, the HIR Abs or fusion Abs (e.g., HIR Ab-NGLU) include an immunoglobulin light chain comprising CDRs corresponding to the sequence of at least one of the LC CDRs listed in FIG. 7 (SEQ ID NOs: 4-6) or a variant thereof. For example, a LC CDR1 corresponding to the amino acid sequence of SEQ ID NO:4 with up to 1, 2, 3, 4, or 5 single amino acid mutations, a LC CDR2 corresponding to the amino acid sequence of SEQ ID NO:5 with up to 1, 2, 3, or 4 single amino acid mutations, or a LC CDR3 corresponding to the amino acid sequence of SEQ ID NO:6 with up to 1, 2, 3, 4, or 5 single amino acid mutations.

In other embodiments, the HIR Abs or fusion Abs (e.g., HIR Ab-NGLU) contain an immunoglobulin LC the amino acid sequence of which is at least 50% identical (i.e., at least, 55, 60, 65, 70, 75, 80, 85, 90, 95, or any other percent up to 100% identical) to SEQ ID NO:8 (shown in FIG. 6).

In yet other embodiments, the HIR Abs or fusion Abs (e.g., HIR Ab-NGLU) contain both a heavy chain and a light chain corresponding to any of the above-mentioned HIR heavy chains and HIR light chains.

HIR antibodies provided herein may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

One of ordinary skill in the art will appreciate that current technologies permit a vast number of sequence variants of candidate HIR Abs or known HIR Abs to be readily generated be (e.g., in vitro) and screened for binding to a target antigen such as the ECD of the human insulin receptor or an isolated epitope thereof. See, e.g., Fukuda et al. (2006) "In vitro evolution of single-chain antibodies using mRNA display," *Nuc. Acid Res.*, 34(19) (published online) for an example of ultra high throughput screening of antibody sequence variants. See also, Chen et al. (1999), "In vitro scanning saturation mutagenesis of all the specificity determining residues in an antibody binding site," *Prot Eng*, 12(4): 349-356. An insulin receptor ECD can be purified as described in, e.g., Coloma et al. (2000) *Pharm Res*, 17:266-274, and used to screen for HIR Abs and HIR Ab sequence variants of known HIR Abs.

Accordingly, in some embodiments, a genetically engineered HIR Ab, with the desired level of human sequences, is fused to an enzyme deficient in MPS-III (e.g., NAGLU), to produce a recombinant fusion antibody that is a bi-functional molecule. For example, the HIR Ab-NAGLU fusion antibody: (i) binds to an extracellular domain of the human insulin receptor; (ii) degrades heparan sulfate by hydrolysis of terminal N-acetyl-D-glucosamine residues in N-acetyl-alpha-D-glucosaminides; and (iii) is able to cross the BBB, via transport on the BBB HIR, and retain NAGLU activity once inside the brain, following peripheral administration.

N-Acetylglucosaminidase, Alpha (NAGLU)

Systemic administration (e.g., by intravenous injection) of recombinant NAGLU is not expected to rescue a deficiency of NAGLU in the CNS of patients suffering from MPS-IIIB. NAGLU does not cross the BBB, and the lack of transport of the enzyme across the BBB prevents it from having a significant therapeutic effect in the CNS following peripheral administration. However, present inventors have discovered that when the NAGLU is fused to an antibody that crosses the BBB such as HIR Ab (e.g., by a covalent linker), this enzyme is now able to enter the CNS from blood following a non-invasive peripheral route of administration such as intravenous, intra-arterial, intramuscular, subcutaneous, intraperitoneal, or even oral administration. Administration of a HIR Ab-NAGLU fusion antibody enables delivery of NAGLU activity into the brain from peripheral blood. Described herein is the determination of a systemic dose of the HIR Ab-NAGLU fusion antibody that is therapeutically effective for treating a NAGLU deficiency in the CNS. As described herein, appropriate systemic doses of an HIR Ab-NAGLU fusion antibody are established based on a quantitative determination of CNS uptake characteristics and enzymatic activity of an HIR Ab-enzyme fusion antibody.

Heparan sulfate is a sulfated glycosoaminoglycan synthesized in the oligodendrocytes in the central nervous system. As used herein, NAGLU (e.g., the human NAGLU sequence listed under GenBank Accession No. NP_000254) refers to any naturally occurring or artificial enzyme that can catalyze the hydrolysis of terminal N-acetyl-D-glucosamine residues in N-acetyl-alpha-D-glucosaminides.

In some embodiments, NAGLU has an amino acid sequence that is at least 50% identical (i.e., at least, 55, 60, 65, 70, 75, 80, 85, 90, 95, or any other percent up to 100% identical) to the amino acid sequence of human NAGLU, a 743 amino acid protein listed under Genbank NP_000254, or a 720 amino acid subsequence thereof, which lacks a 23 amino acid signal peptide, and corresponds to SEQ ID NO:9 (FIG. 8). The cloning and expression of human NAGLU has been described both by Zhao et al (1996), "The molecular basis of Sanfilippo syndrome type B," *Proc. Natl. Acad. Sci., USA.,* 93: 6101-6105, and Weber et al (1996), "Cloning and expression of the gene involved in Sanfilippo B syndrome (mucopolysaccharidosis IIIB), *Human Molecular Genetics,* 5: 771-777.

In some embodiments, NAGLU has an amino acid sequence at least 50% identical (i.e., at least, 55, 60, 65, 70, 75, 80, 85, 90, 95, or any other percent up to 100% identical) to SEQ ID NO:9 (shown in FIG. 8). Sequence variants of a canonical NAGLU sequence such as SEQ ID NO:9 can be generated, e.g., by random mutagenesis of the entire sequence or specific subsequences corresponding to particular domains. Alternatively, site directed mutagenesis can be performed reiteratively while avoiding mutations to residues known to be critical to NAGLU function such as those given above. Further, in generating multiple variants of an NAGLU sequence, mutation tolerance prediction programs can be used to greatly reduce the number of non-functional sequence variants that would be generated by strictly random mutagenesis. Various programs) for predicting the effects of amino acid substitutions in a protein sequence on protein function (e.g., SIFT, PolyPhen, PANTHER PSEC, PMUT, and TopoSNP) are described in, e.g., Henikoff et al. (2006), "Predicting the Effects of Amino Acid Substitutions on Protein Function," *Annu. Rev. Genomics Hum. Genet.,* 7:61-80. NAGLU sequence variants can be screened for of NAGLU activity/retention of NAGLU activity by a fluorometric enzymatic assay known in the art, Marsh and Fensom (1985): 4-Methylumbelliferyl a-N-acetylglucosaminidase activity for diagnosis of Sanfilippo B disease, *Clinical Genetics,* 27: 258-262. Accordingly, one of ordinary skill in the art will appreciate that a very large number of operable NAGLU sequence variants can be obtained by generating and screening extremely diverse "libraries" of NAGLU sequence variants by methods that are routine in the art, as described above.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:9) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM *J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present embodiments also include proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present embodiments. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the present embodiments.

Compositions

It has been found that the bifunctional fusion antibodies described herein, retain a high proportion of the activity of their separate constituent proteins, e.g., binding of the antibody capable of crossing the BBB (e.g., HIR Ab) to the extracellular domain of an endogenous receptor on the BBB (e.g., IR ECD), and the enzymatic activity of an enzyme deficient in MPS-III (e.g., NAGLU). Construction of cDNAs and expression vectors encoding any of the proteins described herein, as well as their expression and purification are well within those of ordinary skill in the art, and are described in detail herein in, e.g., Examples 1-3, and, in Boado et al (2007), *Biotechnol Bioeng* 96:381-391, U.S. patent application Ser. No. 11/061,956, and U.S. patent application Ser. No. 11/245,710.

Described herein are bifunctional fusion antibodies containing an antibody to an endogenous BBB receptor (e.g., HIR Ab), as described herein, capable of crossing the BBB fused to NAGLU, where the antibody to the endogenous BBB receptor is capable of crossing the blood brain barrier and the NAGLU each retain an average of at least about 10, 20, 30, 40, 50, 60, 70, 80, 90, 95, 99, or 100% of their activities, compared to their activities as separate entities. In some embodiments, provided herein is a HIR Ab-NAGLU fusion antibody where the HIR Ab and NAGLU each retain an average of at least about 50% of their activities, compared to their activities as separate entities. In some embodiments, provided herein is a HIR Ab-NAGLU fusion antibody where the HIR Ab and NAGLU each retain an average of at least about 60% of their activities, compared to their activities as separate entities. In some embodiments, provided herein is a HIR Ab-NAGLU fusion antibody where the HIR Ab and NAGLU each retain an average of at least about 70% of their activities, compared to their activities as separate entities. In some embodiments, provided herein is a HIR Ab-NAGLU fusion antibody where the HIR Ab and NAGLU each retain an average of at least about 80% of their activities, compared to their activities as separate entities. In some embodiments, provided herein is a fusion HIR Ab-NAGLU fusion antibody where the HIR Ab and NAGLU each retain an average of at least about 90% of their activities, compared to their activities as separate entities. In some embodiments, the HIR Ab retains at least about 10, 20, 30, 40, 50, 60, 70, 80, 90, 95, 99, or 100% of its activity, compared to its activity as a separate entity, and the NAGLU retains at least about 10, 20, 30, 40, 50, 60, 70, 80, 90, 95, 99, or 100% of its activity, compared to its activity as a separate entity. Accordingly, described herein are compositions containing a bifunctional HIR Ab-NAGLU fusion antibody capable of crossing the BBB, where the constituent HIR Ab and NAGLU each retain, as part of the fusion antibody, an average of at least about 10, 20, 30, 40, 50, 60, 70, 80, 90, 95, 99, or 100% of their activities, i.e., HIR binding and NAGLU activity, respectively, compared to their activities as separate proteins. An HIR Ab NAGLU fusion antibody refers to a fusion protein comprising any of the HIR antibodies and NAGLU described herein.

In any of the embodiments provided herein, HIR Ab may be replaced by an antibody to an endogenous BBB receptor described herein, such as an antibody to transferrin receptor, leptin receptor, lipoprotein receptor, or the insulin-like growth factor (IGF) receptor, or other similar endogenous BBB receptor-mediated transport system.

In the fusion antibodies described herein, the covalent linkage between the antibody and the NAGLU may be to the carboxy or amino terminal of the antibody heavy or light chain and the amino or carboxy terminal of the NAGLU as long as the linkage allows the fusion antibody to bind to the ECD of the IR and cross the blood brain barrier, and allows the NAGLU to retain a therapeutically useful portion of its activity. In certain embodiments, the covalent link is between an HC of the antibody and the NAGLU or a LC of the antibody and the NAGLU. Any suitable linkage may be used, e.g., carboxy terminus of light chain to amino terminus of NAGLU, carboxy terminus of heavy chain to amino terminus of NAGLU, amino terminus of light chain to amino terminus of NAGLU, amino terminus of heavy chain to amino terminus of NAGLU, carboxy terminus of light chain to carboxy terminus of NAGLU, carboxy terminus of heavy chain to carboxy terminus of NAGLU, amino terminus of light chain to carboxy terminus of NAGLU, or amino terminus of heavy chain to carboxy terminus of NAGLU. In some embodiments, the linkage is from the carboxy terminus of the HC to the amino terminus of the NAGLU.

The NAGLU may be fused, or covalently linked, to the targeting antibody (e.g., MAb, HIR-MAb) through a linker. A linkage between terminal amino acids can be accomplished by an intervening peptide linker sequence that forms part of the fused amino acid sequence. The peptide sequence linker may be 0, 1, 2, 3, 4, 5, 6, 7, 8, 9, 10, 15, 20, 25, 26, 27, 28, 29, 30, 31, 32, 33, 34, 35, 36, 37, 38, 39, 40 or more than 40 amino acids in length. In some embodiments, including some preferred embodiments, the peptide linker is less than 50, 45, 40, 35, 34, 33, 32, 31, 30, 20, 15, 14, 13, 12, 11, 10, 9, 8, 7, 6, 5, 4, 3, 2, or 1 amino acids in length. In some embodiments, including some preferred embodiments, the peptide linker is at least 20 to 35 amino acids in length. In some embodiments, the peptide linker is 23 amino acids in length. In some embodiments, the peptide linker is 31 amino acids in length. In some embodiments, the linker comprises amino acids 462-484 of SEQ ID NO:10. In some embodiments, the NAGLU is directly linked to the targeting antibody, and is therefore 0 amino acids in length, as is represented in SEQ ID NO:21.

In some embodiments, the linker comprises glycine, serine, and/or alanine residues in any combination or order. In some cases, the combined percentage of glycine, serine, and alanine residues in the linker is at least 5%, 10%, 15%, 20%, 25%, 30%, 40%, 50%, 60%, 70%, 75%, 80%, 90%, or 95% of the total number of residues in the linker. In some preferred embodiments, the combined percentage of glycine, serine, and alanine residues in the linker is at least 50%, 60%, 70%, 75%, 80%, 90%, or 95% of the total number of residues in the linker. In some embodiments, any number of combinations of amino acids (including natural or synthetic amino acids) can be used for the linker. In some embodiments, a three amino acid linker is used. In some embodiments, the linker has the sequence Ser-Ser-Ser. In some embodiments, a two amino acid linker comprises glycine, serine, and/or alanine residues in any combination or order (e.g., Gly-Gly, Ser-Gly, Gly-Ser, Ser-Ser, Ala-Ala, Ser-Ala, or Ala-Ser linker). In some embodiments, a two amino acid linker consists of one glycine, serine, and/or alanine residue along with another amino acid (e.g., Ser-X, where X is any known amino acid). In still other embodiments, the two-amino acid linker consists of any two amino acids (e.g., X-X), except gly, ser, or ala.

In some embodiments, the linker is derived from the sequence of an endogenous human protein, such as the hinge region from human IgG3, which is comprised of 62 amino acids. In some embodiments, the linker is derived from a truncated version of the human IgG3 hinge region, such as the first 17 amino acids. In some embodiments, the linker is derived from the upper and core hinge regions of human IgG3. In some embodiments, the linker is derived from the upper, core, and lower hinge region of human IgG3. In some embodiments, the cysteine residues of the human IgG3 hinge region are mutated to serine residues, so as to eliminate disulfide bonding between chains. In some embodiments, a serine-serine-serine spacer is placed on both the amino terminal and carboxyl terminal sides of the hinge sequence. These embodiments comprise the linker shown in FIG. 9 (underlined), which corresponds to amino acids 462-484 of SEQ ID NO:10 (FIG. 9). In some embodiments, the linker is derived from the upper and core hinge regions of human IgG3 and the cysteine residues are mutated to serine residues, but the linker comprises 1, 2, 3, 4, 5, 6, 7, 8, 9, 10, or more than 10 amino acid substitutions. In some embodiments, the linker is derived from the upper, core, and lower hinge regions of human IgG3 and the cysteine residues are mutated to serine residues, but the linker comprises 1, 2, 3, 4, 5, 6, 7, 8, 9, 10, or more than 10 amino acid substitutions.

As described herein, in some embodiments a linker that is greater than two amino acids in length. Such linker may also comprise glycine, serine, and/or alanine residues in any combination or order, as described further herein. In some embodiments, the linker consists of one glycine, serine, and/or alanine residue along with other amino acids (e.g., Ser-nX, where X is any known amino acid, and n is the number of amino acids). In still other embodiments, the linker consists of any two amino acids (e.g., X-X). In some embodiments, said any two amino acids are Gly, Ser, or Ala, in any combination or order, and within a variable number of amino acids intervening between them. In an example of an embodiment, the linker consists of at least one Gly. In an example of an embodiment, the linker consists of at least one Ser. In an example of an embodiment, the linker consists of at least one Ala. In some embodiments, the linker consists of at least 1, 2, 3, 4, 5, 6, 7, 8, 9, or 10 Gly, Ser, and/or Ala residues. In preferred embodiments, the linker comprises Gly and Ser in repeating sequences, in any combination or number, such as $(Gly_4Ser)_3$ (SEQ ID NO: 23), or other variations.

A linker for use in the present embodiments may be designed by using any method known in the art. For example, there are multiple publicly-available programs for determining optimal amino acid linkers in the engineering of fusion proteins. Publicly-available computer programs (such as the LINKER program) that automatically generate the amino acid sequence of optimal linkers based on the user's input of the sequence of the protein and the desired length of the linker may be used for the present methods and compositions. Often, such programs may use observed trends of naturally-occurring linkers joining protein subdomains to predict optimal protein linkers for use in protein engineering. In some cases, such programs use other methods of predicting optimal linkers. Examples of some programs suitable for predicting a linker for the present embodiments are described in the art, see, e.g., Xue et al. (2004) Nucleic Acids Res. 32, W562-W565 (Web Server issue providing internet link to LINKER program to assist the design of linker sequences for constructing functional fusion proteins); George and Heringa, (2003), Protein Engineering, 15(11):871-879 (providing an internet link to a linker program and describing the rational design of protein linkers); Argos, (1990), J. Mol. Biol. 211:943-958; Arai et al. (2001) Protein Engineering, 14(8):529-532; Crasto and Feng, (2000) Protein Engineering 13(5):309-312.

The peptide linker sequence may include a protease cleavage site, however this is not a requirement for activity of the NAGLU; indeed, an advantage of these embodiments is that the bifunctional HIR Ab-NAGLU fusion antibody, without cleavage, is partially or fully active both for transport and for activity once across the BBB. FIG. 9 shows an exemplary embodiment of the amino acid sequence of a HIR Ab-NAGLU fusion antibody (SEQ ID NO:10) in which the HC is fused through its carboxy terminus via a 23 amino acid linker to the amino terminus of the NAGLU. In some embodiments, the fused NAGLU sequence is devoid of its 23 amino acid signal peptide, as shown in FIG. 8.

In some embodiments, a HIR Ab-NAGLU fusion antibody provided herein comprises both a HC and a LC. In some embodiments, the HIR Ab-NAGLU fusion antibody is a monovalent antibody. In other embodiments, the HIR Ab-NAGLU fusion antibody is a divalent antibody, as described herein in the Example section.

In some embodiments, the HIR Ab used as part of the HIR Ab-NAGLU fusion antibody can be glycosylated or non-glycosylated; in some embodiments, the antibody is glycosylated, e.g., in a glycosylation pattern produced by its synthesis in a CHO cell.

As used herein, "activity" includes physiological activity (e.g., ability to cross the BBB and/or therapeutic activity), binding affinity of the HIR Ab for the IR ECD, or the enzymatic activity of NAGLU.

Transport of a HIR Ab-NAGLU fusion antibody across the BBB may be compared to transport across the BBB of the HIR Ab alone by standard methods. For example, pharmacokinetics and brain uptake of the HIR Ab-NAGLU fusion antibody by a model animal, e.g., a mammal such as a primate, may be used. Similarly, standard models for determining NAGLU activity may also be used to compare the function of the NAGLU alone and as part of a HIR Ab-NAGLU fusion antibody. See, e.g., Example 4, which demonstrates the enzymatic activity of NAGLU versus HIR Ab-NAGLU fusion antibody. Binding affinity for the IR ECD can be compared for the HIR Ab-NAGLU fusion antibody versus the HIR Ab alone. See, e.g., Example 4 herein.

Also included herein are pharmaceutical compositions that contain one or more HIR Ab-NAGLU fusion antibodies described herein and a pharmaceutically acceptable excipient. A thorough discussion of pharmaceutically acceptable carriers/excipients can be found in Remington's Pharmaceutical Sciences, Gennaro, A R, ed., 20th edition, 2000: Williams and Wilkins P A, USA. Pharmaceutical compositions of the present embodiments include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions provided herein are particular suited for injection, e.g., as a pharmaceutical composition for intravenous, subcutaneous, intramuscular, or intraperitoneal administration. Aqueous compositions provided herein comprise an effective amount of a composition of the present embodiments, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions provided herein may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the CNS uptake characteristics of a HIR Ab-NAGLU fusion antibody as described herein, and according to the subject to be treated, the state of the subject and the effect desired. The person responsible for administration will, in any event, determine the appropriate dose for the individual subject.

In addition to the compounds formulated for parenteral administration, such as intravenous or intramuscular injection, other alternative methods of administration of the present embodiments may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284,262), transdermal administration (See U.S. Pat. Nos. 6,348,210; and 6,322,808) and transmucosal administration (See U.S. Pat. No. 5,656,284). Such methods of administration are well known in the art. One may also use intranasal administration of the present embodiments, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Methods

Described herein are methods for delivering an effective dose of an enzyme deficient in MPS-III (e.g., NAGLU) to the CNS across the BBB by systemically administering a therapeutically effective amount of a fusion antibody, as described herein. In some embodiments, the fusion antibody provided herein is a HIR Ab-NAGLU. Suitable systemic doses for delivery of a HIR Ab-NAGLU fusion antibody is based on its CNS uptake characteristics and NAGLU specific activity as described herein. Systemic administration of a HIR Ab-NAGLU fusion antibody to a subject suffering from an NAGLU deficiency is an effective approach to the non-invasive delivery of NAGLU to the CNS.

The amount of a fusion antibody that is a therapeutically effective systemic dose of a fusion antibody depends, in part, on the CNS uptake characteristics of the fusion antibody to be administered, as described herein, e.g., the percentage of the systemically administered dose to be taken up in the CNS.

In some embodiments, 1% (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered HIR Ab-NAGLU fusion antibody is delivered to the brain as a result of its uptake from peripheral blood across the BBB. In some embodiments, at least 0.5%, (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered dose of the HIR Ab-NAGLU fusion antibody is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

Accordingly, in some embodiments provided herein are methods of administering a therapeutically effective amount of a fusion antibody described herein systemically, to a 5 to 50 kg human, such that the amount of the fusion antibody to cross the BBB provides at least 0.5 ng of NAGLU protein/mg protein in the subject's brain, e.g., 0.5, 1, 3, 10, 30, or 50 or any other value from 0.5 to 50 ng of NAGLU protein/mg protein in the subject's brain.

In some embodiments, the total number of units of enzyme (e.g., NAGLU) activity delivered to a subject's brain is at least, 500 milliunits per gram brain, e.g., at least 1000, 3000, 10000, 30000, 100000, 300000, or 500000 or any other total number of NAGLU units from about 500 to 500,000 milliunits of NAGLU activity delivered per gram brain.

In some embodiments, a therapeutically effective systemic dose comprises at least 50,000, 100,000, 300,000, 1,000,000, 3,000,000, 10,000,000, 50,000,000 or any other systemic dose from about 50,000 to 50,000,000 units of enzyme (e.g., NAGLU) activity.

In other embodiments, a therapeutically effective systemic dose is at least about 10000 units of enzyme (e.g., NAGLU) activity/kg body weight, at least about 10,000, 30,000, 100,000, 300,000, 1,000,000 or any other number of units from about 10,000 to 1,000,000 units of enzyme activity/kg of body weight.

One of ordinary skill in the art will appreciate that the mass amount of a therapeutically effective systemic dose of a fusion antibody provided herein will depend, in part, on its enzyme (e.g., NAGLU) specific activity. In some embodiments, the specific activity of a fusion antibody is at least 10,000 U/mg of protein, at least about 15,000, 25,000, 35,000, 60,000, 75,000, 90,000 or any other specific activity value from about 10,000 units/mg to about 150,000 units/mg.

Thus, with due consideration of the specific activity of a fusion antibody provided herein and the body weight of a subject to be treated, a systemic dose of the fusion antibody can be at least 5 mg, e.g., 5, 10, 15, 20, 25, 30, 35, 40, 45, 50, 55, 60, 65, 70, 75, 100, 300, or any other value from about 5 mg to about 500 mg of fusion antibody (e.g., HIR Ab-NAGLU).

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration. Any suitable fusion antibody, as described herein, may be used.

An NAGLU deficiency as referred to herein includes, one or more conditions known as Sanfilippo syndrome type B, or MPS-IIIB. NAGLU deficiency is characterized by the buildup of heparan sulfate that occurs in the brain and other organs.

The compositions provided herein, e.g., an HIR Ab-NAGLU fusion antibody, may be administered as part of a combination therapy. The combination therapy involves the administration of a composition of the present embodiments in combination with another therapy for treatment or relief of symptoms typically found in a patient suffering from an NAGLU deficiency. If the composition of the present embodiments is used in combination with another CNS disorder method or composition, any combination of the composition of the present embodiments and the additional method or composition may be used. Thus, for example, if use of a composition of the present embodiments is in combination with another CNS disorder treatment agent, the two may be administered simultaneously, consecutively, in overlapping durations, in similar, the same, or different frequencies, etc. In some cases a composition will be used that contains a composition of the present embodiments in combination with one or more other CNS disorder treatment agents.

In some embodiments, the composition, e.g., an HIR Ab-NAGLU fusion antibody is co-administered to the patient with another medication, either within the same formulation or as a separate composition. For example, the fusion antibody provided herein may be formulated with another fusion protein that is also designed to deliver across the human blood-brain barrier a recombinant protein other than NAGLU. Further, the fusion antibody may be formulated in combination with other large or small molecules.

EXAMPLES

The following specific examples are to be construed as merely illustrative, and not limitative of the remainder of the disclosure in any way whatsoever. Without further elaboration, it is believed that one skilled in the art can, based on the description herein, utilize the present embodiments to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Expression and Functional Analysis of HIR Ab-GUSB Fusion Protein

The lysosomal enzyme mutated in MPS-VII, also called Sly syndrome, is β-glucuronidase (GUSB). MPS-VII results in accumulation of glycosoaminoglycans in the brain. Enzyme replacement therapy (ERT) of MPS-VII would not likely be effective for treatment of the brain because the GUSB enzyme does not cross the BBB. In an effort to re-engineer human GUSB to cross the BBB, a HIR Ab-GUSB fusion protein project was initiated.

Human GUSB cDNA corresponding to amino acids $Met_1$-$Thr_{651}$ of the human GUSB protein (NP_000172), including the 22 amino acid signal peptide, and the 18 amino acid carboxyl terminal propeptide, was cloned by reverse transcription (RT) polymerase chain reaction (PCR) and custom oligodexoynucleotides (ODNs). PCR products were resolved in 1% agarose gel electrophoresis, and the expected major single band of ~2.0 kb corresponding to the human GUSB cDNA was isolated. The cloned human GUSB was inserted into a eukaryotic expression plasmid, and this GUSB expression plasmid was designated pCD-GUSB. The entire expression cassette of the plasmid was confirmed by bi-directional DNA sequencing. Transfection of COS cells in a 6-well format with the pCD-GSUB resulted in high GUSB enzyme activity in the conditioned medium at 7 days (Table 1, Experiment A), which validated the successful engineering of a functional human GUSB cDNA. The GUSB enzyme activity was determined with a fluorometric assay using 4-methylumbelliferyl beta-L-glucuronide (MUGlcU), which is commercially available. This substrate is hydolyzed to 4-methylumbelliferone (4-MU) by GUSB, and the 4-MU is detected fluorometrically with a fluorometer using an emission wavelength of 450 nm and an excitation wavelength of 365 nm. A standard curve was constructed with known amounts of 4-MU. The assay was performed at 37 C with 60 min incubations at pH=4.8, and was terminated by the addition of glycine-carbonate buffer (pH=10.5).

A new pCD-HC-GUSB plasmid expression plasmid was engineered, which expresses the fusion protein wherein the carboxyl terminus of the heavy chain (HC) of the HIR Ab is fused to the amino terminus of human GUSB, minus the 22 amino acid GUSB signal peptide, and minus the 18 amino acid carboxyl terminal GUSB propeptide. The GUSB cDNA was cloned by PCR using the pCD-GUSB as template. The forward PCR primer introduces "CA" nucleotides to maintain the open reading frame and to introduce a Ser-Ser linker between the carboxyl terminus of the CH3 region of the HIR Ab HC and the amino terminus of the GUSB minus the 22 amino acid signal peptide of the enzyme. The GUSB reverse PCR primer introduces a stop codon, "TGA," immediately after the terminal Thr of the mature human GUSB protein. DNA sequencing of the expression cassette of the pCD-HC-GUSB encompassed 4,321 nucleotides (nt), including a 714 nt cytomegalovirus (CMV) promoter, a 9 nt Kozak site (GCCGCCACC), a 3,228 nt HC-GUSB fusion protein open reading frame, and a 370 nt bovine growth hormone (BGH) transcription termination sequence. The plasmid encoded for a 1,075 amino acid protein, comprised of a 19 amino acid IgG signal peptide, the 443 amino acid HIRMAb HC, a 2 amino acid linker (Ser-Ser), and the 611 amino acid human GUSB minus the enzyme signal peptide and carboxyl terminal propeptide. The GUSB sequence was 100% identical to $Leu^{23}$-$Thr^{633}$ of human GUSB (NP_000172). The predicted molecular weight of the heavy chain fusion protein, minus glycosylation, is 119,306 Da, with a predicted isoelectric point (pI) of 7.83.

COS cells were plated in 6-well cluster dishes, and were dual transfected with pCD-LC and pCD-HC-GUSB, where pCD-LC is the expression plasmid encoding the light chain (LC) of the chimeric HIR Ab. Transfection was performed using Lipofectamine 2000, with a ratio of 1:2.5, ug DNA:uL Lipofectamine 2000, and conditioned serum free medium was collected at 3 and 7 days. However, there was no specific increase in GUSB enzyme activity following dual transfection of COS cells with the pCD-HC-GUSB and pCD-LC expression plasmids (Table 1, Experiment B). However, the low GUSB activity in the medium could be attributed to the low secretion of the HIRMAb-GUSB fusion protein, as the medium IgG was only 23±2 ng/mL, as determined by a human IgG-specific ELISA. Therefore, COS cell transfection was scaled up to 10×T500 plates, and the HIRMAb-GUSB fusion protein was purified by protein A affinity chromatography. IgG Western blotting demonstrated the expected increase in size of the fusion protein heavy chain. However, the GUSB enzyme activity of the HIRMAb-GUSB fusion protein was low at 6.1±0.1 nmol/hr/ug protein. In contrast, the specific activity of human recombinant GUSB is 2,000 nmol/hr/ug protein [Sands et al (1994) Enzyme replacement therapy for murine mucopolysaccharidosis type VII. *J Clin Invest* 93, 2324-2331]. These results demonstrated the GUSB enzyme activity of the HIR Ab-GUSB fusion protein was >95% lost following fusion of the GUSB to the carboxyl terminus of the HC of the HIR Ab. The affinity of HIR Ab-GUSB fusion protein binding to the extracellular domain (ECD) of the HIR was examined with an ELISA. CHO cells permanently transfected with the HIR ECD were grown in serum free media (SFM), and the HIR ECD was purified with a wheat germ agglutinin affinity column. The HIR ECD was plated on 96-well dishes and the binding of the HIR Ab, and the HIR Ab-GUSB fusion protein to the HIR ECD was detected with a biotinylated goat anti-human IgG (H+L) secondary antibody, followed by avidin and biotinylated peroxidase. The concentration of protein that gave 50% maximal binding, $ED_{50}$, was determined with a non-linear regression analysis. The HIR receptor assay showed there was no decrease in affinity for the HIR following fusion of the 611 amino acid GUSB to the carboxyl terminus of the HIRMAb heavy chain. The ED50 of the HIR Ab binding to the HIR ECD was 0.77±0.10 nM and the ED50 of binding of the HIR Ab-GUSB fusion protein was 0.81±0.04 nM.

In summary, fusion of the GUSB to the carboxyl terminus of the HIR Ab HC resulted in no loss in affinity of binding of the fusion protein to the HIR. However, the GUSB enzyme activity of the fusion protein was decreased by >95%.

In an effort to successfully produce a fusion protein of the HIR Ab and GUSB, a new approach was undertaken, in which the carboxyl terminus of the mature human GUSB, including the GUSB signal peptide, was fused to the amino terminus of the HC of the HIR Ab. This fusion protein was designated GUSB-HIR Ab. The first step was to engineer a new expression plasmid encoding this new fusion protein, and this plasmid was designated pCD-GUSB-HC. The pCD-GUSB-HC plasmid expresses the fusion protein wherein the amino terminus of the heavy chain (HC) of the HIRMAb, minus its 19 amino acid signal peptide, is fused to the carboxyl terminus of human GUSB, including the 22 amino acid GUSB signal peptide, but minus the 18 amino acid carboxyl terminal GUSB propeptide. The pCD-GUSB vector was used as template for PCR amplification of the GUSB cDNA expressing a GUSB protein that contained the 22 amino acid GUSB signal peptide, but lacking the 18 amino acid propeptide at the GUSB carboxyl terminus. The GUSB 18 amino acid carboxyl terminal propeptide in pCD-GUSB was deleted by site-directed mutagenesis (SDM). The latter created an AfeI site on the 3'-flanking region of the Thr$^{633}$ residue of GUSB, and it was designated pCD-GUSB-AfeI. The carboxyl terminal propeptide was then deleted with AfeI and HindIII (located on the 3'-non coding region of GUSB). The HIRMAb HC open reading frame, minus the 19 amino acid IgG signal peptide and including the HIRMAb HC stop codon, was generated by PCR using the HIRMAb HC cDNA as template. The PCR generated HIRMAb HC cDNA was inserted at the AfeI-HindIII sites of pCD-GUSB-AfeI to form the pCD-GUSB-HC. A Ser-Ser linker between the carboxyl terminus of GUSB and amino terminus of the HIRMAb HC was introduced within the AfeI site by the PCR primer used for the cloning of the HIRMAb HC cDNA. DNA sequencing of the pCD-GUSB-HC expression cassette showed the plasmid expressed 1,078 amino acid protein, comprised of a 22 amino acid GUSB signal peptide, the 611 amino acid GUSB, a 2 amino acid linker (Ser-Ser), and the 443 amino acid HIRMAb HC. The GUSB sequence was 100% identical to Met$^1$-Thr$^{633}$ of human GUSB (NP_000172).

Dual transfection of COS cells in a 6-well format with the pCD-LC and pCD-GUSB-HC expression plasmids resulted in higher GUSB enzyme activity in the conditioned medium at 7 days, as compared to dual transfection with the pCD-LC and pCD-HC-GUSB plasmids (Table 1, Experiment C). However, the GUSB-HIRMAb fusion protein was also secreted poorly by the COS cells, as the medium human IgG concentration in the 7 day conditioned medium was only 13±2 ng/mL, as determined by ELISA. COS cell transfection was scaled up to 10×T500 plates, and the GUSB-HIRMAb fusion protein was purified by protein A affinity chromatography. SDS-PAGE demonstrated the expected increase in size of the fusion protein heavy chain. The GUSB enzyme activity of the purified GUSB-HIRMAb fusion protein was high at 226±8 nmol/hr/ug protein, which is 37-fold higher than the specific GUSB enzyme activity of the HIRMAb-GUSB fusion protein. However, the HIR receptor assay showed there was a marked decrease in affinity for the HIR following fusion of the GUSB to the amino terminus of the HIRMAb heavy chain, which resulted in a 95% reduction in receptor binding affinity. The ED50 of the HIR Ab binding to the HIR ECD was 0.25±0.03 nM and the ED50 of binding of the HIR Ab-GUSB fusion protein was 4.8±0.4 nM.

In summary, fusion of the GUSB to the amino terminus of the HIR Ab HC resulted in retention of GUSB enzyme activity of the fusion protein, but caused a 95% reduction in binding of the GUSB-HIR Ab fusion protein to the HIR. In contrast, fusion of the GUSB to the carboxyl terminus of the HIR Ab HC resulted in no loss in affinity of binding of the HIR Ab-GUSB fusion protein to the HIR. However, the GUSB enzyme activity of this fusion protein was decreased by >95%. These findings illustrate the unpredictable nature of the art of fusion of lysosomal enzymes to IgG molecules in such a way that bi-functionality of the IgG-enzyme fusion protein is retained, i.e., high affinity binding of the IgG part to the cognate antigen, as well as high enzyme activity.

TABLE 1

GUSB enzyme activity in COS cells following transfection [Mean ± SE (n = 3 dishes per point)]

| Experiment | Treatment | Medium GUSB activity (nmol/hour/mL) |
|---|---|---|
| A | Lipofectamine 2000 | 65 ± 1 |
|   | pCD-GUSB | 6892 ± 631 |
| B | Lipofectamine 2000 | 76 ± 3 |
|   | pCD-HC-GUSB, | 72 ± 3 |
|   | pCD-LC |  |
| C | Lipofectamine 2000 | 162 ± 7 |
|   | pCD-HC-GUSB, | 155 ± 2 |
|   | pCD-LC |  |
|   | pCD-GUSB-HC, | 1119 ± 54 |
|   | pCD-LC |  |

Example 2

Expression and Functional Analysis of HIR Ab-GCR Fusion Protein

The lysosomal enzyme, mutated in Gaucher's disease (GD) is β-glucocerebrosidase (GCR). Neuronopathic forms of GD affect the CNS, and this results in accumulation of lysosomal inclusion bodies in brain cells, owing to the absence of GCR enzyme activity in the brain. Enzyme replacement therapy (ERT) of GD is not an effective for treatment of the brain because the GCR enzyme does not cross the BBB. In an effort to re-engineer human GCR to cross the BBB, a HIR Ab-GCR fusion protein project was engineered, expressed, and tested for enzyme activity. The human GCR cDNA corresponding to amino acids Ala$_{40}$-Gln$_{536}$ of the human GCR protein (NP_000148), minus the 39 amino acid signal peptide, was custom synthesized by a commercial DNA production company. The GCB cDNA was comprised of 1522 nucleotides (nt), which included the GCB open reading frame, minus the signal peptide through the TGA stop codon. On the 5'-end, a StuI restriction endonuclease (RE) sequence was added, and on the 3'-end, a 14 nt fragment from the 3'-untranslated region of the GCR mRNA was followed by a HindIII RE site. Internal HindIII and StuI sites within the GCR gene were mutated without change of amino acid sequence. The GCR gene was released from the pUC plasmid provided by the vendor with StuI and HindIII, and was inserted at HpaI and HindIII sites of a eukaryotic expression plasmid encoding the HIR Ab heavy chain, and this expression plasmid was designated, pCD-HC-GCR. This expression plasmid expresses the fusion protein wherein the carboxyl terminus of the heavy chain (HC) of the HIR Ab is fused to the amino terminus of human GCR, minus the 39 amino acid GCR signal peptide, with a 3 amino acid linker (Ser-Ser-Ser) between the HIR Ab HC and the GCR. DNA sequencing confirmed the identity of the pCD-HC-GCR expression cassette. The expression cassette was comprised of 5,390 nt, which included a 2134 nt CMV promoter sequence, a 2,889 nt expression cassette, and a 367 BGH polyA sequence. The plasmid encoded for a 963 amino acid protein, which was comprised of a 19 amino acid IgG signal peptide, the 443 amino acid HIRMAb HC, a 3 amino acid linker (Ser-Ser-Ser), and the 497 amino acid human GCR minus the enzyme signal peptide. The GCR sequence was 100% identical to $Als^{40}$-$Gln^{536}$ of human GCR (NP_000148). The predicted molecular weight of the heavy chain fusion protein, minus glycosylation, is 104,440 Da, with a predicted isoelectric point (pI) of 8.42.

The HIR Ab-GCR fusion protein was expressed in transiently transfected COS cells. COS cells were plated in 6-well cluster dishes, and were dual transfected with pCD-LC and pCD-HC-GCR, where pCD-LC is the expression plasmid encoding the light chain (LC) of the chimeric HIR Ab. Transfection was performed using Lipofectamine 2000, with a ratio of 1:2.5, ug DNA:uL Lipofectamine 2000, and conditioned serum free medium was collected at 3 and 7 days. Fusion protein secretion into the serum free medium (SFM) was monitored by human IgG ELISA. The conditioned medium was clarified by depth filtration, and the HIR Ab-GCR fusion protein was purified by protein A affinity chromatography. The purity of the fusion protein was confirmed by reducing SDS-PAGE, and the identity of the fusion protein was confirmed by Western blotting using primary antibodies against either human IgG or human GCR. The IgG and GCR antibodies both reacted with the 130 kDa heavy chain of the HIR Ab-GCR fusion protein.

The GCR enzyme activity of the fusion protein was measured with a fluorometric enzyme assay using 4-methylbumbelliferyl beta-D glucopyranoside (4-MUG) as the enzyme substrate as described previously for enzyme assay of recombinant GCR (J. B. Novo, et al, Generation of a Chinese hamster ovary cell line producing recombinant human glucocerebrosidase, J. Biomed. Biotechnol., Article ID 875383, 1-10, 2012). The GCR enzyme assay was performed with a final concentration of 4-MUG of 5 mM in citrate/phosphate buffer/pH=5.5 with 0.25% Triton X-100, and 0.25% sodium taurocholate, and the incubation was performed at 37 C for 60 minutes. Enzyme activity was stopped by the addition of 0.1 M glycine/0.1 M NaOH. The GCR enzyme converts the 4-MUG substrate to the product, 4-methylumbelliferone (4-MU). An assay standard curve was constructed with 4-MU (0.03 to 3 nmol/tube). Enzyme activity was reported as units/mg protein, where 1 unit=1 umol/min. The enzyme activity of recombinant human GCR is 40 units/mg (Novo et al, 2012). However, the GCR enzyme activity of the HIR Ab-GCR fusion protein was only 0.07 units/mg, which is 99% reduced compared to the specific activity of recombinant GCR.

Examples 1 and 2 illustrate the unpredictability of engineering biologically active IgG-lysosomal enzyme fusion proteins. In both cases, the fusion of either GUSB or GCR to the carboxyl terminus of the heavy chain of the HIR Ab resulted in a >95% loss of enzyme activity. This invention makes the surprising finding that NAGLU enzyme activity is preserved following fusion to the carboxyl terminus of the heavy chain of the HIR Ab, as described in the examples below Example 3

Construction of Human HIR Ab Heavy Chain-NAGLU Fusion Protein Expression Vector

Figure 2:
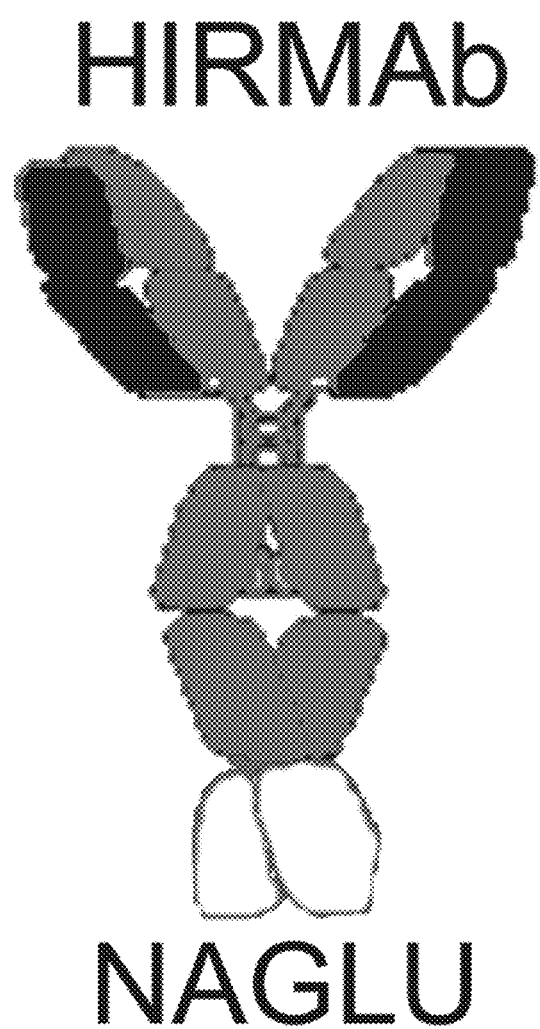
FIG. 2. An exemplary HIR Ab-NAGLU fusion antibody is formed by fusion of the amino terminus of the mature NAGLU to the carboxyl terminus of the CH3 region of the heavy chain of the HIR Ab.

The lysosomal enzyme mutated in MPS-IIIB is NAGLU. MPS-IIIB results in accumulation of heparan sulfate in the brain. Enzyme replacement therapy of MPS-IIIB is not effective for treatment of the brain because the NAGLU enzyme does not cross the BBB, as described by DiNatale et al (2005): Treatment of the mouse model of mucopolysaccharidosis type IIIB with lentiviral-NAGLU vector," *Biochem. J.*, 388: 639-646. NAGLU was fused to the HIR Ab in order to develop a bifunctional molecule capable of both crossing the BBB and exhibiting enzymatic activity. In one embodiment the amino terminus of the mature NAGLU is fused to the carboxyl terminus of each heavy chain of the HIR Ab (FIG. 2).

It was unclear whether the enzymatic activity of the NAGLU would be retained when it was fused to the HIR Ab. The experience with IgG-GUSB and IgG-GCR fusion proteins described in Examples 1 and 2 illustrate the unpredictable nature of the art, and the chance that either the IgG part or the lysosomal enzyme part could lose biological activity following construction of the IgG-enzyme fusion protein. A synthetic gene encoding human NAGLU was obtained from a commercial vendor with the following sequence: (a) nucleotides (nt) 410 through 2572 of Genbank accession number NM_000263, which encoded for the 720 amino acid mature human NAGLU plus the TGA stop codon; (b) a StuI site (AGGCCT) followed by 'CA' was inserted at the 5'-end, to maintain the open reading frame of the NAGLU cDNA with the CH3 region of the HIR Ab heavy chain (HC), and to insert a Ser-Ser-Ser-Ser short linker (SEQ ID NO: 22) between the HIR Ab CH3 region and the NAGLU domain; (c) 20 nt corresponding to the 3'-untranslated region (UTR) of the expression vector (CCGAGCTCGGTACCAAGCTT (SEQ ID NO: 24)), including a HindIII site, was inserted on the 3'end and following the NAGLU TGA stop codon. Additional design features of the synthetic NAGLU gene included: (a) internal restriction endonuclease sites in the NAGLU cDNA to be used in the genetic engineering of the fusion protein expression vectors, e.g. NotI, HindIII and StuI, were mutated, and (b) codon optimization for expression in mammalian cells was performed. The sequence of the 2,191 nt synthetic NAGLU gene is given in SEQ ID NO: 11. The fusion protein comprised of the HIRMAb heavy chain fused to NAGLU via the Ser-Ser-Ser-Ser linker (SEQ ID NO: 22), and the HIRMAb light chain, is alternatively designated the HIRMAb-NAGLU fusion protein or the HIR Ab-NAGLU fusion protein.

Figure 3:
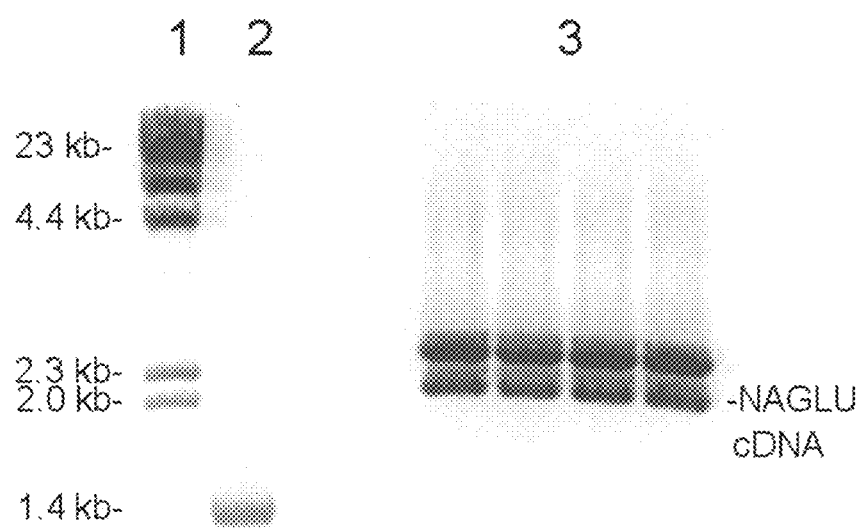
FIG. 3. Agarose gel electrophoresis of pUC57-NAGLU digested with StuI and HindIII is shown in lane 3. The NAGLU synthetic gene (SEQ ID NO: 11) was synthesized by a commercial vendor and provided in the pUC57 cloning vector. The ~2.2 kb NAGLU cDNA was released and separated from the pUC57 plasmid backbone (~3.0 kb) with StuI-HindIII and isolated by agarose gel electrophoresis. Lanes 1 and 2 are DNA size standards.
Figure 4:
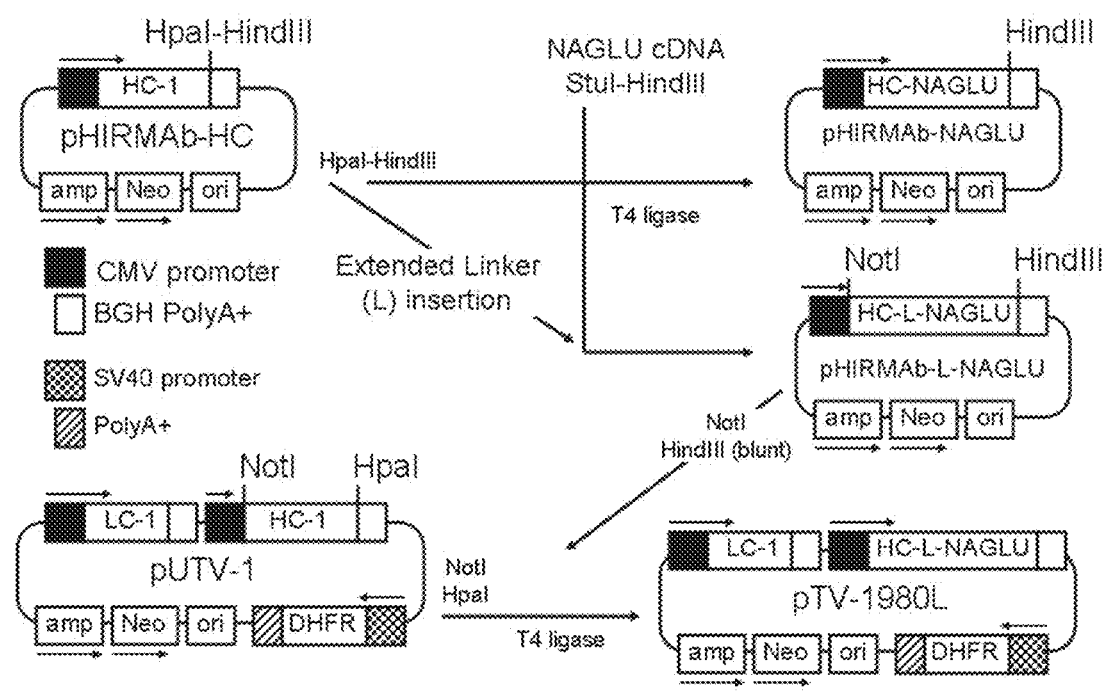
FIG. 4. Genetic engineering of HIRMAb-NAGLU expression vectors is shown. The pHIRMAb-NAGLU heavy chain (HC) fusion protein expression vector was engineered in 2 steps: (a) first, the NAGLU cDNA was released from the pUC57-NAGLU as shown in FIG. 3; and (b) second, the NAGLU cDNA was inserted into the pHIRMAb-HC expression plasmid to produce the pHIRMAb-NAGLU expression plasmid at the HpaI-HindIII restriction endonuclease (RE) sites. The pHIRMAb-NAGLU expresses the heavy chain fusion protein with a short Ser-Ser-Ser-Ser linker (SEQ ID NO: 22) between the CH3 region of HIR Ab heavy chain (HC) and the NAGLU protein domain; the amino sequence of the HIR Ab HC-NAGLU with the short linker is given in SEQ ID NO: 12. The HIR Ab-NAGLU heavy chain fusion protein with the longer 23 amino acid linker is expressed by the plasmid designated pHIRMAb-L-NAGLU, and the amino acid sequence of this fusion protein is given in SEQ ID NO 10 (FIG. 9). This linker corresponds to the 17 amino acids coded by the first part of the IgG3 hinge region flanked by Ser-Ser-Ser on the amino terminus of this linker and a Ser-Ser-Ser on the carboxyl terminus of this linker, and with 2 internal Cys resides mutated to Ser to prevent disulfide bonding. The double stranded cDNA coding for the extended linker and flanked by HpaI and HindIII sites at the 5'- and 3'-end, respectively, was inserted into the pHIRMAb-HC expression vector. Thereafter, the ~2.2 kb NAGLU cDNA digested with StuI-HindIII (FIG. 3) was inserted at the HpaI-HindIII site of the pHIRMAb-HC-extended linker expression vector to form pHIRMAb-L-NAGLU. Clone TV-1890L is a tandem vector (TV) containing genes for i) the HIR Ab LC, ii) the HIR Ab-NAGLU heavy chain fusion protein with the 23 amino acid linker, and iii) the dihydrofolate reductase (DHFR) selection gene. The HIR Ab HC open reading frame (ore is deleted from the universal tandem vector, pUTV-1, with NotI and HpaI. In parallel, the HIRMAb-extended linker-NAGLU HC orf is released from pHIRMAb-L-NAGLU with NotI and HindIII (blunt) and inserted into the NotI-HpaI sites of pUTV-1 to form pTV-1890L.

Initially, the HIR Ab-NAGLU fusion protein was expressed in COS cells following genetic engineering of the pHIRMAb-NAGLU expression plasmid, as outlined in FIG. 4. This plasmid encoded for a heavy chain fusion protein with a short Ser-Ser-Ser-Ser linker (SEQ ID NO: 22), and the amino acid sequence is given in SEQ ID NO:12. The NAGLU gene was synthesized by a commercial vendor, and provided in the pUC57 cloning vector. The 2.2 kb NAGLU engineered cDNA was released from pUC57 plasmid with StuI-HindIII (FIG. 3, lane 3) and purified by agarose gel electrophoresis, followed by insertion into the HpaI-HindIII site of the pHIRMAb-HC expression vector to form the pHIRMAb-NAGLU, as outlined in FIG. 4. The identity of pHIRMAb-NAGLU was confirmed by bidirectional DNA sequencing, and the deduced amino acid sequence is shown in SEQ ID NO:12. The expression of the HIRMAb-NAGLU fusion protein was investigated in COS cells by co-lipofection using both a heavy chain fusion protein expression plasmid, pHIRMAb-NAGLU, and a light chain expression plasmid, pHIRMAb-LC. However, the expression levels of the HIRAb-NAGLU fusion protein were undetectable and no fusion protein could be isolated for biochemical characterization.

In an attempt to increase stability and secretion of the HIR Ab-NAGLU fusion protein, a new fusion protein was engineered with a 23 amino acid linker between the antibody heavy chain C-terminus and the NAGLU N-terminus, and this 23-amino acid linker is designated the 1' linker (L). This fusion protein comprised of the HIRMAb heavy chain fused to NAGLU via the L linker, and the HIRMAb light chain, is alternatively designated the HIRMAb-L-NAGLU fusion protein or the HIR Ab-L-NAGLU fusion protein. This linker corresponds to the 17 amino acids which comprise the sequence of the human IgG3 hinge region, and is derived from the 12 amino acids of the upper hinge region, followed by 5 amino acids of the first part of the core hinge region, and is flanked by a Ser-Ser-Ser sequence on the amino terminus and a Ser-Ser-Ser sequence on the carboxyl terminus. The 2 cysteine residues of the first part of the core hinge region are mutated to serine residues, so as to eliminate disulfide bonding. The sequence of the L linker, SSSELKTPLGDTTHTSPRSPSSS, is underlined in FIG. 9, and corresponds to amino acids 462-484 of SEQ ID NO:10. The expression plasmid DNA encoding the new heavy chain fusion protein is designated pHIRMAb-L-NAGLU in FIG. 4. The double stranded cDNA coding for the L linker was synthesized by a commercial vendor, and contained HpaI and HindIII sites at the 5'- and 3'-ends, respectively, for insertion into the pHIRMAb-HC expression vector (FIG. 4). The ~2.2 kb NAGLU engineered cDNA digested with StuI-HindIII (FIG. 3) was inserted at the HpaI-HindIII site of a HIRMAb-extended linker HC expression vector to form the HIRMAb-extended linker-NAGLU HC expression vector, pHIRMAb-L-NAGLU (FIG. 4). The identity of this plasmid was confirmed by bidirectional DNA sequencing, and the deduced amino acid sequence is shown in SEQ ID NO 10 (FIG. 9). The expression of the new HIRMAb-NAGLU fusion protein was investigated in COS cells by co-lipofection using both the pHIRMAb-L-NAGLU plasmid and the pHIRMAb-LC plasmid. The expression levels in COS cells of the HIRMAb-L-NAGLU fusion protein were low, albeit increased relative to the expression of the HIRMAb-NAGLU fusion protein. The HIRMAb-L-NAGLU fusion protein, with the extended 23 amino acid 1' linker (FIG. 9) was purified by protein A chromatography for biochemical characterization.

Example 4

Stable Transfection of Chinese Hamster Ovary Cells with a Single Tandem Vector Encoding Both Heavy and Light Chains of the HIRMAb-L-NAGLU Fusion Protein For further development of a stably transfected mammalian host cell line, such as a Chinese hamster ovary (CHO) cell line, a tandem vector (TV) containing genes for i) the HIR Ab LC, ii) the HIRMAb-L-NAGLU heavy chain fusion protein, and iii) the DHFR selection gene, is constructed as shown in FIG. 4. This TV encoding for both the fusion heavy chain and the light chain of the HIR Ab-L-NAGLU fusion protein is designated pTV-1890L (FIG. 4). The HIRMAb HC open reading frame (orf) is deleted form the Universal tandem vector, UTV-1, with NotI and HpaI. In parallel, the HIRMAb-L-NAGLU HC orf is released from pHIRMAb-L-NAGLU with NotI and HindIII (blunt) and inserted into the NotI-HpaI sites of pUTV-1 to form pTV-1890L (FIG. 4). The 234 amino acid sequence of the HIR Ab LC is given in SEQ ID NO:8, and the LC is comprised of a 20 amino acid signal peptide followed by a 214 amino acid mature LC. The 714 nucleotide (nt) sequence encoding this LC is given in SEQ ID NO: 13, which is comprised of a 9 nt Kozak sequence (GCCGCCACC), followed by a 702 nt sequence encoding the open reading frame followed by a TAG stop codon. The 1204 amino acid sequence of the HIR Ab HC-L-NAGLU fusion protein is given in SEQ ID NO:10, and the fusion HC is comprised of a 19 amino acid signal peptide followed by a 1185 amino acid mature fusion HC. The 3,624 nt sequence encoding this fusion HC is given in SEQ ID NO: 14, which is comprised of a 9 nt Kozak sequence (GCCGCCACC), followed by a 3,612 nt sequence encoding the open reading frame followed by a TGA stop codon. The 187 amino acid sequence of the DHFR selection protein is given in SEQ ID NO:16. The 573 nt sequence encoding the DHFR is given in SEQ ID NO: 15, which is comprised of a 9 nt Kozak sequence (GCCGCCACC), followed by a 561 nt sequence encoding the open reading frame followed by a TAA stop codon.

Example 5

Figure 10:
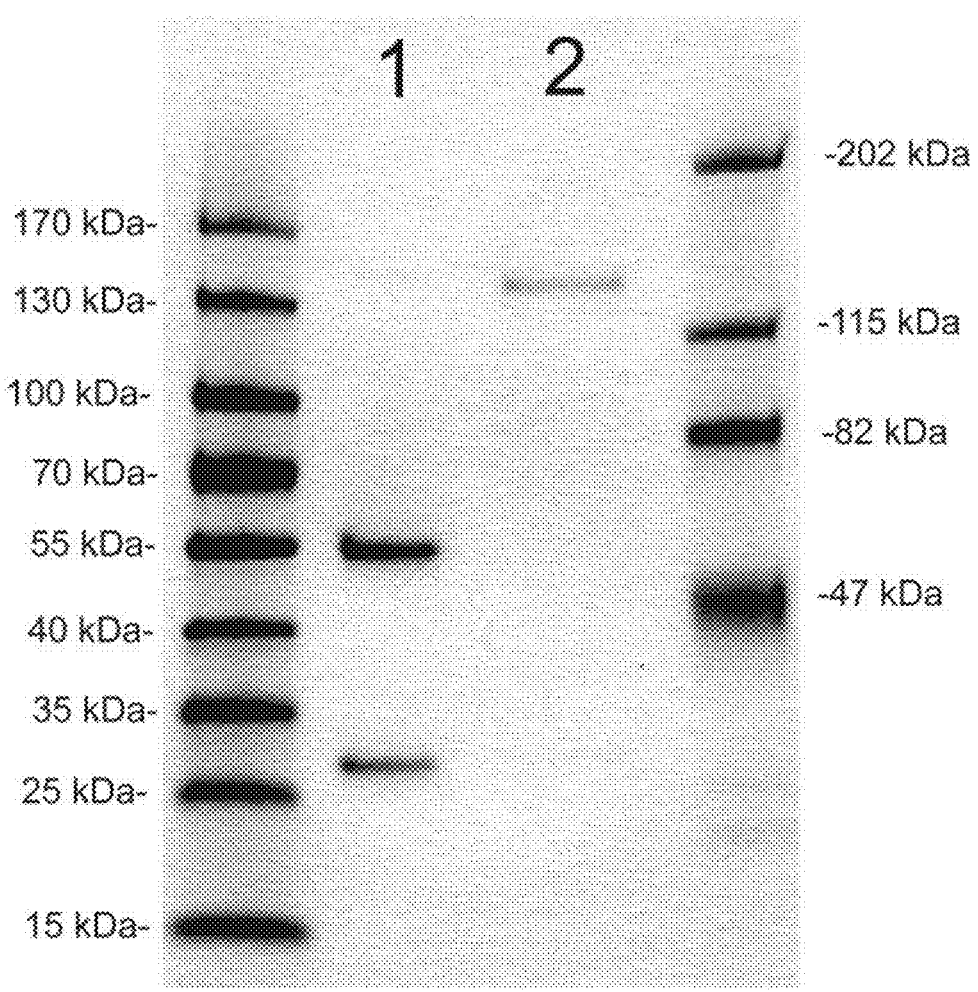
FIG. 10. Reducing SDS-PAGE of molecular weight standards (left and right side lanes), the purified HIRMAb (lane 1), and the purified HIRMAb-L-NAGLU fusion protein (lane 2). The HIRMAb-L-NAGLU fusion protein was produced in COS cells following transient expression.
Figure 11:
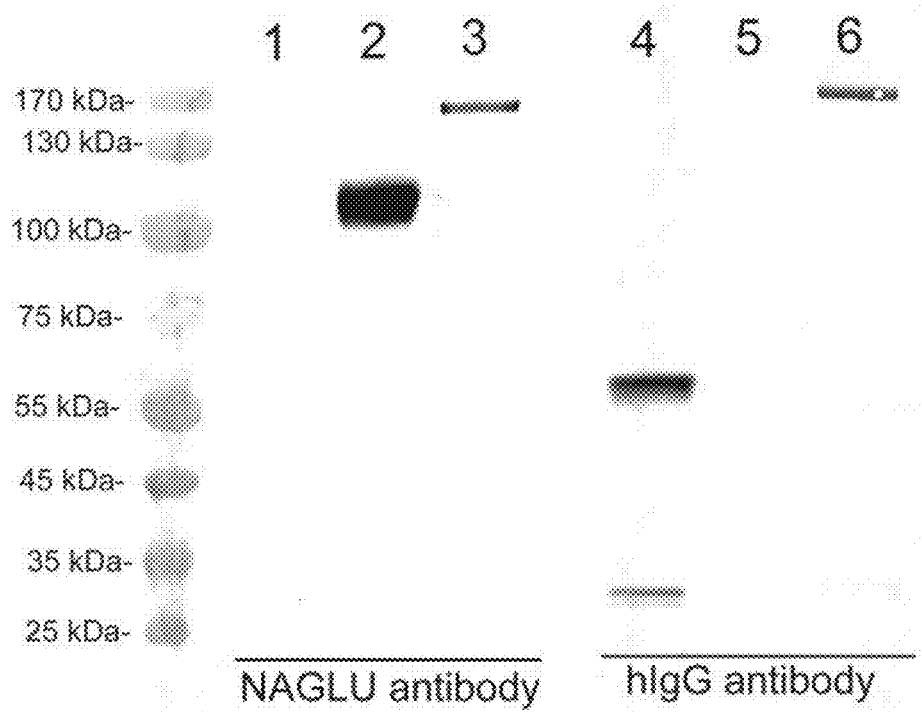
FIG. 11. Western blot with either anti-human (h) IgG primary antibody (right panel) or anti-human NAGLU primary antiserum (left panel). The immunoreactivity of the HIRMAb-L-NAGLU fusion protein (lanes 3 and 6) is compared to the chimeric HIRMAb (lanes 1 and 4) and to recombinant NAGLU (lanes 2 and 5). Both the HIRMAb-L-NAGLU fusion protein and the HIRMAb have identical light chains on the anti-hIgG Western, although the immunoreactive light chain is under-developed on the blot of the fusion protein. The HIRMAb-L-NAGLU fusion heavy chain reacts with both the anti-hIgG and the anti-human NAGLU antibody, whereas the HIRMAb heavy chain only reacts with the anti-hIgG antibody. The recombinant NAGLU reacts only with the anti-human NAGLU antibody. Based on the relative migration of the molecular weight (MW) standards, and the immunoreactive heavy and light chain, the estimated MW of the heavy chain and light chain of the HIRMAb-NAGLU fusion protein is 158 kDa and 30 kDa, respectively, which corresponds to a MW of 375 kDa for the hetero-tetrameric fusion protein shown in FIG. 2. The HIRMAb-L-NAGLU fusion protein was produced in COS cells following transient expression.
Figure 12:
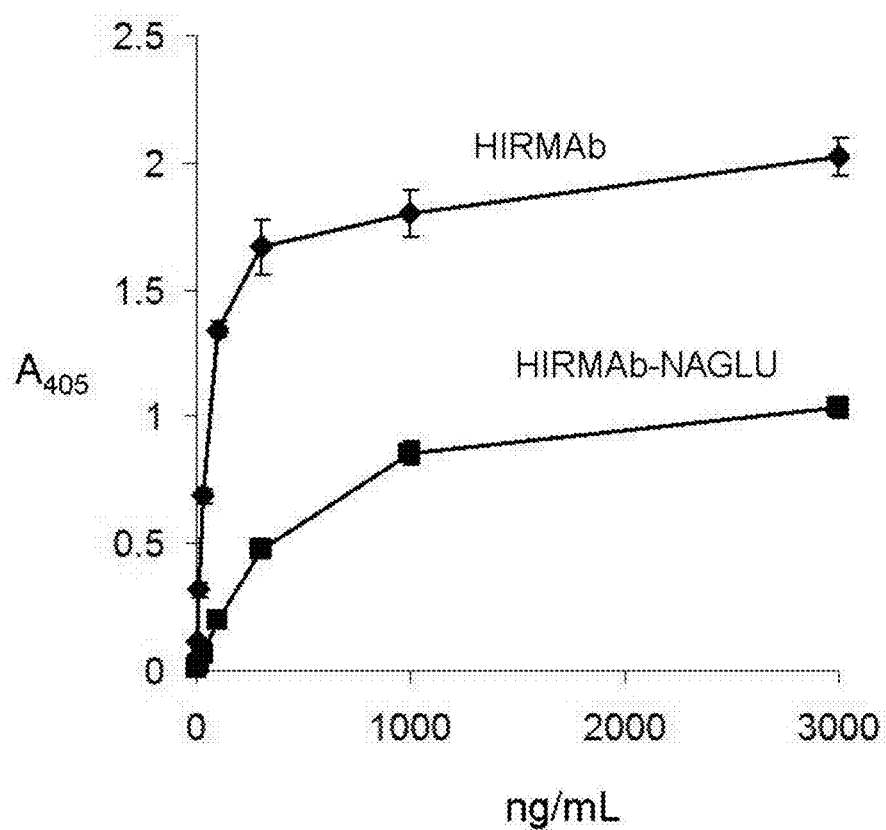
FIG. 12. Binding of either the chimeric HIRMAb or the HIRMAb-L-NAGLU fusion protein to the HIR extracellular domain (ECD) is saturable. The $ED_{50}$ of HIRMAb-L-NAGLU binding to the HIR ECD is about 350 ng/mL, which is 0.93 nM, based on a MW of 375 kDa. This is comparable to the $ED_{50}$ of the binding of the chimeric HIRMAb, about 65 ng/mL, which is 0.43 nM, based on a MW of 150 kDa. The HIRMAb-NAGLU fusion protein was produced in COS cells following transient expression.

Analysis of HIR Binding and NAGLU Activity of the Bi-Functional IgG-L-NAGLU Fusion Protein The COS-derived HIRMAb-L-NAGLU fusion protein was purified by protein A affinity chromatography. The purity of the COS-derived HIRMAb-L-NAGLU fusion protein was verified by reducing SDS-PAGE as shown in FIG. 10. Only the HC and LC proteins are detected for either the HIRMAb alone or the HIRMAb-L-NAGLU fusion protein; the light chain of the fusion protein is present but underdeveloped in the gel. The identity of the COS-derived fusion protein was verified by Western blotting using primary antibodies to either human IgG (FIG. 11, right panel) or human NAGLU (FIG. 11, left panel). The molecular weight (MW) of the HIRMAb-L-NAGLU heavy and light chains, and the MW of the HIRMAb heavy and light chains are estimated by linear regression based on the migration of the MW standards. The size of the HIRMAb-L-NAGLU fusion heavy chain, 158 kDa, is larger than the size of the heavy chain of the HIRMAb, 61 kDa, owing to the fusion of the NAGLU to the HIRMAb heavy chain. The size of the light chain, 30 kDa, is identical for both the HIRMAb-L-NAGLU fusion protein and the HIRMAb antibody, as both proteins use the same light chain. The estimated MW of the heterotetrameric HIRMAb-L-NAGLU fusion protein shown in FIG. 2 is 375 kDa, based on migration in the SDS-PAGE of the Western blot. The affinity of the COS-derived fusion protein for the HIR extracellular domain (ECD) was determined with an ELISA. CHO cells permanently transfected with the HIR ECD were grown in serum free media (SFM), and the HIR ECD was purified with a wheat germ agglutinin affinity column, as previously described in Coloma et al. (2000) *Pharm Res,* 17:266-274. The HIR ECD was plated on Nunc-Maxisorb 96 well dishes and the binding of the HIR Ab, or the HIRMAb-L-NAGLU fusion protein, to the HIR ECD was detected with a biotinylated goat anti-human IgG (H+L) secondary antibody, followed by avidin and biotinylated peroxidase (Vector Labs, Burlingame, Calif.). The concentration of either HIR Ab or HIRMAb-L-NAGLU fusion protein that gave 50% maximal binding, ED50, was determined by inspection. The ED50 of binding to the HIR is 65 ng/mL and the ED50 of binding to the HIR of the HIRMAb-L-NAGLU fusion protein is 350 ng/mL (FIG. 12). The MW of the HIR Ab is 150 kDa, and the MW of the HIRMAb-L-NAGLU fusion protein is 375 kDa. Therefore, after normalization for MW differences, there was comparable binding of either the chimeric HIR Ab or the HIR Ab-NAGLU fusion protein for the HIR ECD with ED50 of 0.43 nM and 0.93 nM, respectively (FIG. 12). These findings show that the affinity of the HIRMAb-L-NAGLU fusion protein binding to the HIR is retained, despite fusion of a NAGLU molecule to the carboxyl termini of both heavy chains of the IgG.

Figure 13:
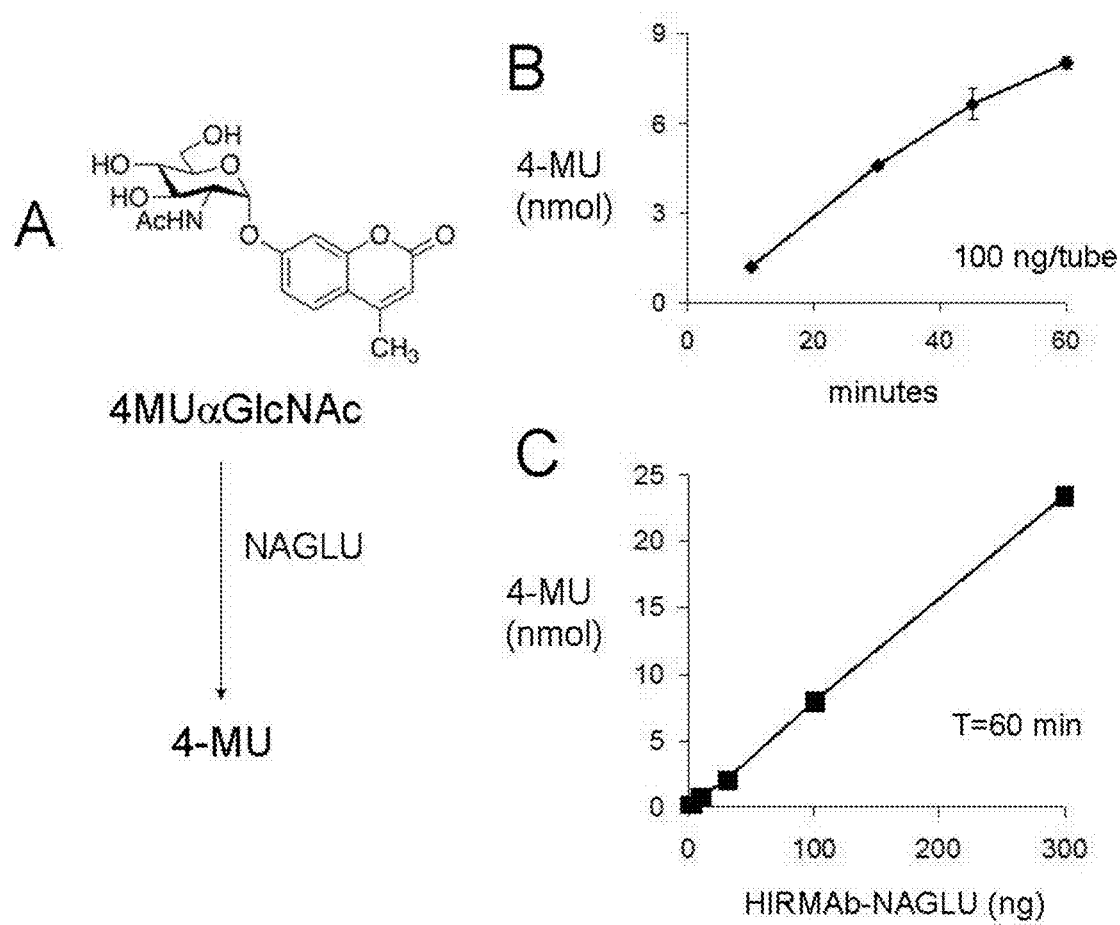
FIG. 13. (A) The structure of the substrate of the NAGLU flurometric enzyme assay, 4-methylumbelliferyl-N-acetyl-α-D-glucosaminide (4MUαGlcNAc), is shown in panel A. Following cleavage of the molecule by NAGLU, the substrate is converted to the fluorescent product, 4-methyl umbelliferone (4-MU). (B) Linear formation of the 4-MU product with respect to incubation time up to 60 minutes, with a fixed amount (100 ng/tube) of the HIRMAb-L-NAGLU fusion protein. (C) Linear formation of the 4-MU product by the addition of the 1 to 300 ng of the HIRMAb-L-NAGLU fusion protein, for a 60 minute incubation. Data are mean±SD of 2 replicates. The HIRMAb-L-NAGLU fusion protein was produced in COS cells following transient expression.

The NAGLU enzyme activity was determined with a fluorometric assay developed by Marsh and Fensom (1985): 4-Methylumbelliferyl α-N-acetylglucosaminidase activity for diagnosis of Sanfilippo B disease, *Clinical Genetics*, 27: 258-262, which uses 4-methylumbelliferyl-N-acetyl-α-D-glucosaminide (4MUαGlcNAc) as the assay substrate. This substrate is commercially available, and the structure of the substrate is outlined in FIG. 13A. This substrate is hydrolyzed by NAGLU to 4-methylumbelliferone (4-MU), as outlined in FIG. 13A. The assay was performed by incubation of the COS-derived HIRMAb-L-NAGLU fusion protein (1 to 300 ng/tube) and the 4MUαGlcNAc substrate in 50 mM sodium acetate buffer/pH=4.3/0.1% bovine serum albumin for 37 C for 10 to 60 minutes. The reaction was stopped by the addition of 0.5 M glycine/NaOH/pH=10.7. Fluorescence was measured with a Farrand fluorometer with a 365 nm excitation filter and a 450 nm emission filter. A standard curve was generated with 0.001 to 1.0 nmol/tube of the 4-MU product, which allowed for conversion of fluorescent units to nmol/tube. The enzyme activity was measured as units/mg protein of the HIRMAb-L-NAGLU fusion protein, where 1 unit=nmol of 4-MU product formed per hour of incubation (Marsh & Fensom, 1985). The assay was linear with respect to incubation time over 1 hours (FIG. 13B), and with respect to mass of fusion protein (FIG. 13C), and the average enzyme activity was 91,300±1,105 units/mg protein. The enzyme specific activity of the recombinant human NAGLU, using the same assay, is 30,000 units/mg protein [Weber et al (1996), "Cloning and expression of the gene involved in Sanfilippo B syndrome (mucopolysaccharidosis IIIB), *Human Molecular Genetics*, 5: 771-777], and 35,000 units/mg protein [Zhao et al (1996), "The molecular basis of Sanfilippo syndrome type B," *Proc. Natl. Acad. Sci., USA.*, 93: 6101-6105]. Following the re-engineering of the NAGLU as a 375 kDa hetero-tetrameric IgG-NAGLU fusion protein (FIG. 2), the effective MW of the NAGLU is 187 kDa, whereas the MW of NAGLU is 80 kDa (Weber et al, 1996). After normalization for MW differences, the effective NAGLU specific activity of the HIRMAb-L-NAGLU protein is comparable to, or greater than, the activity of human NAGLU. Therefore, fusion of the NAGLU to the carboxyl terminus of the HC of the HIR Ab had minimal effect on the enzyme activity of the NAGLU enzyme, in contrast to the result observed with the IgG-GUSB and IgG-GCR fusion proteins (Examples 1 and 2).

Example 6

Amino Acid Linkers Joining the NAGLU and the Targeting Antibody

The mature human NAGLU is fused to the carboxyl terminus of the HC of the HIR Ab with a 23-amino acid 'L' linker (underlined in FIG. 9). Initially, the NAGLU enzyme was fused to the HIR Ab with a Ser-Ser-Ser-Ser 4 amino acid linker (SEQ ID NO: 22), but this fusion protein was not measureably secreted following transient transfection in COS cells (Example 3). In order to increase the flexibility of the junction between the NAGLU and the IgG domains of the fusion protein, the length of the linker was increased to 23 amino acids by combining a (serine)$_3$ sequence, the upper hinge domain, ELKTPLGDTTHT (SEQ ID NO: 25), and the first part of the core hinge domain, CPRCP (SEQ ID NO: 26), of human IgG3, and another (serine)$_3$ sequence. In order to eliminate disulfide bonding, the cysteine (C) residues of the core hinge domain were mutated to serine (S) residues in the final 23-amino acid linker, which is underlined in FIG. 9; this L linker sequence corresponds to amino acids 462-484 of SEQ ID NO:10 (FIG. 9). This change in structure resulted in a several-fold increase in fusion protein secretion by COS cells, such that it was possible to affinity purify the HIR Ab-L-NAGLU fusion protein (Example 3). The medium IgG level was only 2 ng/mL following transient expression in COS cells of the HIRMAb-NAGLU fusion protein engineered with the (Serine)$_4$ linker (SEQ ID NO: 22), and was increased to 20-28 ng/mL following expression of the HIRMAb-L-NAGLU fusion protein with the 23-amino acid linker derived from the upper hinge domain of human IgG3. In order to increase secretion further, the length of the linker was increased further to 31 amino acids by insertion of the 8-amino acid sequence of the lower hinge domain of the IgG3 hinge region, APEFLGGP (SEQ ID NO: 27), in the original 23-amino acid linker. Any number of variations of linkers may be used as substitutions for the linker, both with respect to amino acid sequence and to amino acid length. The 23-amino acid, or 31-amino acid, linker may be retained, but the amino acid sequence is changed to alternative amino acids, or any number of combinations of the 20 natural amino acids. Or, the linker is reduced from 23-31 amino acids to as low as four amino acids. Such linkers are well known in the art, as there are multiple publicly available programs for determining optimal amino acid linkers in the engineering of fusion proteins. A frequently used linker includes various combinations of Gly and Ser in repeating sequences, such as (Gly$_4$Ser)$_n$ (SEQ ID NO: 28), or other variations.

Example 7

Engineering and Biochemical Properties of HIRMAb-NAGLU Fusion Protein with a 31 Amino Acid Linker In an attempt to further increase secretion of the HIR Ab-NAGLU fusion protein, a new fusion protein with a 31 amino acid linker was engineered. This linker corresponds to the 25 amino acids which comprise the sequence of the human IgG3 hinge region, and is derived from the 12 amino acids of the upper hinge region, followed by 5 amino acids of the first part of the core hinge region, followed by 8 amino acids of the lower hinge region, and is flanked by a Ser-Ser-Ser sequence on the amino terminus and a Ser-Ser-Ser sequence on the carboxyl terminus. The 2 cysteine residues of the first part of the core hinge region are mutated to serine residues, so as to eliminate disulfide bonding. The sequence of the 31-amino acid linker, which is designated the 'LL' linker, is SSSELKTPLGDTTHTSPRSPAPEFLGGPSSS, and corresponds to amino acids 462-492 of SEQ ID NO:18. The double stranded cDNA coding for the LL linker was synthesized by a commercial vendor, and contained HpaI and HindIII sites at the 5'- and 3'-ends, respectively, for insertion into the pHIRMAb-HC expression plasmid (FIG. 4). The ~2.2 kb NAGLU cDNA digested with StuI-HindIII (FIG. 3) was inserted at the HpaI-HindIII site of a HIRMAb-31 amino acid extended linker HC expression vector to form the HIRMAb-31 amino acid extended linker-NAGLU HC expression vector, similar to pHIRMAb-L-NAGLU (FIG. 4), and designated pHIRMAb-LL-NAGLU, wherein the 'LL' linker represents the new 31 amino acid extended linker. The identity of this plasmid was confirmed by bidirectional DNA sequencing, and the nucleotide sequence is given in SEQ ID NO:17, and the deduced amino acid sequence is shown in SEQ ID NO:18. The fusion protein comprised of the HIRMAb heavy chain fused to NAGLU via the LL linker, and the HIRMAb light chain, is designated the HIRMAb-LL-NAGLU fusion protein, and expression of the new HIRMAb-LL-NAGLU fusion protein was investigated in COS cells by co-lipofection using both the pHIRMAb-LL-NAGLU plasmid and the pHIRMAb-LC plasmid. The expression levels in COS cell conditioned medium of the HIRMAb-LL-NAGLU fusion protein were increased, and was up to 5-fold higher than the expression levels of the HIRMAb-L-NAGLU fusion protein, as determined with a human IgG-specific ELISA. To enable stable expression in CHO cells of the HIRMAb-LL-NAGLU fusion protein, a tandem vector (TV) was engineered, which contained genes for i) the HIR Ab LC, ii) the HIRMAb-LL-NAGLU heavy chain fusion protein, and iii) the DHFR selection gene, and this TV is designated the pTV-1980LL vector, and was engineered in a manner similar to that shown for engineering of the pTV-1980L vector (FIG. 4). The HIRMAb HC open reading frame (orf) was deleted form the Universal tandem vector, UTV-1, with NotI and HpaI. In parallel, the HIRMAb-LL-NAGLU HC orf is released from pHIRMAb-LL-NAGLU with NotI and HindIII (blunt) and inserted into the NotI-HpaI sites of pUTV-1 to form pTV-1890LL. The 234 amino acid sequence of the HIR Ab LC is given in SEQ ID NO:8, and the LC is comprised of a 20 amino acid signal peptide followed by a 214 amino acid mature LC. The 714 nucleotide (nt) sequence encoding this LC is given in SEQ ID NO: 13, which is comprised of a 9 nt Kozak sequence (GCCGCCACC), followed by a 702 nt sequence encoding the open reading frame followed by a TAG stop codon. The 1212 amino acid sequence of the HIR Ab HC-LL-NAGLU fusion protein is given in SEQ ID NO:18, and the fusion HC is comprised of a 19 amino acid signal peptide followed by a 1193 amino acid mature fusion HC. The 3,648 nt sequence encoding this fusion HC is given in SEQ ID NO:17, which is comprised of a 9 nt Kozak sequence (GCCGCCACC), followed by a 3,639 nt sequence encoding the open reading frame followed by a TGA stop codon. The 187 amino acid sequence of the DHFR selection protein is given in SEQ ID NO:16. The 573 nt sequence encoding the DHFR is given in SEQ ID NO: 15, which is comprised of a 9 nt Kozak sequence (GCCGCCACC), followed by a 561 nt sequence encoding the open reading frame followed by a TAA stop codon.

For stable expression of the HIRMAb-LL-NAGLU fusion protein in Chinese hamster ovary (CHO) cells were grown in serum free medium, containing 1×HT supplement (hypoxanthine and thymidine). CHO cells (5×10⁶ viable cells) were electroporated with 5 µg PvuI-linearized pTV-1980LL plasmid DNA. The cell-DNA suspension was then incubated for 10 min on ice. Cells were electroporated with a pre-set protocol for CHO cells, i.e. square wave with pulse of 15 msec and 160 volts. After electroporation, cells were incubated for 10 min on ice. The cell suspension was transferred to 50 ml culture medium and plated at 125 µl per well in 4×96-well plates (10,000 cells per well). A total of 10 electroporations and 4,000 wells per electroporation was performed. Following electroporation (EP), the CHO cells were placed in the incubator at 37 C and 8% CO2. Owing to the presence of the neo gene in the TV, transfected cell lines were initially selected with G418. The pTV-1890LL also contains the gene for DHFR, so the transfected cells were also selected with 20 nM methotrexate (MTX) and HT deficient medium. Once visible colonies were detected at about 21 days after EP, the conditioned medium was sampled for human IgG by ELISA. Wells with high human IgG signals in the ELISA were transferred from the 96-well plate to a 24-well plate with 1 mL of HyQ SFM4CHO-Utility. The 24-well plates were returned to the incubator at 37 C and 8% CO2. The following week IgG ELISA was performed on the clones in the 24-well plates. This was repeated through the 6-well plates to T75 flasks and finally to 60 mL and 125 mL square plastic bottles on an orbital shaker. At this stage, the final MTX concentration was 80 nM, and the medium IgG concentration, which was a measure of HIRMAb-LL-NAGLU fusion protein in the medium is >10 mg/L at a cell density of $10^6$ cells/mL. Clones selected for dilutional cloning (DC) were removed from the orbital shaker in the incubator and transferred to the sterile hood. The cells were diluted to 500 mL in F-12K medium with 5% dialyzed fetal bovine serum (d-FBS) and Penicillin/Streptomycin, and the final dilution is 8 cells per mL, so that 4,000 wells in 40×96-well plates can be plated at a cell density of 1 cell per well (CPW). Once the cell suspension was prepared, within the sterile hood, a 125 uL aliquot was dispensed into each well of a 96-well plate using an 8-channel pipettor or a precision pipettor system. The plates were returned to the incubator at 37 C and 8% CO2. The cells diluted to 1 cell/well cannot survive without serum. On day 6 or 7, DC plates were removed from the incubator and transferred to the sterile hood where 125 µl of F-12K medium with 5% dialyzed fetal bovine serum (d-FBS) was added to each well. This selection media now contained 5% d-FBS, 30 nM MTX and 0.25 mg/mL Geneticin. On day 21 after the initial 1 CPW plating, aliquots from each of the 4,000 wells were removed for human IgG ELISA, using robotics equipment. DC plates were removed from the incubator and transferred to the sterile hood, where 100 µl of media was removed per well of the 96-well plate and transferred into a new, sterile sample 96-well plate using an 8-channel pipettor or the precision pipettor system. On day 20 after the initial 1 CPW plating, 40×96-well immunoassay plates were plated with 100 uL of 1 µg/mL solution of primary antibody, a mouse anti-human IgG, in 0.1M NaHCO3. Plates are incubated overnight in the 4 C refrigerator. The following day, the ELISA plates were washed with 1×TBST 5 times, and 100 uL of 1 ug/mL solution of secondary antibody and blocking buffer were added. Plates are washed with 1×TBST 5 times. 100 uL of 1 mg/mL of 4-nitrophenyl phosphate di(2-amino-2-ethyl-1,3-propanediol) salt in 0.1M glycine buffer are added to the 96-well immunoassay plates. Plates were read on a microplate reader. The assay produced IgG output data for 4,000 wells/experiment. The highest producing 24-48 wells were selected for further propagation. The highest producing 24-well plates from the 1 CPW DC were transferred to the sterile hood and gradually subcloned through 6-well dishes, T75 flasks, and 125 mL square plastic bottles on an orbital shaker. During this process the serum was reduced to zero, at the final stage of centrifugation of the cells and resuspension in SFM. The above procedures were repeated with a second round of dilutional cloning, at 0.5-1 cells/well (CPW). At this stage, approximately 40% of the wells showed any cell growth, and all wells showing growth also secreted human IgG. These results confirmed that on average only 1 cell is plated per well with these procedures, and that the CHO cell line originates from a single cell. The HIR Ab-NAGLU fusion protein was secreted to the medium by the stably transfected CHO cells in high amounts at medium concentrations of 10 mg/L at a cell density of 1-2 million cells/mL.

Figure 14:
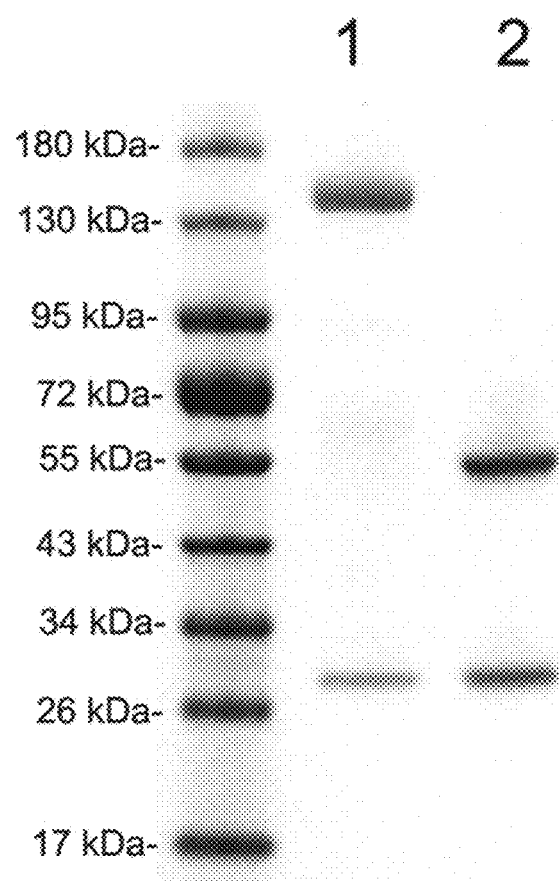
FIG. 14. Reducing SDS-PAGE of molecular weight standards (left side), the purified HIRMAb-LL-NAGLU fusion protein (lane 1) and the purified HIRMAb (lane 2). The HIRMAb-LL-NAGLU fusion protein was produced in CHO cells following stable expression.
Figure 15:
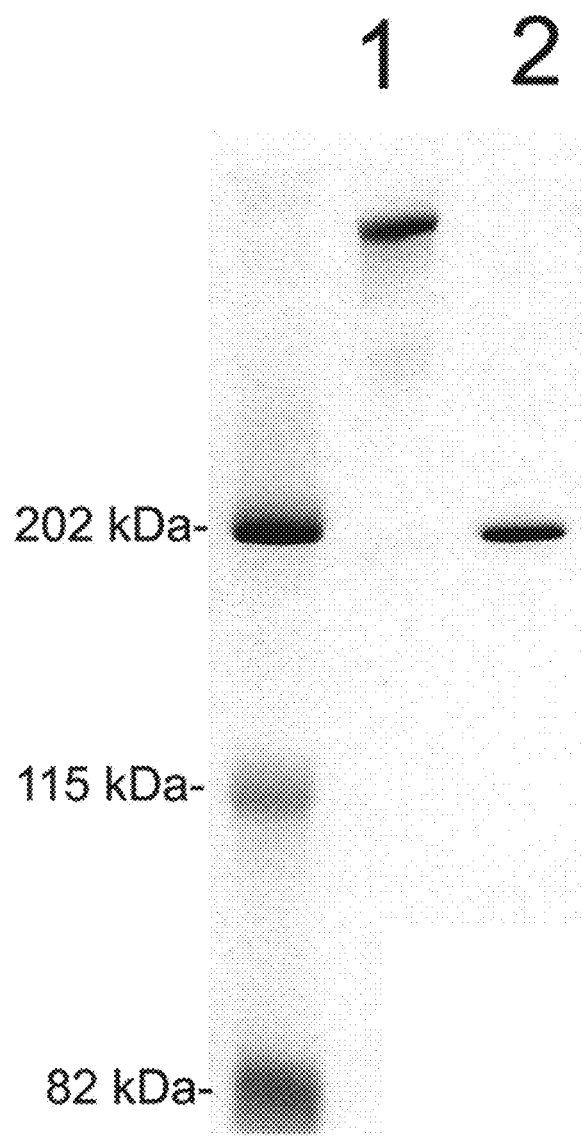
FIG. 15. Non-reducing SDS-PAGE of molecular weight standards (left side), the purified HIRMAb-LL-NAGLU fusion protein (lane 1) and the purified HIRMAb (lane 2). The HIRMAb-LL-NAGLU fusion protein was produced in CHO cells following stable expression.
Figure 16:
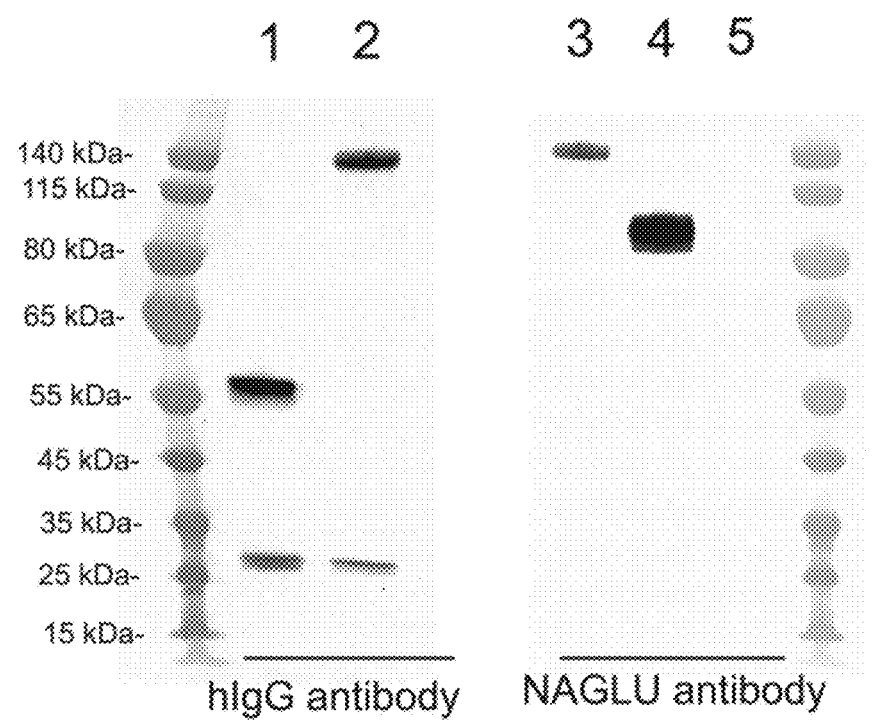
FIG. 16. Western blot with either anti-human (h) IgG primary antibody (left panel) or anti-human NAGLU primary antiserum (right panel). The immunoreactivity of the HIRMAb-LL-NAGLU fusion protein (lanes 2 and 3) is compared to the chimeric HIRMAb (lanes 1 and 5) and to recombinant NAGLU (lane 4). Both the HIRMAb-LL-NAGLU fusion protein and the HIRMAb have identical light chains on the anti-hIgG Western. The HIRMAb-LL-NAGLU fusion heavy chain reacts with both the anti-hIgG and the anti-human NAGLU antibody, whereas the HIRMAb heavy chain only reacts with the anti-hIgG antibody. The recombinant NAGLU reacts only with the anti-human NAGLU antibody. The HIRMAb-LL-NAGLU fusion protein was produced in CHO cells following stable expression.
Figure 17:
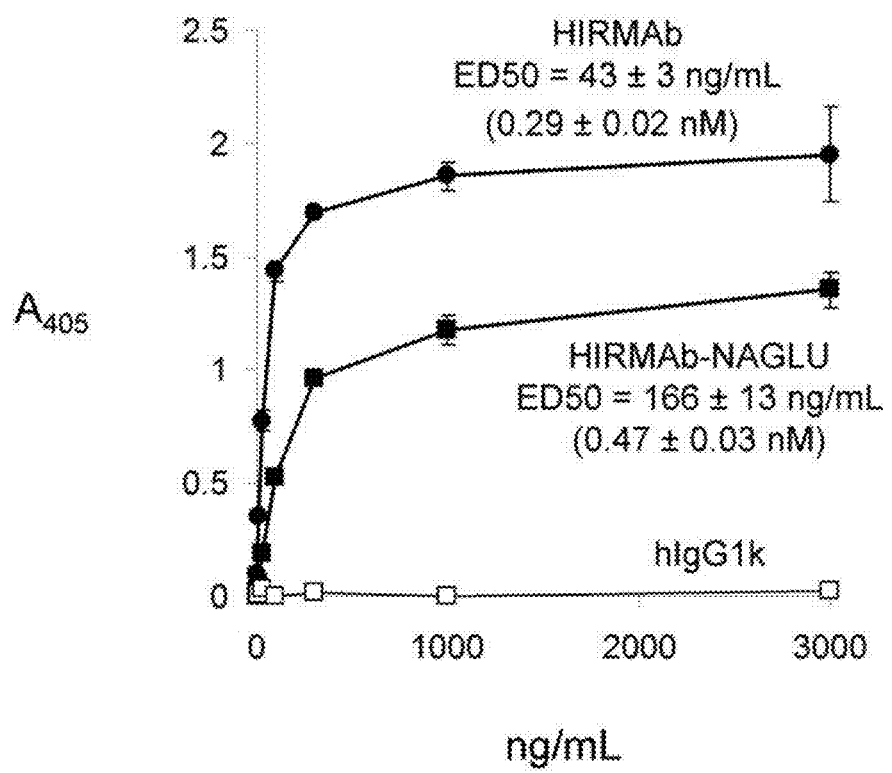
FIG. 17. Binding of either the chimeric HIRMAb or the HIRMAb-LL-NAGLU fusion protein to the HIR extracellular domain (ECD) is saturable. The $ED_{50}$ of HIRMAb-LL-NAGLU binding to the HIR ECD is 166±13 ng/mL, which is 0.44±0.03 nM, based on a MW of 375 kDa. This is comparable to the $ED_{50}$ of the binding of the chimeric HIRMAb, 43±3 ng/mL, which is 0.29±0.02 nM, based on a MW of 150 kDa. The HIRMAb-LL-NAGLU fusion protein was produced in CHO cells following stable expression.

The HIRMAb-LL-NAGLU fusion protein was affinity purified from the CHO cell conditioned SFM by protein A affinity chromatography. The purity of the CHO-derived HIRMAb-LL-NAGLU fusion protein was verified by reducing SDS-PAGE as shown in FIG. 14, and by non-reducing SDS-PAGE, as shown in FIG. 15. In the SDS-PAGE shown in FIGS. 14-15, the HIRMAb-LL-NAGLU fusion protein is applied to lane 1, and the non-fused HIRMAb alone is applied to lane 2. Only the HC and LC proteins are detected for either the HIRMAb alone or the HIRMAb-LL-NAGLU fusion protein. The identity of the CHO-derived fusion protein was verified by Western blotting using primary antibodies to either human IgG (FIG. 16, left panel) or human NAGLU (FIG. 16, right panel). The proteins applied to lanes 1 and 2 of the human IgG blot (FIG. 16, left panel) are the HIRMAb alone, and the HIRMAb-LL-NAGLU fusion protein. The proteins applied to lanes 1, 2, and 3 of the human NAGLU blot (FIG. 16, right panel) are the HIRMAb-LL-NAGLU fusion protein, commercially available human recombinant NAGLU alone, and the HIRMAb alone, respectively. The anti-human IgG antibody reacts with both HC and LC of the HIRMAb-LL-NAGLU fusion protein and the HIRMAb alone (FIG. 16, left panel). The anti-NAGLU antibody reacts only with the HC of the HIRMAb-LL-NAGLU fusion protein and with the recombinant NAGLU, but does not react with either the HIRMAb alone, or with the LC of the HIRMAb-LL-NAGLU fusion protein (FIG. 16, right panel). The molecular weight (MW) of the HIRMAb-LL-NAGLU heavy and light chains, and the MW of the HIRMAb heavy and light chains are estimated by linear regression based on the migration of the MW standards. The size of the HIRMAb-LL-NAGLU fusion heavy chain, 146 kDa, is larger than the size of the heavy chain of the HIRMAb, 54 kDa, owing to the fusion of the NAGLU to the HIRMAb heavy chain. The size of the light chain, 25 kDa, is identical for both the HIRMAb-LL-NAGLU fusion protein and the HIRMAb antibody, as both proteins use the same light chain. The estimated MW of the hetero-tetrameric HIRMAb-LL-NAGLU fusion protein shown in FIG. 2 is 350 kDa, based on migration in the reducing SDS-PAGE of the Western blot. The estimated MW of the recombinant human NAGLU is 105 kDa, based on migration in the reducing SDS-PAGE of the Western blot (FIG. 16, right panel). The large difference in molecular size of the HIRMAb-LL-NAGLU fusion protein, and the HIRMAb alone is shown with the non-reducing SDS-PAGE in FIG. 15. The affinity of the CHO-derived HIRMAb-LL-NAGLU fusion protein for the HIR ECD was determined with an ELISA, and the lectin affinity purified HIR ECD derived from the serum free medium of CHO cells stably transfected with the gene encoding the HIR ECD. The concentration of either HIR Ab or HIRMAb-LL-NAGLU fusion protein that gave 50% maximal binding, ED50, was determined by non-linear regression analysis. The ED50 of HIR binding by the HIRMAb alone is 43±3 ng/mL and the ED50 of HIR binding by the HIRMAb-LL-NAGLU fusion protein is 166±13 ng/mL (FIG. 17). The MW of the HIRMAb alone is 150 kDa, and the MW of the CHO-derived HIRMAb-LL-NAGLU fusion protein is 350 kDa. Therefore, after normalization for MW differences, there was comparable binding of either the HIRMAb alone or the HIRMAb-LL-NAGLU fusion protein for the HIR ECD with ED50 of 0.29±0.02 nM and 0.47±0.03 nM, respectively (FIG. 17). These findings show that the affinity of the HIRMAb-LL-NAGLU fusion protein binding to the HIR is retained, despite fusion of a NAGLU molecule to the carboxyl termini of both heavy chains of the IgG via the extended LL linker. The NAGLU enzyme activity of the HIRMAb-LL-NAGLU fusion protein was determined with the fluorometric enzyme assay using the 4MUαGlcNAc substrate, and assay conditions described above for the COS-derived HIRMAb-L-NAGLU fusion protein. In addition, the NAGLU enzyme activity of the HIRMAb-LL-NAGLU fusion protein was compared to the activity of recombinant human NAGLU produced in CHO cells and commercially available (R&D Systems). The NAGLU enzyme activity of the CHO-derived HIRMAb-LL-NAGLU fusion protein was 74,200±2,200 units/mg protein, where 1 unit=1 nmol/hr at 37 C. The NAGLU enzyme activity of recombinant NAGLU was 123,900±2,500 units/mg protein using the same assay. However, the MW of the CHO-derived HIRMAb-LL-NAGLU fusion protein is larger than the MW of the recombinant NAGLU. There are 2 NAGLU domains per hetero-tetramer (FIG. 2); therefore the effective MW of the NAGLU fusion protein is half of 350 kDa, or 175 kDa, which is 75% higher than the MW of the NAGLU. Therefore, after normalization for MW differences, the NAGLU enzyme activity of the HIRMAb-LL-NAGLU fusion protein is at least as high as recombinant NAGLU alone.

Example 8

Figure 18:
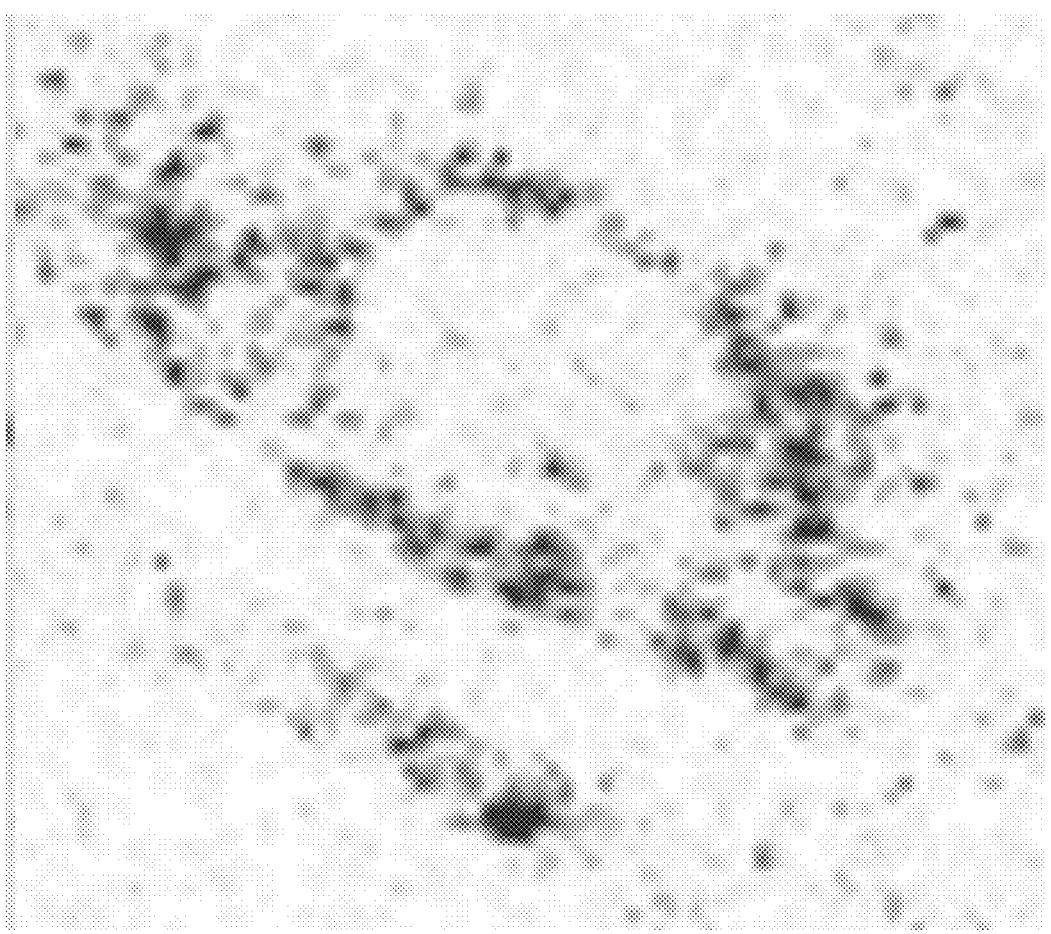
FIG. 18. Inverted grayscale image of confocal micrograph of Sanfilippo Type B, or MPSIIIB, fibroblasts, shows uptake of the HIRMAb-LL-NAGLU fusion protein into intracellular organelles of the cell. The MPSIIIB fibroblasts were fixed after a 24 hour incubation with the HIRMAb-LL-NAGLU fusion protein, and then immuno-stained with an antibody against human NAGLU. In addition, the cells were co-immuno-stained with an antibody against the lysosomal associated membrane protein (LAMP)-1. The NAGLU and LAMP-1 immuno-staining were viewed in the red and green channels, respectively. The overlap channel in yellow shows co-localization of the intracellular HIRMAb-LL-NAGLU fusion protein with the lysosomal LAMP-1 in the lysosomal compartment.

Targeting of NAGLU to Lysosomal Compartment in Sanfilippo Type B Human Fibroblasts Via Receptor-Mediated Intracellular Delivery MPSIIIB human fibroblasts were incubated with 10 ug/mL HIRMAb-LL-NAGLU fusion protein for 24 hours followed by fixation and immune labeling with an antibody against lysosomal associated membrane protein (LAMP)-1, a lysosomal marker, and a second antibody to human NAGLU. The cells were then washed, fixed, and examined under a confocal microscope. LAMP1 immunoreactivity within the cell was detected in the green channel, and the NAGLU immunoreactivity was detected in the red channel. An inverted grayscale image of the NAGLU immunoreactivity is shown in FIG. 18, which shows the HIRMAb-LL-NAGLU fusion protein has been taken up by the MPSIIIB cell and triaged into intracellular organelles. The overlap of the NAGLU and LAMP1 immunoreactivity was detected in the yellow channel, and the majority of the organelles that were immuno-positive for NAGLU were also immuno-stained for LAMP-1. These results show the HIRMAb-LL-NAGLU fusion protein is taken up by MPSIIIB cells and triaged to the lysosomal compartment. The time-response of the intracellular distribution of the HIRMAb-LL-NAGLU fusion protein into MPSIIIB fibroblasts was examined by measurement of intracellular NAGLU enzyme activity in the MPSIIIB cells that were exposed to the HIRMAb-LL-NAGLU fusion protein. The cells were treated with 6 ug/mL (16 nM) of the HIRMAb-LL-NAGLU fusion protein, which was added to the culture medium for 0 to 30 hours. The cells were then washed, and the NAGLU enzyme activity in the intracellular lysate was measured with the NAGLU enzymatic fluorometric assay described previously using the 4MUαGlcNAc assay substrate. As shown in Table 2, there is a time-dependent increase in intracellular NAGLU enzyme activity. Conversely, no NAGLU enzyme activity is detected in the untreated MPSIIIB fibroblasts (Table 2). A dose-response study was also performed. The MPSIIIB fibroblasts were incubated for 4 hours with either 0 to 50 nM

TABLE 2

Intracellular NAGLU enzyme activity in MPSIIIB fibroblasts treated with the HIRMAb-LL-NAGLU fusion protein

| Incubation time (hours) | Intracellular NAGLU activity (units/mg protein) |
|---|---|
| none | <0.3 |
| 2 | 0.86 ± 0.11 |
| 4 | 2.66 ± 0.40 |
| 24 | 4.14 ± 0.48 |
| 30 | 5.41 ± 0.74 |

Mean ± SE (N = 3 dishes); 1 unit = 1 nmol/hour. The fusion protein was added to the medium and the fibroblasts were incubated for 2-30 hours at 37° C., followed by washing, and determination of intracellular NAGLU enzyme activity.

HIRMAb-LL-NAGLU fusion protein, or 0 to 50 nM commercially available human recombinant NAGLU, followed by measurement of intracellular NAGLU enzyme activity using the fluorometric enzyme assay (Table 3). A saturation of uptake of the HIRMAb-LL-NAGLU fusion protein was observed at a 25 nM concentration of the fusion protein; conversely, there was no increase in intracellular NAGLU enzyme activity following the addition of NAGLU alone (Table 3). The NAGLU enzyme activity of the human recombinant NAGLU was high and comparable to the enzyme activity of the HIRMAb-LL-NAGLU fusion

TABLE 3

Intracellular NAGLU enzyme activity in MPSIIIB fibroblasts treated with either the HIRMAb-LL-NAGLU fusion protein or with recombinant human NAGLU

| Enzyme Treatment | Intracellular NAGLU activity (units/mg protein) |
|---|---|
| none | <0.1 |
| 12.5 nM HIRMAb-LL-NAGLU | 0.54 ± 0.28 |
| 25 nM HIRMAb-LL-NAGLU | 1.05 ± 0.24 |
| 37.5 nM HIRMAb-LL-NAGLU | 0.89 ± 0.28 |
| 50 nM HIRMAb-LL-NAGLU | 0.84 ± 0.22 |
| 10 nM NAGLU | <0.1 |
| 25 nM NAGLU | <0.1 |
| 50 nM NAGLU | <0.1 |

Figure 19:
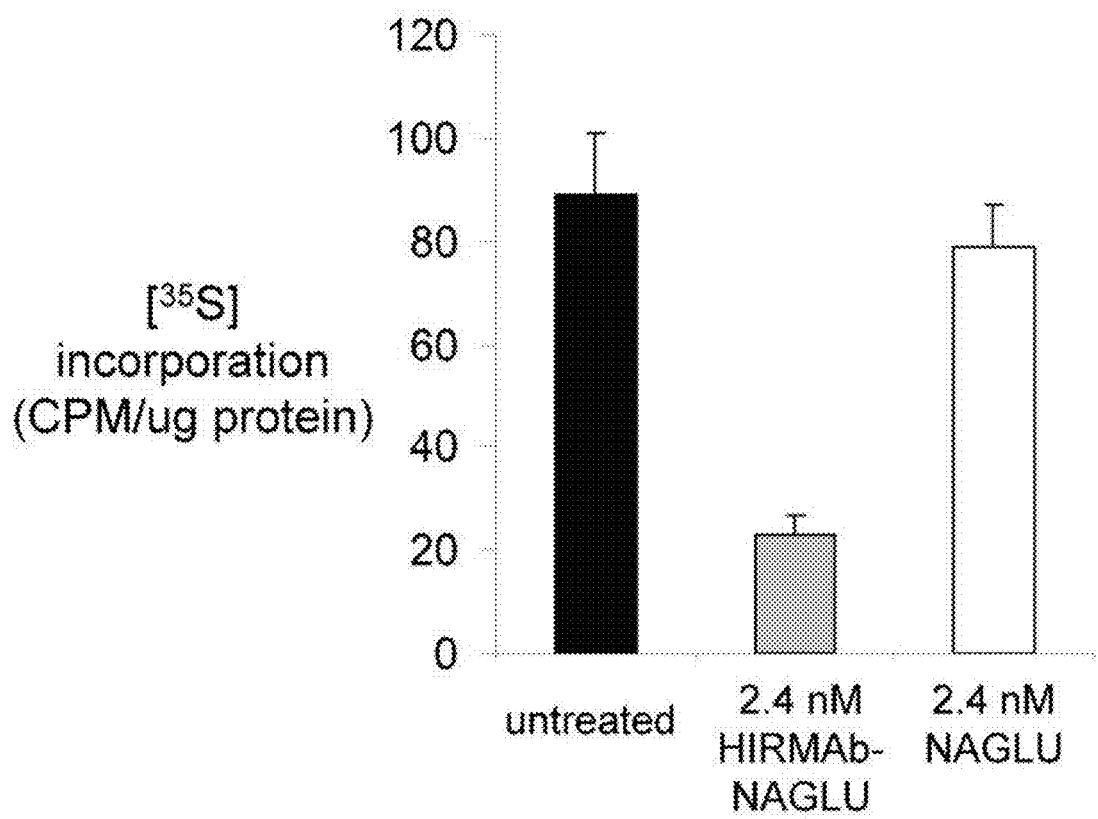
FIG. 19. Sanfilippo Type B, or MPSIIIB, fibroblasts were pulsed with $^{35}$S-sulfate, which is incorporated into intracellular sulfated GAGs over a 48 hr period. In a chase experiment, the cells were either untreated or exposed to 2.4 nM HIRMAb-LL-NAGLU fusion protein for 2 hours or to 2.4 nM recombinant human NAGLU for 2 hours, followed by washing, replacement with fresh medium without enzyme, and were incubated an additional 48 hours. The intracellular $^{35}$S radioactivity was then determined and expressed as CPM per ug protein per well. Data are mean±SE (N=4).

Mean ± SE (N = 3 dishes); 1 unit = 1 nmol/hour. The enzyme was added to the medium and the fibroblasts were incubated for 4 hours at 37° C., followed by washing, and determination of intracellular NAGLU enzyme activity.

protein, as described above. The low uptake of the NAGLU by the MPSIIIB fibroblasts is due to the lack of incorporation of mannose-6-phosphate (M6P) in the recombinant form of this lysosomal enzyme [Zhao et al (1996), "The molecular basis of Sanfilippo syndrome type B," Proc. Natl. Acad. Sci., U.S.A., 93: 6101-6105]. Consequently, NAGLU is poorly taken up by human fibroblasts via the M6P receptor (M6PR). Conversely, the HIRMAb-LL-NAGLU fusion protein is able to penetrate the MPSIIIB cells owing to uptake via the insulin receptor, which is well known to be expressed in human fibroblasts. The differential uptake of the NAGLU alone vs the HIRMAb-LL-NAGLU fusion protein in MPSIIIB cells has a functional significance, as the accumulation of intracellular GAGs is reduced by treatment of the cells with the HIRMAb-LL-NAGLU fusion protein, but not by treatment with the recombinant human NAGLU (FIG. 19). The MPSIIIB fibroblasts were pulsed with $^{35}$S-sulfate, which is incorporated into intracellular sulfated GAGs over a 48 hr period. In the chase phase of the experiment, the cells were either untreated or exposed to 2.4 nM HIRMAb-NAGLU fusion protein for 2 hours or to 2.4 nM recombinant human NAGLU for 2 hours, followed by washing, replacement with fresh medium without enzyme, and were incubated an additional 48 hours. The intracellular $^{35}$S radioactivity was then determined and expressed as CPM per ug protein per well. There is a 90% reduction in intracellular GAGs caused by treatment with the HIRMAb-LL-NAGLU fusion protein (FIG. 19). Conversely, there is no significant reduction in intracellular GAGs caused by treatment with NAGLU alone (FIG. 19).

Example 9

Engineering of HIRMAb-NAGLU Fusion Protein with Truncated Enzyme Amino Terminus

The amino terminus of the mature human NAGLU, minus the signal peptide, begins with the DEAR sequence corresponding to amino acids 1-4 of SEQ ID NO:9, following production in either CHO cells or purified from human placenta [Zhao et al (1996), "The molecular basis of Sanfilippo syndrome type B," Proc. Natl. Acad. Sci., USA., 93: 6101-6105, and Weber et al (1996), "Cloning and expression of the gene involved in Sanfilippo B syndrome (mucopolysaccharidosis IIIB), Human Molecular Genetics, 5: 771-777]. An amino terminal truncated form of human NAGLU was also isolated from human placenta, which begins with the KPGL sequence corresponding to amino acids 36-39 of SEQ ID NO:9 [Weber et al (1996), "Cloning and expression of the gene involved in Sanfilippo B syndrome (mucopolysaccharidosis IIIB), Human Molecular Genetics, 5: 771-777]. The significance of the N-terminal sequence heterogeneity of purified human placental NAGLU is not known, nor is it known whether the NAGLU enzyme is normally processed within the cell from a 720 amino acid precursor to a 685 amino acid mature form. The stability of HIRMAb-LL-NAGLU fusion protein was verified by incubation of the fusion protein in Rhesus monkey plasma. The HIRMAb-LL-NAGLU fusion protein was diluted at 0.25 ug/uL in Tris buffer saline and 50% Rhesus monkey plasma and incubated at 37 C for 0, 1, 2 and 4 hours. Aliquots of the incubated plasma were resolved by reducing SDS-PAGE and blotted onto nitrocellulose for Western blot testing. The Western blotting was performed with a rabbit anti-human NAGLU polyclonal antibody as the primary antibody, and a biotinylated goat anti-rabbit IgG as secondary antibody. A single band of approximately 140 kDa corresponding to the heavy chain of the HIRMAb-LL-NAGLU fusion protein was seen in the control (e.g. HIRMAb-LL-NAGLU fusion protein reference standard), and in all samples incubated with Rhesus plasma for up to 4 hours. This study shows that the HIRMAb-LL-NAGLU fusion protein is stable in Rhesus plasma and not subjected to cleavage and separation of the NAGLU domain from the IgG domain.

So as to allow for an evaluation of the properties of the amino terminal truncated version of NAGLU, the gene was engineered that allowed for expression of the HIRMAb-LL-NAGLU fusion protein, where the 35 amino acids of the N-terminus of the mature form of human NAGLU were removed from the fusion protein. A cDNA encoding human NAGLU without either the signal peptide or the putative 35 amino acid propeptide was generated by PCR. The latter was completed using the pHIRMAb-LL NAGLU expression vector as template and forward and reverse ODN primers. The sequence of the forward primer is 5'-phophate-CCAAGCCCGGGCTGGACACCTACAGCCTG-3', which corresponds to nucleotides 114-140 of SEQ ID NO:11. The forward primer is 5'-phosphorylated for direct insertion into the HpaI site of expression vector and contains 'CC' nucleotides at the 5'-end to maintain the open reading frame with the CH3-linker end of the gene within the expression vector. The reverse ODN primer sequence is 5'-GAGTGGCACCT-TCCAGGGTCAAG-3' (SEQ ID NO: 29), and is complementary to the poly-A region located on the 3'-flanking region of NAGLU cDNA. The ~2.2 kb PCR product was digested with HindIII and gel-purified. The latter was inserted at the HpaI-HindIII site of the pHIRMAb-LL expression vector to form a new expression vector designated pHIRMAb-LL-NAGLU-del, and the fusion protein produced by this expression plasmid DNA is designated HIRMAb-LL-NAGLU-del. The identity of this plasmid was confirmed by bidirectional DNA sequencing, and the nucleotide sequence is given in SEQ ID NO:19, and the gene is comprised of 3,540 nucleotides, which includes a 9 nt Kozak sequence (GCCGCCACC), followed by a 3,531 nt sequence encoding the open reading frame followed by a TGA stop codon. The deduced amino acid sequence of the heavy chain of the HIRMAb-LL-NAGLU-del fusion protein is shown in SEQ ID NO:20. The fusion protein is comprised of 1176 amino acids, which include a 19 amino acid signal peptide, a 442 amino acid HIRMAb heavy chain, a 30 amino acid LL linker, and a 685 amino acid NAGLU without the 35 amino acid propeptide. The LL linker was reduced to 30 amino acids, as the C-terminal end of the LL linker in this construct terminates in Ser-Ser.

Example 10

Figure 20:
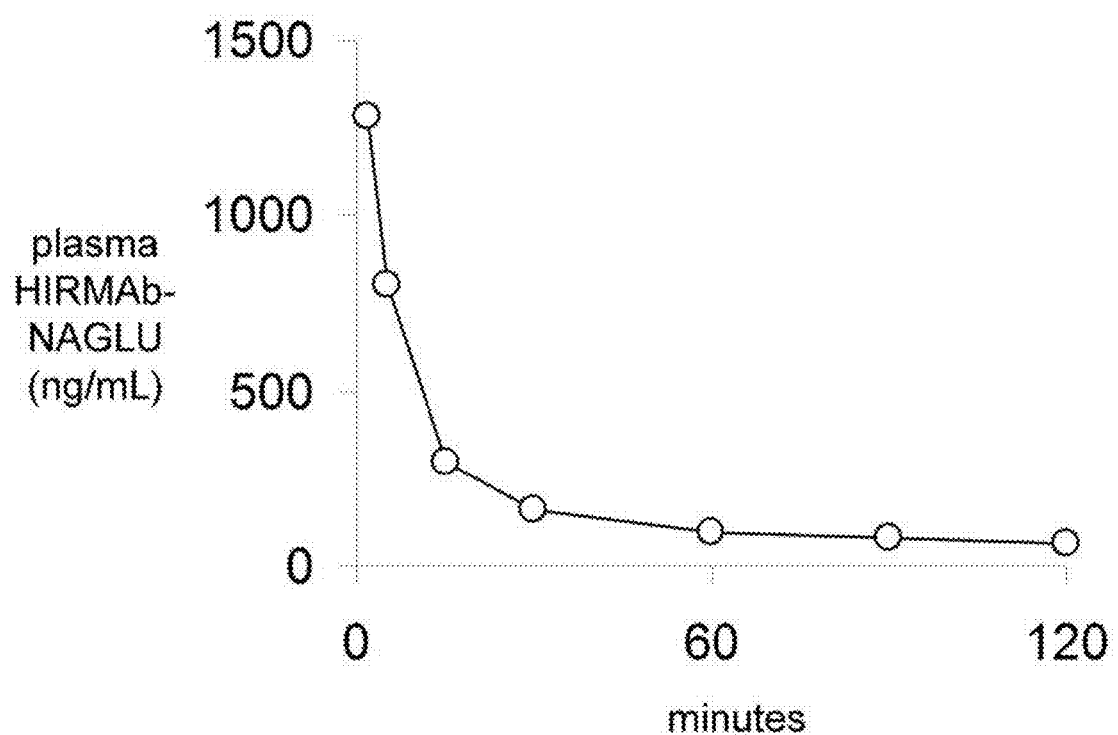
FIG. 20. Plasma concentration the HIRMAb-LL-NAGLU fusion protein in a 4.2 kg adult Rhesus monkey following IV injection of a 81 ug/kg dose of the fusion protein.

Delivery of HIRMAb-NAGLU Fusion Protein to Brain and Peripheral Organs in the Adult Non-Human Primate The HIRMAb-LL-NAGLU fusion protein was radiolabeled with the [$^{125}$I]-Bolton-Hunter reagent to a specific activity (SA) of 5.6 uCi/ug. Following purification and separation from unreacted reagent, the radiochemical purity of the labeled fusion protein was demonstrated by a high trichloroacetic acid (TCA) precipitability of >98%. Within 2 days of radiolabeling, the [$^{125}$I]-HIRMAb-LL-NAGLU fusion protein was injected intravenously (IV) into a adult 4.2 kg rhesus monkey at an injection dose (ID) of 1900 uCi, which is equivalent to an ID of 339 ug or 81 ug/kg of the [$^{125}$I]-HIRMAb-LL-NAGLU fusion protein. The plasma concentration of the fusion protein was determined from the SA of the fusion protein and the plasma concentration of TCA-precipitable radioactivity, and the plasma profile of the [$^{125}$I]-HIRMAb-LL-NAGLU fusion protein in the primate is shown in FIG. 20, which reveals a rapid plasma clearance of the fusion protein. Size exclusion chromatography of the 2 minute and 60 minute plasma showed comparable profiles, which provides evidence that the NAGLU domain of the fusion protein is not cleaved from the heavy chain of the HIRMAb domain of the fusion protein. The plasma profile in FIG. 20 was fit to a bi-exponential equation to determine the plasma pharmacokinetic (PK) parameters, and these are given in Table 4:

TABLE 4

Pharmacokinetic parameters of the [$^{125}$I]-HIRMAb-LL-NAGLU fusion protein

| parameter | units | value |
|---|---|---|
| $T\frac{1}{2}^1$ | min | 4.5 ± 0.4 |
| $T\frac{1}{2}^2$ | min | 79 ± 12 |
| MRT | min | 78 ± 12 |
| Vc | mL/kg | 50 ± 3 |
| Vss | mL/kg | 219 ± 23 |
| AUCss | ug · min/mL | 29.2 ± 1.4 |
| CL | mL/min/kg | 2.76 ± 0.12 |

Parameters computed from the plasma profile in FIG. 20. $T\frac{1}{2}^1$ and $T\frac{1}{2}^2$ are the half-times of plasma clearance for the first phase (alpha) and second phase (beta) phases.

The systemic volume of distribution, Vss, is over 4-fold higher than the central volume, Vc, which is indicative of rapid uptake of the fusion protein by peripheral tissues, which are mainly liver, spleen, and lung, as shown in Table 5:

TABLE 5

Organ uptake of the [$^{125}$I]-HIRMAb-LL-NAGLU fusion protein in the Rhesus monkey

| organ | Organ uptake (% ID/100 grams) |
|---|---|
| Frontal cortex | 1.03 ± 0.07 |
| Cerebellar cortex | 1.05 ± 0.04 |
| Choroid plexus | 0.20 ± 0.05 |
| liver | 32.8 ± 1.4 |
| spleen | 15.9 ± 0.7 |
| lung | 3.5 ± 0.2 |
| heart | 1.2 ± 0.1 |
| fat | 0.93 ± 0.03 |
| Skeletal muscle | 0.24 ± 0.03 |

Data are mean ± SD of triplicate samples.

The uptake of the [$^{125}$I]-HIRMAb-LL-NAGLU fusion protein by brain is 1% ID/100 grams brain (Table 5). Uptake is expressed per 100 grams brain, because the weight of the brain in the adult Rhesus monkey is 100 grams. While the brain uptake is less than the organ uptake in liver, spleen, or lung, a brain uptake of 1% ID/brain for a protein molecule is very high. In contrast, the brain uptake of a [$^{125}$I]-Bolton-Hunter reagent labeled lysosomal enzyme, that does not cross the BBB, is <0.03% ID/brain [Boado et al, Blood-brain barrier molecular Trojan horse enables brain imaging of radioiodinated recombinant protein in the Rhesus monkey. *Bioconj. Chem.*, 24:1741-1749, 2013)]. The high brain uptake of the [$^{125}$I]-HIRMAb-LL-NAGLU fusion protein does not represent simple binding/sequestration to the vascular compartment of the brain. As shown by the capillary depletion method, the distribution of the [$^{125}$I]-HIRMAb-LL-NAGLU fusion protein into the post-vascular supernatant of brain is high relative to the distribution in the vascular pellet (Table 6):

TABLE 6

Capillary depletion analysis of the brain uptake of the [$^{125}$I]-HIRMAb-NAGLU fusion protein

| Molecule | Brain fraction | VD (µL/g) |
|---|---|---|
| HIRMAb-NAGLU fusion protein | Brain homogenate | 337 ± 37 |
|  | Post-vascular supernatant | 214 ± 9 |
|  | Vascular pellet | 55 ± 16 |
| Human IgG1 isotype control | Brain homogenate | 20 ± 6 |

Mean ± S.D. The fusion protein was administered by IV injection, and brain measurements made 120 min following injection. The radioactivity in the post-vascular supernatant was 93.1 ± 0.8% precipitable by cold 10% trichloroacetic acid.

The finding of the very high uptake of the [$^{125}$I]-HIRMAb-LL-NAGLU fusion protein by the primate brain enables dosing of the MPSIIIB patient such that the IV infusion dose of the fusion protein in patients with MPSIIIB can restore NAGLU enzyme activity in the brain of such patients.

Example 11

Receptor-Mediated Delivery of NAGLU to the Human Brain

Sanfilippo Type B, or MPS-IIIB, is a lysosomal storage disorder caused by defects in the gene encoding the lysosomal enzyme, NAGLU. In the absence of NAGLU, certain GAGs such as heparan sulfate accumulate in the cells. The accumulation of the heparan sulfate in the brain leads to the clinical manifestations of MPS-IIIB, which includes severe behavioral disturbances, loss of speech in childhood, impaired walking leading to wheelchair existence, and death as young adults [Heron et al (2011): Incidence and natural history of Mucopolysaccharidosis Type III in France and Comparison with United Kingdom and Greece. Am. J. Med. Genet. Part A, 155: 58-68].

The nucleotide sequence of the NAGLU mRNA and the amino acid sequence of the human NAGLU protein is known [Zhao et al (1996) and Weber et al (1996)]. This sequence enables the production of recombinant NAGLU for the enzyme replacement therapy (ERT) of MPS-IIIB. NAGLU produced in Chinese hamster ovary (CHO) cells has a specific activity of at least 30,000 units/mg enzyme [Weber et al (1996)]. The problem with ERT of MPS-IIIB with recombinant NAGLU is that NAGLU, like other large molecule pharmaceuticals, does not cross the BBB [DiNatale et al (2005)]. In addition, recombinant NAGLU incorporates mannose 6-phosphate (M6P) poorly, which restricts uptake by tissues in peripheral organs that is mediated by the M6P receptor (M6PR) [Weber et al (2001) Expression and characterization of human recombinant α-N-acetylglucosaminidase, Prot. Exp. Purif. 21, 251-259.] The M6PR also transport insulin-like growth factor (IGF)-2, and a fusion protein of NAGLU and IGF-2 is taken up by MPSIIIB cells in culture [Kan et al (2014): Delivery of an enzyme-IGFII fusion protein to the mouse brain is therapeutic for mucopolysaccharidosis type IIIB, Proc. Natl. Acad. Sci., 111: 14870-148751. However, the IGF-2 domain does not mediate transport across the BBB. Accordingly, intravenous ERT in MPS-IIIB patients with recombinant NAGLU, or a NAGLU-IGF2 fusion protein, is not expected to have any beneficial effect on the brain. For example, in order to treat the brain of the MPSIIIB mouse with the NAGLU-IGF2 fusion protein, it was necessary to inject the fusion protein into the brain via an invasive intra-cerebroventricular (ICV) injection (Kan et al, 2014). The ICV route of drug delivery to the brain is well known to distribute drug only to the ependymal and meningeal surface of the brain, particularly in animals larger than mice where diffusion distances are increased.

ICV enzyme administration is an invasive procedure that requires implantation of chronic catheter into the brain. The preferred approach to the delivery of NAGLU to the brain of MPS-IIIB patients is via an intravenous infusion of a form of NAGLU that is re-engineered to cross the BBB via receptor-mediated transport (RMT). The HIRMAb-NAGLU fusion protein retains high affinity binding to the human insulin receptor, which enables the NAGLU to penetrate the BBB and enter brain from blood via RMT on the endogenous BBB insulin receptor. The brain uptake of the HIRMAb-NAGLU fusion protein is 1% of injected dose (ID) per brain (Table 5). If the therapeutic dose of the HIR Ab-NAGLU fusion protein is 1 mg/kg, the body weight is 50 kg, and the enzyme specific activity is 100,000 units/mg, then the infusion dose (ID) of the fusion protein is 5 million units. Given a brain uptake of the fusion protein of 1% of the ID, then the brain NAGLU enzyme activity is 50,000 units per 1000 gram human grain, or 50 units/gram. Given 100 mg protein per gram brain, the brain NAGLU enzyme activity is 0.5 units/mg protein, which is 70% of the normal NAGLU enzyme activity in the monkey brain [Murrey et al (2014): Feasibility and safety of systemic rAAV9-hNAGLU delivery for treating Mucopolysaccharidsosis IIIB: toxicology, biodistribution, and immunological assessments in primates, Human Gene Therapy, 25: 72-84.] This level of brain enzyme replacement of NAGLU is more than enough for a therapeutic response. Enzyme replacement therapy in patients with lysosomal storage disorders that produces a cellular enzyme activity of just 1-2% of normal do not develop signs and symptoms of the disease (J. Muenzer and A. Fisher, Advances in the treatment of mucopolysaccharidosis type I, N. Engl J Med, 350: 1932-1934, 2004). These considerations show that a clinically significant NAGLU enzyme replacement of the human brain is possible following the intravenous infusion of the HIRMAb-NAGLU fusion protein at a systemic dose of approximately 1 mg/kg.

What is claimed:

1. A fusion antibody comprising: (a) a fusion protein comprising the amino acid sequences of an immunoglobulin heavy chain (Ig-HC) of an anti-human insulin receptor antibody (HIR Ab), a linker and an alpha-N-acetylglucosaminidase (NAGLU); wherein the carboxyl terminus of the Ig-HC is linked to the amino terminus of the NAGLU through the linker; and wherein the amino acid sequence of the Ig-HC is the amino acid sequence of SEQ ID NO: 7; the amino acid sequence of the NAGLU is the amino acid sequence of SEQ ID NO:9; and the amino acid sequence of the linker comprises amino acids 462-484 of SEQ ID NO:10 or amino acids 462-492 of SEQ ID NO:18; and (b) an immunoglobulin light chain (Ig-LC) of the HIR Ab comprising the amino acid sequence of SEQ ID NO:8; wherein the fusion antibody crosses the blood brain barrier (BBB) and wherein the NAGLU retains at least 20% of its activity compared to its activity as a separate entity.

2. The fusion antibody of claim 1, wherein the NAGLU specific activity of the fusion antibody is at least about 10000 units/mg.

3. The fusion antibody of claim 1, wherein the immunoglobulin heavy chain comprises a complementarity-determining region 1 (CDR1) corresponding to the amino acid sequence of SEQ ID NO:1, a complementarity-determining region 2 (CDR2) corresponding to the amino acid sequence of SEQ ID NO:2, or a complementarity-determining region 3 (CDR3) corresponding to the amino acid sequence of SEQ ID NO:3.

4. The fusion antibody of claim 1, wherein the immunoglobulin light chain comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

5. A fusion antibody comprising: (a) a fusion protein comprising the amino acid sequences of an Ig-HC of an anti-human insulin receptor antibody (HIR Ab) and an alpha-N-acetylglucosaminidase (NAGLU); wherein the fusion protein comprises the amino acid sequence of SEQ ID NO: 10, 18 or 20; and (b) an Ig-LC of the HIR Ab comprising the amino acid sequence of SEQ ID NO:8; wherein the fusion antibody crosses the blood brain barrier (BBB); and wherein the NAGLU retains at least 20% of its activity compared to its activity as a separate entity.

6. A method for increasing alpha-N-acetylglucosaminidase (NAGLU) activity in a subject suffering from NAGLU deficiency in the central nervous system, comprising systemically administering to the subject a therapeutically effective dose of a fusion antibody according to claim 1.

7. The method of claim 6, wherein the therapeutically effective dose comprises at least about 10,000 units/kg of body weight.

8. The method of claim 6, wherein the NAGLU specific activity of the fusion antibody is at least 10,000 units/mg.

9. The method of claim 6, wherein the immunoglobulin heavy chain comprises a complementarity-determining region 1 (CDR1) corresponding to the amino acid sequence of SEQ ID NO: 1, a complementarity-determining region 2 (CDR2) corresponding to the amino acid sequence of SEC) ID NO:2, or a complementarity-determining region 3 (CDR3) corresponding to the amino acid sequence of SEC) ID NO:3.

10. The method of claim 6, wherein the immunoglobulin light chain comprises a CDR1 corresponding to the amino acid sequence of SEC) ID NO:4, a CDR2 corresponding to the amino acid sequence of SEQ ID NO: 5, or a CDR3 corresponding to the amino acid sequence of SEQ ID NO:6.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Gly Tyr Thr Phe Thr Asn Tyr Asp Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Tyr Pro Gly Asp Gly Ser Thr Lys Tyr Asn Glu Lys Phe Lys
1               5                   10                  15

Gly

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Trp Ala Tyr
1

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asp Ile Gly Gly Asn Leu Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Thr Ser Ser Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Tyr Ser Ser Ser Pro Trp Thr
1               5

<210> SEQ ID NO 7
<211> LENGTH: 461
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Asp Trp Thr Trp Arg Val Phe Cys Leu Leu Ala Val Ala Pro Gly
1               5                  10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65              70                  75                  80

Glu Lys Phe Lys Gly Lys Ala Thr Leu Thr Ala Asp Lys Ser Ser Ser
            85                  90                  95

Thr Ala Tyr Met His Leu Ser Ser Leu Thr Ser Glu Lys Ser Ala Val
        100                 105                 110

Tyr Phe Cys Ala Arg Glu Trp Ala Tyr Trp Gly Gln Gly Thr Leu Val
    115                 120                 125

Thr Val Ser Ala Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Ser Leu
    195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Asp Glu Leu Thr Lys Asn Gln Val Ser Leu Thr Cys Leu Val
370                 375                 380
```

```
Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Val Leu Asp Ser Asp
            405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly
450                 455                 460

<210> SEQ ID NO 8
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 9
<211> LENGTH: 720
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 9

```
Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Glu Arg Ala
                20                  25                  30

Leu Ala Ala Lys Pro Gly Leu Asp Thr Tyr Ser Leu Gly Gly Gly
            35                  40                  45

Ala Ala Arg Val Arg Val Arg Gly Ser Thr Gly Val Ala Ala Ala
        50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Tyr Gln Asn Val
                100                 105                 110

Cys Thr Gln Ser Tyr Ser Phe Val Trp Trp Asp Trp Ala Arg Trp Glu
                115                 120                 125

Arg Glu Ile Asp Trp Met Ala Leu Asn Gly Ile Asn Leu Ala Leu Ala
130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
                180                 185                 190

Pro Ser Trp His Ile Lys Gln Leu Tyr Leu Gln His Arg Val Leu Asp
                195                 200                 205

Gln Met Arg Ser Phe Gly Met Thr Pro Val Leu Pro Ala Phe Ala Gly
210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
                260                 265                 270

Leu Arg Glu Leu Ile Lys Glu Phe Gly Thr Asp His Ile Tyr Gly Ala
                275                 280                 285

Asp Thr Phe Asn Glu Met Gln Pro Pro Ser Ser Glu Pro Ser Tyr Leu
                290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
                340                 345                 350

Gly Arg Leu Leu Val Leu Asp Leu Phe Ala Glu Ser Gln Pro Val Tyr
                355                 360                 365

Thr Arg Thr Ala Ser Phe Gln Gly Gln Pro Phe Ile Trp Cys Met Leu
                370                 375                 380

His Asn Phe Gly Gly Asn His Gly Leu Phe Gly Ala Leu Glu Ala Val
385                 390                 395                 400
```

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
        435                 440                 445

Ala Ala Trp Val Thr Ser Phe Ala Ala Arg Arg Tyr Gly Val Ser His
450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Thr Ser Ala Pro Ser Leu Ala
        515                 520                 525

Thr Ser Pro Ala Phe Arg Tyr Asp Leu Leu Asp Leu Thr Arg Gln Ala
        530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
        595                 600                 605

Glu Ala Glu Ala Asp Phe Tyr Glu Gln Asn Ser Arg Tyr Gln Leu Thr
610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
        690                 695                 700

Lys Lys Ile Phe Leu Lys Tyr Tyr Pro Arg Trp Val Ala Gly Ser Trp
705                 710                 715                 720

<210> SEQ ID NO 10
<211> LENGTH: 1204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

```
Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Ser Leu
    195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Ser Ser Ser
450                 455                 460
```

```
Glu Leu Lys Thr Pro Leu Gly Asp Thr Thr His Ser Pro Arg Ser
465                 470                 475                 480

Pro Ser Ser Ser Asp Glu Ala Arg Glu Ala Ala Val Arg Ala Leu
            485                 490                 495

Val Ala Arg Leu Leu Gly Pro Gly Pro Ala Ala Asp Phe Ser Val Ser
                500                 505                 510

Val Glu Arg Ala Leu Ala Ala Lys Pro Gly Leu Asp Thr Tyr Ser Leu
            515                 520                 525

Gly Gly Gly Gly Ala Ala Arg Val Arg Val Arg Gly Ser Thr Gly Val
            530                 535                 540

Ala Ala Ala Ala Gly Leu His Arg Tyr Leu Arg Asp Phe Cys Gly Cys
545                 550                 555                 560

His Val Ala Trp Ser Gly Ser Gln Leu Arg Leu Pro Arg Pro Leu Pro
                565                 570                 575

Ala Val Pro Gly Glu Leu Thr Glu Ala Thr Pro Asn Arg Tyr Arg Tyr
                580                 585                 590

Tyr Gln Asn Val Cys Thr Gln Ser Tyr Ser Phe Val Trp Trp Asp Trp
            595                 600                 605

Ala Arg Trp Glu Arg Glu Ile Asp Trp Met Ala Leu Asn Gly Ile Asn
610                 615                 620

Leu Ala Leu Ala Trp Ser Gly Gln Glu Ala Ile Trp Gln Arg Val Tyr
625                 630                 635                 640

Leu Ala Leu Gly Leu Thr Gln Ala Glu Ile Asn Glu Phe Phe Thr Gly
                645                 650                 655

Pro Ala Phe Leu Ala Trp Gly Arg Met Gly Asn Leu His Thr Trp Asp
            660                 665                 670

Gly Pro Leu Pro Pro Ser Trp His Ile Lys Gln Leu Tyr Leu Gln His
            675                 680                 685

Arg Val Leu Asp Gln Met Arg Ser Phe Gly Met Thr Pro Val Leu Pro
            690                 695                 700

Ala Phe Ala Gly His Val Pro Glu Ala Val Thr Arg Val Phe Pro Gln
705                 710                 715                 720

Val Asn Val Thr Lys Met Gly Ser Trp Gly His Phe Asn Cys Ser Tyr
                725                 730                 735

Ser Cys Ser Phe Leu Leu Ala Pro Glu Asp Pro Ile Phe Pro Ile Ile
            740                 745                 750

Gly Ser Leu Phe Leu Arg Glu Leu Ile Lys Glu Phe Gly Thr Asp His
            755                 760                 765

Ile Tyr Gly Ala Asp Thr Phe Asn Glu Met Gln Pro Pro Ser Ser Glu
770                 775                 780

Pro Ser Tyr Leu Ala Ala Ala Thr Thr Ala Val Tyr Glu Ala Met Thr
785                 790                 795                 800

Ala Val Asp Thr Glu Ala Val Trp Leu Leu Gln Gly Trp Leu Phe Gln
            805                 810                 815

His Gln Pro Gln Phe Trp Gly Pro Ala Gln Ile Arg Ala Val Leu Gly
            820                 825                 830

Ala Val Pro Arg Gly Arg Leu Leu Val Leu Asp Leu Phe Ala Glu Ser
            835                 840                 845

Gln Pro Val Tyr Thr Arg Thr Ala Ser Phe Gln Gly Gln Pro Phe Ile
            850                 855                 860

Trp Cys Met Leu His Asn Phe Gly Gly Asn His Gly Leu Phe Gly Ala
865                 870                 875                 880

Leu Glu Ala Val Asn Gly Gly Pro Glu Ala Ala Arg Leu Phe Pro Asn
```

|   |   |   |   |   |   | 885 |   |   |   | 890 |   |   |   | 895 |   |
|---|---|---|---|---|---|---|---|---|---|---|---|---|---|---|---|

Ser Thr Met Val Gly Thr Gly Met Ala Pro Glu Gly Ile Ser Gln Asn
              900              905             910

Glu Val Val Tyr Ser Leu Met Ala Glu Leu Gly Trp Arg Lys Asp Pro
    915             920            925

Val Pro Asp Leu Ala Ala Trp Val Thr Ser Phe Ala Ala Arg Arg Tyr
930             935            940

Gly Val Ser His Pro Asp Ala Gly Ala Ala Trp Arg Leu Leu Leu Arg
945           950            955           960

Ser Val Tyr Asn Cys Ser Gly Glu Ala Cys Arg Gly His Asn Arg Ser
    965             970            975

Pro Leu Val Arg Arg Pro Ser Leu Gln Met Asn Thr Ser Ile Trp Tyr
              980             985           990

Asn Arg Ser Asp Val Phe Glu Ala Trp Arg Leu Leu Leu Thr Ser Ala
    995            1000          1005

Pro Ser Leu Ala Thr Ser Pro Ala Phe Arg Tyr Asp Leu Leu Asp
    1010             1015          1020

Leu Thr Arg Gln Ala Val Gln Glu Leu Val Ser Leu Tyr Tyr Glu
    1025             1030          1035

Glu Ala Arg Ser Ala Tyr Leu Ser Lys Glu Leu Ala Ser Leu Leu
    1040             1045          1050

Arg Ala Gly Gly Val Leu Ala Tyr Glu Leu Leu Pro Ala Leu Asp
    1055             1060          1065

Glu Val Leu Ala Ser Asp Ser Arg Phe Leu Leu Gly Ser Trp Leu
    1070             1075          1080

Glu Gln Ala Arg Ala Ala Ala Val Ser Glu Ala Glu Ala Asp Phe
    1085             1090          1095

Tyr Glu Gln Asn Ser Arg Tyr Gln Leu Thr Leu Trp Gly Pro Glu
    1100             1105          1110

Gly Asn Ile Leu Asp Tyr Ala Asn Lys Gln Leu Ala Gly Leu Val
    1115             1120          1125

Ala Asn Tyr Tyr Thr Pro Arg Trp Arg Leu Phe Leu Glu Ala Leu
    1130             1135          1140

Val Asp Ser Val Ala Gln Gly Ile Pro Phe Gln Gln His Gln Phe
    1145             1150          1155

Asp Lys Asn Val Phe Gln Leu Glu Gln Ala Phe Val Leu Ser Lys
    1160             1165          1170

Gln Arg Tyr Pro Ser Gln Pro Arg Gly Asp Thr Val Asp Leu Ala
    1175             1180          1185

Lys Lys Ile Phe Leu Lys Tyr Tyr Pro Arg Trp Val Ala Gly Ser
    1190             1195          1200

Trp

<210> SEQ ID NO 11
<211> LENGTH: 2191
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 11
aggcctcaga tgaagcccgt gaagctgctg ccgtccgtgc tctggtcgcc cgactgctgg    60
gtcctggtcc tgccgctgat ttttccgtga gtgtggagcg cgctctggca gctaagcccg   120

```
ggctggacac ctacagcctg gaggaggag gtgcagcacg agtgcgtgtc agggctcta      180 caggagtggc tgcagccgct ggactgcacc gatatctgag agattttgc ggctgtcatg      240 tggcctggtc tggaagtcag ctgcgactgc ctcgaccact gccagcagtc ccaggagagc      300
tgacagaagc cactcctaac cggtacagat actatcagaa cgtgtgcacc cagtcatatt      360
ccttcgtctg gtgggactgg gctcgttggg agagggaaat cgattggatg cactgaacg       420 gcattaatct ggctctggca tggagcggac aggaggctat ctggcagagg gtgtacctgg      480
cactggggct gactcaggcc gagattaacg aattctttac cggtcccgct tttctggcat      540
gggggcggat gggtaatctg cacacatggg acggccctct gccccctagt ggcacatca       600 aacagctgta tctgcagcat cgtgtgctgg atcagatgag gtcctttggg atgactcccg      660
tgctgcctgc cttcgctggt cacgtcccag aggccgtgac acgggtcttc ccccaggtga      720
acgtcactaa gatgggcagc tggggacatt ttaattgcag ctactcttgt agtttcctgc      780
tggctccaga agaccccatt tttcctatca ttggatctct gttcctgaga gagctgatca      840
aagaatttgg gaccgaccac atctacggtg ccgatacatt caacgagatg cagccaccct      900
ccagcgaacc atcttacctg gcagccgcta ccacagcagt gtatgaggcc atgaccgctg      960
tggacacaga agccgtctgg ctgctgcagg gctggctgtt tcagcatcag cctcagttct     1020
ggggaccagc ccagatcaga gctgtgctgg gagcagtccc tcgcggtcga ctgctggtgc     1080
tggatctgtt tgccgagtca cagcctgtct acactcgcac cgcttccttc agggccagc      1140 ccttcatctg gtgtatgctg cacaactttg gcggaaatca tgggctgttc ggtgcactgg     1200
aggcagtgaa cggaggtcct gaagcagcac gactgttttcc aaattccact atggtgggga   1260
ccggtatggc tcctgagggc atctctcaga tgaagtggt ctacagtctg atggccgagc      1320
tgggatggag gaaggaccct gtgccagatc tggctgcatg ggtcactagc ttcgccgcta     1380
ggcggtacgg ggtgtctcat ccagacgctg gtgcagcatg gcgactgctg ctgagatccg     1440
tgtataactg cagcggcgag gcttgccgcg gacataatcg atccccctg gtgagacgcc      1500 cttctctgca gatgaacacc agtatctggt acaatcgctc agacgtgttc gaggcttggc     1560
gactgctgct gacaagcgcc ccatctctgg ctactagccc cgcattccgt tatgacctgc     1620
tggatctgac aaggcaggcc gtgcaggagc tggtcagtct gtactatgag gaagctcgca     1680
gtgcatacct gtcaaaggaa ctggcatcac tgctgcgagc cggcggagtg ctggcttatg     1740
agctgctgcc cgctctggat gaagtcctgg catcagattc ccggtttctg ctgggcagtt     1800
ggctggagca ggctagagct gcagccgtgt cagaggcaga agccgacttc tacgagcaga     1860
actccagata tcagctgact ctgtggggcc ctgaaggaaa catcctggat tacgcaaaca     1920
agcagctggc cgggctggtg gctaattact ataccccacg ttggaggctg tttctggagg     1980
ccctggtgga ctctgtcgct cagggtattc ccttccagca gcatcagttt gataagaacg     2040
tgttccagct ggaacaggct ttcgtgctgt ccaaacagcg gtatccaagc cagcccagag     2100
gcgatacagt ggacctggca aagaagattt tcctgaagta ttatccaaga tgggtggctg     2160
gctcctggtg accgagctcg gtaccaagct t                                    2191
```

<210> SEQ ID NO 12
<211> LENGTH: 1185
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Asp Trp Thr Trp Arg Val Phe Cys Leu Leu Ala Val Ala Pro Gly
1               5                   10                  15
Ala His Ser Gln Val Gln Leu Gln Gln Ser Gly Pro Glu Leu Val Lys
            20                  25                  30
Pro Gly Ala Leu Val Lys Ile Ser Cys Lys Ala Ser Gly Tyr Thr Phe
        35                  40                  45
Thr Asn Tyr Asp Ile His Trp Val Lys Gln Arg Pro Gly Gln Gly Leu
    50                  55                  60
Glu Trp Ile Gly Trp Ile Tyr Pro Gly Asp Gly Ser Thr Lys Tyr Asn
65                  70                  75                  80
Glu Lys Phe Lys Gly Lys Ala Thr Leu Thr Ala Asp Lys Ser Ser Ser
                85                  90                  95
Thr Ala Tyr Met His Leu Ser Ser Leu Thr Ser Glu Lys Ser Ala Val
            100                 105                 110
Tyr Phe Cys Ala Arg Glu Trp Ala Tyr Trp Gly Gln Gly Thr Leu Val
        115                 120                 125
Thr Val Ser Ala Ala Ser Thr Lys Gly Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Ser Ser Ser
        450                 455                 460

Ser Asp Glu Ala Arg Glu Ala Ala Val Arg Ala Leu Val Ala Arg
465             470                 475                 480

Leu Leu Gly Pro Gly Pro Ala Ala Asp Phe Ser Val Ser Val Glu Arg
                485                 490                 495

Ala Leu Ala Ala Lys Pro Gly Leu Asp Thr Tyr Ser Leu Gly Gly Gly
                500                 505                 510

Gly Ala Ala Arg Val Arg Val Arg Gly Ser Thr Gly Val Ala Ala Ala
                515                 520                 525

Ala Gly Leu His Arg Tyr Leu Arg Asp Phe Cys Gly Cys His Val Ala
            530                 535                 540

Trp Ser Gly Ser Gln Leu Arg Leu Pro Arg Pro Leu Pro Ala Val Pro
545                 550                 555                 560

Gly Glu Leu Thr Glu Ala Thr Pro Asn Arg Tyr Arg Tyr Tyr Gln Asn
                565                 570                 575

Val Cys Thr Gln Ser Tyr Ser Phe Val Trp Asp Trp Ala Arg Trp
                580                 585                 590

Glu Arg Glu Ile Asp Trp Met Ala Leu Asn Gly Ile Asn Leu Ala Leu
            595                 600                 605

Ala Trp Ser Gly Gln Glu Ala Ile Trp Gln Arg Val Tyr Leu Ala Leu
            610                 615                 620

Gly Leu Thr Gln Ala Glu Ile Asn Glu Phe Phe Thr Gly Pro Ala Phe
625                 630                 635                 640

Leu Ala Trp Gly Arg Met Gly Asn Leu His Thr Trp Asp Gly Pro Leu
                645                 650                 655

Pro Pro Ser Trp His Ile Lys Gln Leu Tyr Leu Gln His Arg Val Leu
                660                 665                 670

Asp Gln Met Arg Ser Phe Gly Met Thr Pro Val Leu Pro Ala Phe Ala
            675                 680                 685

Gly His Val Pro Glu Ala Val Thr Arg Val Phe Pro Gln Val Asn Val
        690                 695                 700

Thr Lys Met Gly Ser Trp Gly His Phe Asn Cys Ser Tyr Ser Cys Ser
705                 710                 715                 720

Phe Leu Leu Ala Pro Glu Asp Pro Ile Phe Pro Ile Ile Gly Ser Leu
                725                 730                 735

Phe Leu Arg Glu Leu Ile Lys Glu Phe Gly Thr Asp His Ile Tyr Gly
            740                 745                 750

Ala Asp Thr Phe Asn Glu Met Gln Pro Pro Ser Ser Glu Pro Ser Tyr
            755                 760                 765

Leu Ala Ala Ala Thr Thr Ala Val Tyr Glu Ala Met Thr Ala Val Asp
            770                 775                 780

Thr Glu Ala Val Trp Leu Leu Gln Gly Trp Leu Phe Gln His Gln Pro
785                 790                 795                 800

Gln Phe Trp Gly Pro Ala Gln Ile Arg Ala Val Leu Gly Ala Val Pro
                805                 810                 815

Arg Gly Arg Leu Leu Val Leu Asp Leu Phe Ala Glu Ser Gln Pro Val
                820                 825                 830
```

```
Tyr Thr Arg Thr Ala Ser Phe Gln Gly Gln Pro Phe Ile Trp Cys Met
            835                 840                 845

Leu His Asn Phe Gly Gly Asn His Gly Leu Phe Gly Ala Leu Glu Ala
850                 855                 860

Val Asn Gly Gly Pro Glu Ala Ala Arg Leu Phe Pro Asn Ser Thr Met
865                 870                 875                 880

Val Gly Thr Gly Met Ala Pro Glu Gly Ile Ser Gln Asn Glu Val Val
                885                 890                 895

Tyr Ser Leu Met Ala Glu Leu Gly Trp Arg Lys Asp Pro Val Pro Asp
            900                 905                 910

Leu Ala Ala Trp Val Thr Ser Phe Ala Ala Arg Arg Tyr Gly Val Ser
        915                 920                 925

His Pro Asp Ala Gly Ala Ala Trp Arg Leu Leu Arg Ser Val Tyr
    930                 935                 940

Asn Cys Ser Gly Glu Ala Cys Arg Gly His Asn Arg Ser Pro Leu Val
945                 950                 955                 960

Arg Arg Pro Ser Leu Gln Met Asn Thr Ser Ile Trp Tyr Asn Arg Ser
                965                 970                 975

Asp Val Phe Glu Ala Trp Arg Leu Leu Leu Thr Ser Ala Pro Ser Leu
            980                 985                 990

Ala Thr Ser Pro Ala Phe Arg Tyr Asp Leu Leu Asp Leu Thr Arg Gln
        995                 1000                1005

Ala Val Gln Glu Leu Val Ser Leu Tyr Tyr Glu Glu Ala Arg Ser
    1010                1015                1020

Ala Tyr Leu Ser Lys Glu Leu Ala Ser Leu Leu Arg Ala Gly Gly
    1025                1030                1035

Val Leu Ala Tyr Glu Leu Leu Pro Ala Leu Asp Glu Val Leu Ala
    1040                1045                1050

Ser Asp Ser Arg Phe Leu Leu Gly Ser Trp Leu Glu Gln Ala Arg
    1055                1060                1065

Ala Ala Ala Val Ser Glu Ala Glu Ala Asp Phe Tyr Glu Gln Asn
    1070                1075                1080

Ser Arg Tyr Gln Leu Thr Leu Trp Gly Pro Glu Gly Asn Ile Leu
    1085                1090                1095

Asp Tyr Ala Asn Lys Gln Leu Ala Gly Leu Val Ala Asn Tyr Tyr
    1100                1105                1110

Thr Pro Arg Trp Arg Leu Phe Leu Glu Ala Leu Val Asp Ser Val
    1115                1120                1125

Ala Gln Gly Ile Pro Phe Gln Gln His Gln Phe Asp Lys Asn Val
    1130                1135                1140

Phe Gln Leu Glu Gln Ala Phe Val Leu Ser Lys Gln Arg Tyr Pro
    1145                1150                1155

Ser Gln Pro Arg Gly Asp Thr Val Asp Leu Ala Lys Lys Ile Phe
    1160                1165                1170

Leu Lys Tyr Tyr Pro Arg Trp Val Ala Gly Ser Trp
    1175                1180                1185

<210> SEQ ID NO 13
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
```

```
gccgccacca tggagacccc cgcccagctg ctgttcctgt tgctgctttg gcttccagat    60
actaccggcg acatccagat gacccagtct ccatcctcct tatctgcctc tctgggagaa   120
agagtcagtc tcacttgtcg ggcaagtcag gacattggtg gtaacttata ctggcttcag   180
cagggaccag atggaactat taaacgcctg atctacgcca catccagttt agattctggt   240
gtccccaaaa ggttcagtgg cagtaggtct gggtcagatt attctctcac catcagcagc   300
cttgagtctg aagattttgt agactattac tgtctacagt attctagttc ccgtggacg    360 ttcggtggag gcacaaagct ggaaataaaa cgaactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttag          714
```

<210> SEQ ID NO 14
<211> LENGTH: 3624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gccgccacca tggactggac ctggagggtg ttctgcctgc ttgcagtggc ccccggagcc    60
cacagccagg ttcagctgca gcagtctgga cctgagctgg tgaagcctgg ggctttagtg   120
aagatatcct gcaaggcttc tggttacacc ttcacaaact acgatataca ctgggtgaag   180
cagaggcctg acagggact tgagtggatt ggatggattt atcctggaga tggtagtact   240
aagtacaatg agaaattcaa gggcaaggcc acactgactg cagacaaatc ctccagcaca   300
gcctacatgc acctcagcag cctgacttct gagaaatctg cagtctattt ctgtgcaaga   360
gagtgggctt actggggcca aggactctg gtcactgtct ctgcagctag caccaagggc   420
ccatcggtct tccccctggc accctcctcc aagagcacct ctgggggcac agcggccctg   480
ggctgcctgg tcaaggacta cttccccgaa ccggtgacgg tgtcgtggaa ctcaggcgcc   540
ctgaccagcg gcgtgcacac cttcccggct gtcctacagt cctcaggact ctactccctc   600
agcagcgtgt gaccgtgcc ctccagcagc ttgggcaccc agacctacat ctgcaacgtg   660
aatcacaagc ccagcaacac caaggtggac aagaaagttg agcccaaatc ttgtgacaaa   720
actcacacat gcccaccgtg cccagcacct gaactcctgg ggggaccgtc agtcttcctc   780
ttccccccaa aacccaagga caccctcatg atctcccgga cccctgaggt cacatgcgtg   840
gtggtggacg tgagccacga agaccctgag gtcaagttca actggtacgt ggacggcgtg   900
gaggtgcata atgccaagac aaagccgcgg gaggagcagt acaacagcac gtaccgtgtg   960
gtcagcgtcc tcaccgtcct gcaccaggac tggctgaatg gcaaggagta caagtgcaag  1020
gtctccaaca aagccctccc agcccccatc gagaaaacca tctccaaagc caagggcag   1080 ccccgagaac cacaggtgta caccctgccc ccatcccggg atgagctgac caagaaccag  1140
gtcagcctga cctgcctggt caaaggcttc tatcccagcg acatcgccgt ggagtgggag  1200 agcaatggc agccggagaa caactacaag accacgcctc ccgtgctgga ctccgacggc  1260
tccttcttcc tctacagcaa gctcaccgtg gacaagagca ggtggcagca ggggaacgtc  1320
```

```
ttctcatgct ccgtgatgca tgaggctctg cacaaccact acacgcagaa gagcctctcc    1380
ctgtctcctg gtagtagttc agagctcaaa accccacttg gtgacacaac tcacacaagc    1440
ccacggagcc caagttcctc agatgaagcc cgtgaagctg ctgccgtccg tgctctggtc    1500
gcccgactgc tgggtcctgg tcctgccgct gattttccg tgagtgtgga gcgcgctctg     1560
gcagctaagc ccgggctgga cacctacagc ctgggaggag gaggtgcagc acgagtgcgt    1620 gtcagggct ctacaggagt ggctgcagcc gctggactgc accgatatct gagagatttt     1680
tgcggctgtc atgtggcctg gtctggaagt cagctgcgac tgcctcgacc actgccagca    1740
gtcccaggag agctgacaga agccactcct aaccggtaca gatactatca gaacgtgtgc    1800
acccagtcat attccttcgt ctggtgggac tgggctcgtt gggagaggga atcgattgg     1860 atggcactga acggcattaa tctggctctg gcatggagcg acaggaggc tatctggcag     1920 agggtgtacc tggcactggg gctgactcag gccgagatta acgaattctt taccggtccc    1980
gcttttctgg catgggggcg gatgggtaat ctgcacacat gggacggccc tctgcccct    2040 agttggcaca tcaaacagct gtatctgcag catcgtgtgc tggatcagat gaggtccttt    2100
gggatgactc ccgtgctgcc tgccttcgct ggtcacgtcc cagaggccgt gacacgggtc    2160
ttcccccagg tgaacgtcac taagatgggc agctgggac attttaattg cagctactct    2220
tgtagtttcc tgctggctcc agaagaccc attttcccta tcattggatc tctgttcctg    2280
agagagctga tcaaagaatt tgggaccgac cacatctacg gtgccgatac attcaacgag    2340
atgcagccac cctccagcga accatcttac ctggcagccg ctaccacagc agtgtatgag    2400
gccatgaccg ctgtggacac agaagccgtc tggctgctgc agggctggct gtttcagcat    2460
cagcctcagt tctggggacc agcccagatc agagctgtgc tgggagcagt ccctcgcggt    2520
cgactgctgg tgctggatct gtttgccgag tcacagcctg tctacactcg caccgcttcc    2580
ttccagggcc agcccttcat ctggtgtatg ctgcacaact ttggcggaaa tcatgggctg    2640
ttcggtgcac tggaggcagt gaacggaggt cctgaagcag cacgactgtt tccaaattcc    2700
actatggtgg ggaccggtat ggctcctgag ggcatctctc agaatgaagt ggtctacagt    2760
ctgatggccg agctgggatg gaggaaggac cctgtgccag atctggctgc atgggtcact    2820
agcttcgccg ctaggcggta cggggtgtct catccagacg ctggtgcagc atggcgactg    2880
ctgctgagat ccgtgtataa ctgcagcggc gaggcttgcc gcggacataa tcgatccccc    2940
ctggtgagac gcccttctct gcagatgaac accagtatct ggtacaatcg ctcagacgtg    3000
ttcgaggctt ggcgactgct gctgacaagc gccccatctc tggctactag ccccgcattc    3060
cgttatgacc tgctggatct gacaaggcag gccgtgcagg agctggtcag tctgtactat    3120
gaggaagctc gcagtgcata cctgtcaaag gaactggcat cactgctgcg agccggcgga    3180
gtgctggctt atgagctgct gcccgctctg gatgaagtcc tggcatcaga ttcccggttt    3240
ctgctgggca gttggctgga gcaggctaga gctgcagccg tgtcagaggc agaagccgac    3300
ttctacgagc agaactccag atatcagctg actctgtggg gccctgaagg aaacatcctg    3360
gattacgcaa acaagcagct ggccgggctg gtggctaatt actataccc acgttggagg     3420 ctgtttctgg aggccctggt ggactctgtc gctcagggta ttcccttcca gcagcatcag    3480
tttgataaga acgtgttcca gctggaacag ctttcgtgc tgtccaaaca gcggtatcca      3540
agccagccca gaggcgatac agtggacctg gcaaagaaga ttttcctgaa gtattatcca    3600
agatgggtgg ctggctcctg gtga                                          3624
```

<210> SEQ ID NO 15
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gccgccacca tggttcgacc attgaactgc atcgtcgccg tgtcccaaaa tatggggatt      60
ggcaagaacg gagacctacc ctggcctccg ctcaggaacg agttcaagta cttccaaaga     120
atgaccacaa cctcttcagt ggaaggtaaa cagaatctgg tgattatggg taggaaaacc     180
tggttctcca ttcctgagaa gatcgacctt taaaggaca gaattaatat agttctcagt      240
agagaactca agaaccacc acgaggagct cattttcttg ccaaaagttt ggatgatgcc      300
ttaagactta ttgaacaacc ggaattggca agtaaagtag acatggtttg atagtcgga      360 ggcagttctg tttaccagga agccatgaat caaccaggcc acctcagact ctttgtgaca     420
aggatcatgc aggaatttga agtgacacg ttttttcccag aaattgattt ggggaaatat     480
aaacttctcc cagaataccc aggcgtcctc tctgaggtcc aggaggaaaa aggcatcaag     540
tataagtttg aagtctacga gaagaaagac taa                                  573

<210> SEQ ID NO 16
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 17
<211> LENGTH: 3648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gccgccacca tggactggac ctggagggtg ttctgcctgc ttgcagtggc ccccggagcc    60
cacagccagg ttcagctgca gcagtctgga cctgagctgg tgaagcctgg gctttagtg   120
aagatatcct gcaaggcttc tggttacacc ttcacaaact acgatataca ctgggtgaag   180
cagaggcctg acagggact tgagtggatt ggatggattt atcctggaga tggtagtact   240
aagtacaatg agaaattcaa gggcaaggcc acactgactg cagacaaatc ctccagcaca   300
gcctacatgc acctcagcag cctgacttct gagaaatctg cagtctattt ctgtgcaaga   360
gagtgggctt actggggcca agggactctg gtcactgtct ctgcagctag caccaagggc   420
ccatcggtct tcccctggc accctcctcc aagagcacct ctgggggcac agcggccctg   480
ggctgcctgg tcaaggacta cttccccgaa ccggtgacgg tgtcgtggaa ctcaggcgcc   540
ctgaccagcg gcgtgcacac cttccgggct gtcctacagt cctcaggact ctactccctc   600
agcagcgtgg tgaccgtgcc ctccagcagc ttgggcaccc agacctacat ctgcaacgtg   660
aatcacaagc ccagcaacac caaggtggac aagaaagttg agcccaaatc ttgtgacaaa   720
actcacacat gcccaccgtg cccagcacct gaactcctgg ggggaccgtc agtcttcctc   780
ttccccccaa aacccaagga caccctcatg atctcccgga cccctgaggt cacatgcgtg   840
gtggtggacg tgagccacga agaccctgag gtcaagttca actggtacgt ggacggcgtg   900
gaggtgcata atgccaagac aaagccgcgg gaggagcagt acaacagcac gtaccgtgtg   960
gtcagcgtcc tcaccgtcct gcaccaggac tggctgaatg gcaaggagta caagtgcaag  1020
gtctccaaca agccctccc agcccccatc gagaaaacca tctccaaagc caaagggcag  1080
ccccgagaac acaggtgta caccctgccc ccatcccggg atgagctgac caagaaccag  1140
gtcagcctga cctgcctggt caaaggcttc tatcccagcg acatcgccgt ggagtgggag  1200
agcaatgggc agccggagaa caactacaag accacgcctc ccgtgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctcctg gtagtagttc agagctcaaa acccccacttg gtgacacaac tcacacaagc  1440
ccacggagcc cagcacctga attcctgggg ggaccgagtt cctcagatga agcccgtgaa  1500
gctgctgccg tccgtgctct ggtcgcccga ctgctgggtc ctggtcctgc cgctgatttt  1560
tccgtgagtg tggagcgcgc tctggcagct aagcccgggc tggacaccta cagcctggga  1620
ggaggaggtg cagcacgagt gcgtgtcagg ggctctacag gagtggctgc agccgctgga  1680
ctgcaccgat atctgagaga ttttgcggc tgtcatgtgg cctggtctgg aagtcagctg  1740
cgactgcctc gaccactgcc agcagtccca ggagagctga cagaagccac tcctaaccgg  1800
tacagatact atcagaacgt gtgcacccag tcatattcct tcgtctggtg ggactgggct  1860
cgttgggaga gggaaatcga ttggatggca ctgaacggca ttaatctggc tctggcatgg  1920
agcggacagg aggctatctg gcagagggtg tacctggcac tggggctgac tcaggccgag  1980
attaacgaat tctttaccgg tcccgctttt ctggcatggg ggcggatggg taatctgcac  2040
acatgggacg gccctctgcc ccctagttgg cacatcaaac agctgtatct gcagcatcgt  2100
```

```
gtgctggatc agatgaggtc ctttgggatg actcccgtgc tgcctgcctt cgctggtcac    2160
gtcccagagg ccgtgacacg ggtcttcccc caggtgaacg tcactaagat gggcagctgg    2220 ggacattta attgcagcta ctcttgtagt ttcctgctgg ctccagaaga ccccattttt    2280
cctatcattg gatctctgtt cctgagagag ctgatcaaag aatttgggac cgaccacatc    2340
tacggtgccg atacattcaa cgagatgcag ccaccctcca gcgaaccatc ttacctggca    2400
gccgctacca cagcagtgta tgaggccatg accgctgtgg acacagaagc cgtctggctg    2460
ctgcagggct ggctgtttca gcatcagcct cagttctggg accagcccca gatcagagct    2520
gtgctgggag cagtccctcg cggtcgactg ctggtgctgg atctgtttgc cgagtcacag    2580
cctgtctaca ctcgcaccgc ttccttccag ggccagccct catctggtg tatgctgcac    2640 aactttggcg aaaatcatgg gctgttcggt gcactggagg cagtgaacgg aggtcctgaa    2700
gcagcacgac tgtttccaaa ttccactatg gtggggaccg gtatggctcc tgagggcatc    2760
tctcagaatg aagtggtcta cagtctgatg gccgagctgg gatggaggaa ggaccctgtg    2820
ccagatctgg ctgcatgggt cactagcttc gccgctaggc ggtacggggt gtctcatcca    2880
gacgctggtg cagcatggcg actgctgctg agatccgtgt ataactgcag cggcgaggct    2940
tgccgcggac ataatcgatc ccccctggtg agacgcccctt ctctgcagat gaacaccagt    3000
atctggtaca atcgctcaga cgtgttcgag cttggcgac tgctgctgac aagcgcccca    3060
tctctggcta ctagccccgc attccgttat gacctgctgg atctgacaag gcaggccgtg    3120
caggagctgg tcagtctgta ctatgaggaa gctcgcagtg cataccctgc aaaggaactg    3180
gcatcactgc tgcgagccgg cggagtgctg gcttatgagc tgctgcccgc tctggatgaa    3240
gtcctggcat cagattcccg gtttctgctg ggcagttggc tggagcaggc tagagctgca    3300
gccgtgtcag aggcagaagc cgacttctac gagcagaact ccagatatca gctgactctg    3360
tggggccctg aaggaaacat cctggattac gcaaacaagc agctggccgg gctggtggct    3420
aattactata ccccacgttg gaggctgttt ctggaggccc tggtggactc tgtcgctcag    3480
ggtattccct ccagcagca tcagtttgat aagaacgtgt tccagctgga acaggctttc    3540
gtgctgtcca acagcggta tccaagccag cccagaggcg atacagtgga cctggcaaag    3600
aagattttcc tgaagtatta tccaagatgg gtggctggct cctggtga              3648
```

<210> SEQ ID NO 18
<211> LENGTH: 1212
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

```
Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80
```

-continued

```
Glu Lys Phe Lys Gly Lys Ala Thr Leu Thr Ala Asp Lys Ser Ser Ser
                 85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Ser Ser Ser
    450                 455                 460

Glu Leu Lys Thr Pro Leu Gly Asp Thr Thr His Thr Ser Pro Arg Ser
465                 470                 475                 480

Pro Ala Pro Glu Phe Leu Gly Gly Pro Ser Ser Asp Glu Ala Arg
                485                 490                 495

Glu Ala Ala Ala Val Arg Ala Leu Val Ala Arg Leu Leu Gly Pro Gly
```

-continued

```
                500             505             510
Pro Ala Ala Asp Phe Ser Val Ser Val Glu Arg Ala Leu Ala Ala Lys
            515             520             525

Pro Gly Leu Asp Thr Tyr Ser Leu Gly Gly Gly Ala Ala Arg Val
            530             535             540

Arg Val Arg Gly Ser Thr Gly Val Ala Ala Ala Gly Leu His Arg
545             550             555             560

Tyr Leu Arg Asp Phe Cys Gly Cys His Val Ala Trp Ser Gly Ser Gln
                565             570             575

Leu Arg Leu Pro Arg Pro Leu Pro Ala Val Pro Gly Glu Leu Thr Glu
            580             585             590

Ala Thr Pro Asn Arg Tyr Arg Tyr Tyr Gln Asn Val Cys Thr Gln Ser
            595             600             605

Tyr Ser Phe Val Trp Trp Asp Trp Ala Arg Trp Glu Arg Glu Ile Asp
            610             615             620

Trp Met Ala Leu Asn Gly Ile Asn Leu Ala Leu Ala Trp Ser Gly Gln
625             630             635             640

Glu Ala Ile Trp Gln Arg Val Tyr Leu Ala Leu Gly Leu Thr Gln Ala
                645             650             655

Glu Ile Asn Glu Phe Phe Thr Gly Pro Ala Phe Leu Ala Trp Gly Arg
            660             665             670

Met Gly Asn Leu His Thr Trp Asp Gly Pro Leu Pro Ser Trp His
            675             680             685

Ile Lys Gln Leu Tyr Leu Gln His Arg Val Leu Asp Gln Met Arg Ser
            690             695             700

Phe Gly Met Thr Pro Val Leu Pro Ala Phe Ala Gly His Val Pro Glu
705             710             715             720

Ala Val Thr Arg Val Phe Pro Gln Val Asn Val Thr Lys Met Gly Ser
                725             730             735

Trp Gly His Phe Asn Cys Ser Tyr Ser Cys Ser Phe Leu Leu Ala Pro
            740             745             750

Glu Asp Pro Ile Phe Pro Ile Ile Gly Ser Leu Phe Leu Arg Glu Leu
            755             760             765

Ile Lys Glu Phe Gly Thr Asp His Ile Tyr Gly Ala Asp Thr Phe Asn
770             775             780

Glu Met Gln Pro Pro Ser Ser Glu Pro Ser Tyr Leu Ala Ala Thr
785             790             795             800

Thr Ala Val Tyr Glu Ala Met Thr Ala Val Asp Thr Glu Ala Val Trp
                805             810             815

Leu Leu Gln Gly Trp Leu Phe Gln His Gln Pro Gln Phe Trp Gly Pro
            820             825             830

Ala Gln Ile Arg Ala Val Leu Gly Ala Val Pro Arg Gly Arg Leu Leu
            835             840             845

Val Leu Asp Leu Phe Ala Glu Ser Gln Pro Val Tyr Thr Arg Thr Ala
850             855             860

Ser Phe Gln Gly Gln Pro Phe Ile Trp Cys Met Leu His Asn Phe Gly
865             870             875             880

Gly Asn His Gly Leu Phe Gly Ala Leu Glu Ala Val Asn Gly Gly Pro
                885             890             895

Glu Ala Ala Arg Leu Phe Pro Asn Ser Thr Met Val Gly Thr Gly Met
            900             905             910

Ala Pro Glu Gly Ile Ser Gln Asn Glu Val Val Tyr Ser Leu Met Ala
            915             920             925
```

Glu Leu Gly Trp Arg Lys Asp Pro Val Pro Asp Leu Ala Ala Trp Val
    930                 935                 940

Thr Ser Phe Ala Ala Arg Arg Tyr Gly Val Ser His Pro Asp Ala Gly
945                 950                 955                 960

Ala Ala Trp Arg Leu Leu Leu Arg Ser Val Tyr Asn Cys Ser Gly Glu
            965                 970                 975

Ala Cys Arg Gly His Asn Arg Ser Pro Leu Val Arg Arg Pro Ser Leu
            980                 985                 990

Gln Met Asn Thr Ser Ile Trp Tyr Asn Arg Ser Asp Val Phe Glu Ala
        995                 1000                1005

Trp Arg Leu Leu Leu Thr Ser Ala Pro Ser Leu Ala Thr Ser Pro
    1010                1015                1020

Ala Phe Arg Tyr Asp Leu Leu Asp Leu Thr Arg Gln Ala Val Gln
    1025                1030                1035

Glu Leu Val Ser Leu Tyr Tyr Glu Glu Ala Arg Ser Ala Tyr Leu
    1040                1045                1050

Ser Lys Glu Leu Ala Ser Leu Leu Arg Ala Gly Gly Val Leu Ala
    1055                1060                1065

Tyr Glu Leu Leu Pro Ala Leu Asp Glu Val Leu Ala Ser Asp Ser
    1070                1075                1080

Arg Phe Leu Leu Gly Ser Trp Leu Glu Gln Ala Arg Ala Ala Ala
    1085                1090                1095

Val Ser Glu Ala Glu Ala Asp Phe Tyr Glu Gln Asn Ser Arg Tyr
    1100                1105                1110

Gln Leu Thr Leu Trp Gly Pro Glu Gly Asn Ile Leu Asp Tyr Ala
    1115                1120                1125

Asn Lys Gln Leu Ala Gly Leu Val Ala Asn Tyr Tyr Thr Pro Arg
    1130                1135                1140

Trp Arg Leu Phe Leu Glu Ala Leu Val Asp Ser Val Ala Gln Gly
    1145                1150                1155

Ile Pro Phe Gln Gln His Gln Phe Asp Lys Asn Val Phe Gln Leu
    1160                1165                1170

Glu Gln Ala Phe Val Leu Ser Lys Gln Arg Tyr Pro Ser Gln Pro
    1175                1180                1185

Arg Gly Asp Thr Val Asp Leu Ala Lys Lys Ile Phe Leu Lys Tyr
    1190                1195                1200

Tyr Pro Arg Trp Val Ala Gly Ser Trp
    1205                1210

<210> SEQ ID NO 19
<211> LENGTH: 3540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gccgccacca tggactggac ctggagggtg ttctgcctgc ttgcagtggc cccggagcc      60 cacagccagg ttcagctgca gcagtctgga cctgagctgg tgaagcctgg ggctttagtg    120
aagatatcct gcaaggcttc tggttacacc ttcacaaact acgatataca ctgggtgaag    180
cagaggcctg acagggact tgagtggatt ggatggattt atcctggaga tggtagtact    240
aagtacaatg agaaattcaa gggcaaggcc acactgactg cagacaaatc ctccagcaca    300

-continued

```
gcctacatgc acctcagcag cctgacttct gagaaatctg cagtctattt ctgtgcaaga    360
gagtgggctt actggggcca agggactctg gtcactgtct ctgcagctag caccaagggc    420
ccatcggtct tcccctggc acctcctcc aagagcacct ctgggggcac agcggccctg     480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgt gaccgtgcc ctccagcagc ttgggcaccc agacctacat ctgcaacgtg     660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caagggcag   1080 ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctcctg gtagtagttc agagctcaaa accccacttg gtgacacaac tcacacaagc   1440
ccacggagcc cagcacctga attcctgggg ggaccgagtt ccaagcccgg gctggacacc   1500
tacagcctgg gaggagagg tgcagcacga gtgcgtgtca gggctctac aggagtggct    1560 gcagccgctg gactgcaccg atatctgaga gattttgcg gctgtcatgt ggcctggtct   1620
ggaagtcagc tgcgactgcc tcgaccactg ccagcagtcc caggagagct gacagaagcc   1680
actcctaacc ggtacagata ctatcagaac gtgtgcaccc agtcatattc cttcgtctgg   1740
tgggactggg ctcgttggga gagggaaatc gattggatgg cactgaacgg cattaatctg   1800
gctctggcat ggagcggaca ggaggctatc tggcagaggg tgtacctggc actggggctg   1860
actcaggccg agattaacga attctttacc ggtcccgctt ttctggcatg ggggcggatg   1920
ggtaatctgc acacatggga cggccctctg cccctagtt ggcacatcaa acagctgtat    1980
ctgcagcatc gtgtgctgga tcagatgagg tccttggga tgactcccgt gctgcctgcc    2040
ttcgctggtc acgtcccaga ggccgtgaca cgggtcttcc cccaggtgaa cgtcactaag    2100
atgggcagct ggggacattt taattgcagc tactcttgta gtttcctgct ggctccagaa    2160
gaccccattt ttcctatcat tggatctctg ttcctgagag agctgatcaa agaatttggg    2220
accgaccaca tctacggtgc cgatacattc aacgagatgc agccaccctc cagcgaacca    2280
tcttacctgg cagccgctac cacagcagtg tatgaggcca tgaccgctgt ggacacagaa    2340
gccgtctggc tgctgcaggg ctggctgttt cagcatcagc ctcagttctg ggaccagcc    2400 cagatcagag ctgtgctggg agcagtccct cgcggtcgac tgctggtgct ggatctgttt    2460
gccgagtcac agcctgtcta cactcgcacc gcttccttcc agggccagcc cttcatctgg    2520
tgtatgctgc acaactttgg cggaaatcat gggctgttcg gtgcactgga ggcagtgaac    2580
ggaggtcctg aagcagcacg actgtttcca aattccacta tggtggggac cggtatggct    2640
cctgagggca tctctcagaa tgaagtggtc tacagtctga tggccgagct gggatggagg    2700
```

```
aaggaccctg tgccagatct ggctgcatgg gtcactagct tcgccgctag gcggtacggg   2760
gtgtctcatc cagacgctgg tgcagcatgg cgactgctgc tgagatccgt gtataactgc   2820
agcggcgagg cttgccgcgg acataatcga tccccctgg tgagacgccc ttctctgcag    2880
atgaacacca gtatctggta caatcgctca gacgtgttcg aggcttggcg actgctgctg   2940
acaagcgccc catctctggc tactagcccc gcattccgtt atgacctgct ggatctgaca   3000
aggcaggccg tgcaggagct ggtcagtctg tactatgagg aagctcgcag tgcatacctg   3060
tcaaaggaac tggcatcact gctgcgagcc ggcggagtgc tggcttatga gctgctgccc   3120
gctctggatg aagtcctggc atcagattcc cggtttctgc tgggcagttg gctggagcag   3180
gctagagctg cagccgtgtc agaggcagaa gccgacttct acgagcagaa ctccagatat   3240
cagctgactc tgtggggccc tgaaggaaac atcctggatt acgcaaacaa gcagctggcc   3300
gggctggtgg ctaattacta taccccacgt tggaggctgt ttctggaggc cctggtggac   3360
tctgtcgctc agggtattcc cttccagcag catcagtttg ataagaacgt gttccagctg   3420
gaacaggctt tcgtgctgtc caaacagcgg tatccaagcc agcccagagg cgatacagtg   3480
gacctggcaa agaagatttt cctgaagtat tatccaagat gggtggctgg ctcctggtga   3540
```

<210> SEQ ID NO 20
<211> LENGTH: 1176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205
```

```
Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Ser Ser Ser
        450                 455                 460

Glu Leu Lys Thr Pro Leu Gly Asp Thr His Thr Ser Pro Arg Ser
465                 470                 475                 480

Pro Ala Pro Glu Phe Leu Gly Gly Pro Ser Ser Lys Pro Gly Leu Asp
                485                 490                 495

Thr Tyr Ser Leu Gly Gly Gly Ala Ala Arg Val Arg Val Arg Gly
                500                 505                 510

Ser Thr Gly Val Ala Ala Ala Gly Leu His Arg Tyr Leu Arg Asp
            515                 520                 525

Phe Cys Gly Cys His Val Ala Trp Ser Gly Ser Gln Leu Arg Leu Pro
            530                 535                 540

Arg Pro Leu Pro Ala Val Pro Gly Glu Leu Thr Glu Ala Thr Pro Asn
545                 550                 555                 560

Arg Tyr Arg Tyr Tyr Gln Asn Val Cys Thr Gln Ser Tyr Ser Phe Val
                565                 570                 575

Trp Trp Asp Trp Ala Arg Trp Glu Arg Glu Ile Asp Trp Met Ala Leu
                580                 585                 590

Asn Gly Ile Asn Leu Ala Leu Ala Trp Ser Gly Gln Glu Ala Ile Trp
                595                 600                 605

Gln Arg Val Tyr Leu Ala Leu Gly Leu Thr Gln Ala Glu Ile Asn Glu
610                 615                 620

Phe Phe Thr Gly Pro Ala Phe Leu Ala Trp Gly Arg Met Gly Asn Leu
```

-continued

```
            625                 630                 635                 640
        His Thr Trp Asp Gly Pro Leu Pro Pro Ser Trp His Ile Lys Gln Leu
                        645                 650                 655

Tyr Leu Gln His Arg Val Leu Asp Gln Met Arg Ser Phe Gly Met Thr
                        660                 665                 670

Pro Val Leu Pro Ala Phe Ala Gly His Val Pro Glu Ala Val Thr Arg
                        675                 680                 685

Val Phe Pro Gln Val Asn Val Thr Lys Met Gly Ser Trp Gly His Phe
                        690                 695                 700

Asn Cys Ser Tyr Ser Cys Ser Phe Leu Leu Ala Pro Glu Asp Pro Ile
        705                 710                 715                 720

Phe Pro Ile Ile Gly Ser Leu Phe Leu Arg Glu Leu Ile Lys Glu Phe
                        725                 730                 735

Gly Thr Asp His Ile Tyr Gly Ala Asp Thr Phe Asn Glu Met Gln Pro
                        740                 745                 750

Pro Ser Ser Glu Pro Ser Tyr Leu Ala Ala Thr Thr Ala Val Tyr
                        755                 760                 765

Glu Ala Met Thr Ala Val Asp Thr Glu Ala Val Trp Leu Leu Gln Gly
                770                 775                 780

Trp Leu Phe Gln His Gln Pro Gln Phe Trp Gly Pro Ala Gln Ile Arg
        785                 790                 795                 800

Ala Val Leu Gly Ala Val Pro Arg Gly Arg Leu Leu Val Leu Asp Leu
                        805                 810                 815

Phe Ala Glu Ser Gln Pro Val Tyr Thr Arg Thr Ala Ser Phe Gln Gly
                        820                 825                 830

Gln Pro Phe Ile Trp Cys Met Leu His Asn Phe Gly Gly Asn His Gly
                        835                 840                 845

Leu Phe Gly Ala Leu Glu Ala Val Asn Gly Gly Pro Glu Ala Ala Arg
                850                 855                 860

Leu Phe Pro Asn Ser Thr Met Val Gly Thr Gly Met Ala Pro Glu Gly
        865                 870                 875                 880

Ile Ser Gln Asn Glu Val Val Tyr Ser Leu Met Ala Glu Leu Gly Trp
                        885                 890                 895

Arg Lys Asp Pro Val Pro Asp Leu Ala Ala Trp Val Thr Ser Phe Ala
                        900                 905                 910

Ala Arg Arg Tyr Gly Val Ser His Pro Asp Ala Gly Ala Ala Trp Arg
                        915                 920                 925

Leu Leu Leu Arg Ser Val Tyr Asn Cys Ser Gly Glu Ala Cys Arg Gly
                930                 935                 940

His Asn Arg Ser Pro Leu Val Arg Arg Pro Ser Leu Gln Met Asn Thr
        945                 950                 955                 960

Ser Ile Trp Tyr Asn Arg Ser Asp Val Phe Glu Ala Trp Arg Leu Leu
                        965                 970                 975

Leu Thr Ser Ala Pro Ser Leu Ala Thr Ser Pro Ala Phe Arg Tyr Asp
                        980                 985                 990

Leu Leu Asp Leu Thr Arg Gln Ala  Val Gln Glu Leu Val  Ser Leu Tyr
                        995                 1000                 1005

Tyr Glu  Glu Ala Arg Ser Ala  Tyr Leu Ser Lys Glu  Leu Ala Ser
                1010                 1015                 1020

Leu Leu  Arg Ala Gly Gly Val  Leu Ala Tyr Glu Leu  Leu Pro Ala
                1025                 1030                 1035

Leu Asp  Glu Val Leu Ala Ser  Asp Ser Arg Phe Leu  Leu Gly Ser
                1040                 1045                 1050
```

```
Trp Leu Glu Gln Ala Arg Ala Ala Ala Val Ser Glu Ala Glu Ala
    1055                1060                1065

Asp Phe Tyr Glu Gln Asn Ser Arg Tyr Gln Leu Thr Leu Trp Gly
    1070                1075                1080

Pro Glu Gly Asn Ile Leu Asp Tyr Ala Asn Lys Gln Leu Ala Gly
    1085                1090                1095

Leu Val Ala Asn Tyr Tyr Thr Pro Arg Trp Arg Leu Phe Leu Glu
    1100                1105                1110

Ala Leu Val Asp Ser Val Ala Gln Gly Ile Pro Phe Gln Gln His
    1115                1120                1125

Gln Phe Asp Lys Asn Val Phe Gln Leu Glu Gln Ala Phe Val Leu
    1130                1135                1140

Ser Lys Gln Arg Tyr Pro Ser Gln Pro Arg Gly Asp Thr Val Asp
    1145                1150                1155

Leu Ala Lys Lys Ile Phe Leu Lys Tyr Tyr Pro Arg Trp Val Ala
    1160                1165                1170

Gly Ser Trp
    1175

<210> SEQ ID NO 21
<211> LENGTH: 1180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
                20                  25                  30

Pro Gly Ala Leu Val Lys Ile Ser Cys Lys Ala Ser Gly Tyr Thr Phe
            35                  40                  45

Thr Asn Tyr Asp Ile His Trp Val Lys Gln Arg Pro Gly Gln Gly Leu
        50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
```

-continued

```
            210                 215                 220
Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
            355                 360                 365

Arg Asp Glu Leu Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Asp Glu Ala Arg
            450                 455                 460

Glu Ala Ala Ala Val Arg Ala Leu Val Ala Arg Leu Leu Gly Pro Gly
465                 470                 475                 480

Pro Ala Ala Asp Phe Ser Val Ser Val Glu Arg Ala Leu Ala Ala Lys
                485                 490                 495

Pro Gly Leu Asp Thr Tyr Ser Leu Gly Gly Gly Ala Ala Arg Val
            500                 505                 510

Arg Val Arg Gly Ser Thr Gly Val Ala Ala Ala Gly Leu His Arg
            515                 520                 525

Tyr Leu Arg Asp Phe Cys Gly Cys His Val Ala Trp Ser Gly Ser Gln
            530                 535                 540

Leu Arg Leu Pro Arg Pro Leu Pro Ala Val Pro Gly Glu Leu Thr Glu
545                 550                 555                 560

Ala Thr Pro Asn Arg Tyr Arg Tyr Tyr Gln Asn Val Cys Thr Gln Ser
                565                 570                 575

Tyr Ser Phe Val Trp Trp Asp Trp Ala Arg Trp Glu Arg Glu Ile Asp
            580                 585                 590

Trp Met Ala Leu Asn Gly Ile Asn Leu Ala Leu Ala Trp Ser Gly Gln
            595                 600                 605

Glu Ala Ile Trp Gln Arg Val Tyr Leu Ala Leu Gly Leu Thr Gln Ala
            610                 615                 620

Glu Ile Asn Glu Phe Phe Thr Gly Pro Ala Phe Leu Ala Trp Gly Arg
625                 630                 635                 640
```

```
Met Gly Asn Leu His Thr Trp Asp Gly Pro Leu Pro Ser Trp His
            645                 650                 655

Ile Lys Gln Leu Tyr Leu Gln His Arg Val Leu Asp Gln Met Arg Ser
            660                 665                 670

Phe Gly Met Thr Pro Val Leu Pro Ala Phe Ala Gly His Val Pro Glu
            675                 680                 685

Ala Val Thr Arg Val Phe Pro Gln Val Asn Val Thr Lys Met Gly Ser
            690                 695                 700

Trp Gly His Phe Asn Cys Ser Tyr Ser Cys Ser Phe Leu Leu Ala Pro
705                 710                 715                 720

Glu Asp Pro Ile Phe Pro Ile Ile Gly Ser Leu Phe Leu Arg Glu Leu
                725                 730                 735

Ile Lys Glu Phe Gly Thr Asp His Ile Tyr Gly Ala Asp Thr Phe Asn
            740                 745                 750

Glu Met Gln Pro Pro Ser Ser Glu Pro Ser Tyr Leu Ala Ala Ala Thr
            755                 760                 765

Thr Ala Val Tyr Glu Ala Met Thr Ala Val Asp Thr Glu Ala Val Trp
    770                 775                 780

Leu Leu Gln Gly Trp Leu Phe Gln His Gln Pro Gln Phe Trp Gly Pro
785                 790                 795                 800

Ala Gln Ile Arg Ala Val Leu Gly Ala Val Pro Arg Gly Arg Leu Leu
                805                 810                 815

Val Leu Asp Leu Phe Ala Glu Ser Gln Pro Val Tyr Thr Arg Thr Ala
                820                 825                 830

Ser Phe Gln Gly Gln Pro Phe Ile Trp Cys Met Leu His Asn Phe Gly
            835                 840                 845

Gly Asn His Gly Leu Phe Gly Ala Leu Glu Ala Val Asn Gly Gly Pro
850                 855                 860

Glu Ala Ala Arg Leu Phe Pro Asn Ser Thr Met Val Gly Thr Gly Met
865                 870                 875                 880

Ala Pro Glu Gly Ile Ser Gln Asn Glu Val Val Tyr Ser Leu Met Ala
                885                 890                 895

Glu Leu Gly Trp Arg Lys Asp Pro Val Pro Asp Leu Ala Ala Trp Val
            900                 905                 910

Thr Ser Phe Ala Ala Arg Arg Tyr Gly Val Ser His Pro Asp Ala Gly
            915                 920                 925

Ala Ala Trp Arg Leu Leu Leu Arg Ser Val Tyr Asn Cys Ser Gly Glu
    930                 935                 940

Ala Cys Arg Gly His Asn Arg Ser Pro Leu Val Arg Arg Pro Ser Leu
945                 950                 955                 960

Gln Met Asn Thr Ser Ile Trp Tyr Asn Arg Ser Asp Val Phe Glu Ala
            965                 970                 975

Trp Arg Leu Leu Leu Thr Ser Ala Pro Ser Leu Ala Thr Ser Pro Ala
            980                 985                 990

Phe Arg Tyr Asp Leu Leu Asp Leu Thr Arg Gln Ala Val Gln Glu Leu
            995                 1000                1005

Val Ser Leu Tyr Tyr Glu Glu Ala Arg Ser Ala Tyr Leu Ser Lys
            1010                1015                1020

Glu Leu Ala Ser Leu Leu Arg Ala Gly Gly Val Leu Ala Tyr Glu
            1025                1030                1035

Leu Leu Pro Ala Leu Asp Glu Val Leu Ala Ser Asp Ser Arg Phe
            1040                1045                1050
```

Leu Leu Gly Ser Trp Leu Glu Gln Ala Arg Ala Ala Val Ser
    1055                1060                1065

Glu Ala Glu Ala Asp Phe Tyr Glu Gln Asn Ser Arg Tyr Gln Leu
    1070                1075                1080

Thr Leu Trp Gly Pro Glu Gly Asn Ile Leu Asp Tyr Ala Asn Lys
    1085                1090                1095

Gln Leu Ala Gly Leu Val Ala Asn Tyr Tyr Thr Pro Arg Trp Arg
    1100                1105                1110

Leu Phe Leu Glu Ala Leu Val Asp Ser Val Ala Gln Gly Ile Pro
    1115                1120                1125

Phe Gln Gln His Gln Phe Asp Lys Asn Val Phe Gln Leu Glu Gln
    1130                1135                1140

Ala Phe Val Leu Ser Lys Gln Arg Tyr Pro Ser Gln Pro Arg Gly
    1145                1150                1155

Asp Thr Val Asp Leu Ala Lys Lys Ile Phe Leu Lys Tyr Tyr Pro
    1160                1165                1170

Arg Trp Val Ala Gly Ser Trp
    1175            1180

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ser Ser Ser
1

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccgagctcgg taccaagctt                                              20

```
<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Leu Lys Thr Pro Leu Gly Asp Thr Thr His Thr
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Pro Arg Cys Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Pro Glu Phe Leu Gly Gly Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser
1               5

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gagtggcacc ttccagggtc aag                                             23
```